(12) United States Patent
Breslow et al.

(10) Patent No.: US 9,499,479 B2
(45) Date of Patent: Nov. 22, 2016

(54) MOLECULES THAT SELECTIVELY INHIBIT HISTONE DEACETYLASE 6 RELATIVE TO HISTONE DEACETYLASE 1

(71) Applicants: Ronald Breslow, New York, NY (US); Paul A. Marks, Washington, CT (US)

(72) Inventors: Ronald Breslow, New York, NY (US); Paul A. Marks, Washington, CT (US)

(73) Assignees: THE TRUSTEES OF COLUMBIA UNIVERSITY IN THE CITY OF NEW YORK, New York, NY (US); SLOAN-KETTERING INSTITUTE FOR CANCER RESEARCH, New York, NY (US)

( * ) Notice: Subject to any disclaimer, the term of this patent is extended or adjusted under 35 U.S.C. 154(b) by 0 days.

(21) Appl. No.: 14/349,291

(22) PCT Filed: Oct. 3, 2012

(86) PCT No.: PCT/US2012/000459
§ 371 (c)(1),
(2) Date: Apr. 2, 2014

(87) PCT Pub. No.: WO2013/052110
PCT Pub. Date: Apr. 11, 2013

(65) Prior Publication Data
US 2014/0288119 A1 Sep. 25, 2014

Related U.S. Application Data

(60) Provisional application No. 61/542,598, filed on Oct. 3, 2011, provisional application No. 61/620,783, filed on Apr. 5, 2012.

(51) Int. Cl.
*C07C 25/10* (2006.01)
*C07C 259/08* (2006.01)
(Continued)

(52) U.S. Cl.
CPC .......... *C07C 259/10* (2013.01); *C07C 259/06* (2013.01); *C07C 275/64* (2013.01);
(Continued)

(58) Field of Classification Search
CPC . C07C 259/10; C07C 259/08; C07D 213/81; C07D 213/53; C07D 213/89; C07D 213/82; C07D 215/40; C07D 233/90; C07D 241/38; C07D 249/04; C07D 261/18; C07D 333/38
See application file for complete search history.

(56) References Cited

U.S. PATENT DOCUMENTS 4,309,212 A   1/1982   Takemoto et al.
5,369,108 A   11/1994  Breslow et al.
(Continued)

FOREIGN PATENT DOCUMENTS

EP   0434074 A2   6/1991
EP   1736465 A1   12/2006
(Continued)

OTHER PUBLICATIONS

Notification of Transmittal of the International Search Report and the Written Opinion of the International Searching Authority, or the Declaration, including an International Search Report and Written Opinion of the International Searching Authority, mailed Dec. 11, 2012 in connection with PCT International Application No. PCT/US2012/000459, filed Oct. 3, 2012.
(Continued)

*Primary Examiner* — Timothy Thomas
(74) *Attorney, Agent, or Firm* — John P. White; Cooper & Dunham LLP

(57) ABSTRACT

This invention provides a compound having the structure:

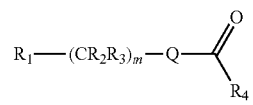

wherein
$R_1$ is H, halogen, $-NR_5R_6$, $-NR_5-C(=O)-R_6$, $-NH-C(=O)-OR_7$, $-OR_7$, $-NO_2$, $-CN$, $-SR_7$, $-SO_2R_7$, $-CO_2R_7$, $CF_3$, $-SOR_7$, $-POR_7$, $-C(=S)R_7$, $-C(=O)-NR_5R_6$, $-CH_2-C(=O)-NR_5R_6$, $-C(=NR_5)R_6$, $-P(=O)(OR_5)(OR_6)$, $-P(OR_5)(OR_6)$, $-C(=S)R_7$, $C_{1-5}$ alkyl, $C_{2-5}$ alkenyl, $C_{2-5}$ alkynyl, aryl, heteroaryl, or heterocyclyl,
wherein $R_5$, $R_6$, and $R_7$ and are each, independently, H, $C_{1-5}$ alkyl, $C_{2-5}$ alkenyl, $C_{2-5}$ alkynyl, heteroalkyl, cycloalkyl, heterocycloalkyl, aryl, or heteroaryl;
m is an integer from 0 to 2;
$R_2$ and $R_3$ are each, independently, H, halogen, $-NH_2$, $-CX_3$, $-C(=O)OR_8$, $C(=O)R_8$, $-C(=O)NR_9R_{10}$, $C_{1-10}$ alkyl, $C_{2-10}$ alkenyl, $C_{2-10}$ alkynyl, heteroalkyl, aryl, heteroaryl, or heterocyclyl;
wherein
X is Cl, Br, or F;
$R_8$, $R_9$ and $R_{10}$ are each, independently, H, $C_{1-5}$ alkyl, $C_{2-5}$ alkenyl, $C_{2-5}$ alkynyl, heteroalkyl, cycloalkyl, heterocycloalkyl, aryl, or heteroaryl;
Q is $-Ar_1-Z-$ or $-Z-Ar_1-Z-$,
wherein $Ar_1$ is aryl or heteroaryl; and
each occurrence of Z is independently present or absent, and when present is $-O-$, $-S-$, $-CH_2-$, $-C(O)-$
$-NH-$, $-NH-NH-$, $-NHC(=O)-$, $-C(=O)NH-$, $-NHC(=O)CH_2NH-$,
$-NHC(=O)CH_2C(=O)-$, $-N(OH)-$, $-CH_2CH_2-$ or
$-NHC(=O)CH=CH-$; and
$R_4$ is alkyl, $-OR_{11}$ or $-NH-OR_{11}$,
wherein $R_{11}$ is H, $C_{1-10}$ alkyl, $C_{2-10}$ alkenyl, $C_{2-10}$ alkynyl, aryl, heteroaryl, or heterocyclyl, and
when Q is $-Ar_1-Z-$, Z is absent, $Ar_1$ is phenyl, $R_2$ and $R_3$ are H, n=1, and $R_4$ is $-NHOH$, then $R_1$ is other than carbazole, tetrahydro-β-carboline, tetrahydro-γ-carboline, $-C(=O)-NR_5R_6$ and $-NR_5-C(=O)-R_6$, wherein one of $R_5$ or $R_6$ is quinoline and the other of $R_5$ or $R_6$ is H;
or a pharmaceutically acceptable salt thereof.

19 Claims, 4 Drawing Sheets

(51) Int. Cl.
| | |
|---|---|
| C07C 259/10 | (2006.01) |
| C07D 215/40 | (2006.01) |
| C07D 235/06 | (2006.01) |
| C07D 209/08 | (2006.01) |
| C07D 209/18 | (2006.01) |
| C07C 259/06 | (2006.01) |
| C07C 275/64 | (2006.01) |
| C07D 209/24 | (2006.01) |
| C07D 209/42 | (2006.01) |
| C07D 215/06 | (2006.01) |

(52) U.S. Cl.
CPC .......... C07D209/08 (2013.01); C07D 209/18 (2013.01); C07D 209/24 (2013.01); C07D 209/42 (2013.01); C07D 215/06 (2013.01); C07D 215/40 (2013.01); C07D 235/06 (2013.01); C07C 2102/10 (2013.01)

(56) References Cited

U.S. PATENT DOCUMENTS

| | | | |
|---|---|---|---|
| 5,932,616 | A | 8/1999 | Breslow et al. |
| 6,087,367 | A * | 7/2000 | Breslow ............... A61K 31/221 514/263.21 |
| 7,282,522 | B2 | 10/2007 | Rho et al. |
| 7,345,174 | B2 | 3/2008 | Breslow et al. |
| 2004/0087631 | A1 | 5/2004 | Bacopoulos et al. |
| 2004/0122079 | A1 | 6/2004 | Grossmann et al. |
| 2005/0119305 | A1 | 6/2005 | Naka et al. |
| 2006/0241129 | A1 | 10/2006 | Breslow et al. |
| 2006/0252834 | A1 | 11/2006 | Rho et al. |
| 2007/0010669 | A1 | 1/2007 | Breslow et al. |
| 2007/0213392 | A1 | 9/2007 | Miller et al. |
| 2008/0015190 | A1 * | 1/2008 | Chakravarty ......... C07C 259/10 514/235.2 |
| 2008/0139673 | A1 | 6/2008 | Hu et al. |
| 2008/0200489 | A1 | 8/2008 | Atadja et al. |
| 2008/0248506 | A1 | 10/2008 | Bass et al. |
| 2009/0023786 | A1 | 1/2009 | Miller et al. |
| 2010/0022514 | A1 | 1/2010 | Cho et al. |
| 2011/0212943 | A1 | 9/2011 | Balasubramanian et al. |
| 2013/0261130 | A1 * | 10/2013 | Ahmed ................. C07C 231/02 514/252.13 |
| 2014/0031368 | A1 | 1/2014 | Breslow et al. |

FOREIGN PATENT DOCUMENTS

| | | |
|---|---|---|
| EP | 2045239 A1 | 4/2009 |
| WO | WO 02/26696 A1 | 4/2002 |
| WO | WO 2005/055928 A1 | 6/2005 |
| WO | WO 2005/080367 A1 | 9/2005 |
| WO | WO 2006/101454 A1 | 9/2006 |
| WO | WO 2006/117548 A1 | 11/2006 |
| WO | WO 2007/124435 A2 | 11/2007 |
| WO | WO 2008/055068 A1 | 5/2008 |
| WO | WO 2006/101454 A1 | 1/2011 |
| WO | WO 2011/146855 A1 | 11/2011 |
| WO | WO/2013/052110 A1 | 4/2013 |
| WO | WO 2015/100363 A1 | 7/2015 |

OTHER PUBLICATIONS

International Preliminary Report on Patentability Chapter I in connection with PCT International Application No. PCT/US2011/037372 issued Nov. 27, 2012.
Written Opinion of the International Search Authority in connection with PCT International Application No. PCT/US2012/000459 issued Dec. 11, 2012.
International Preliminary Report on Patentability Chapter I in connection with PCT International Application No. PCT/US2012/000459 issued Apr. 17, 2014.
International Search Report in connection with PCT International application No. PCT/US2012/000459 issued Dec. 11, 2012.
R.B. Parmigiani et al. HDAC6 is a specific deacetylase of peroxiredoxins and is involved in redox regulation. PNAS (2008), 105(28), pp. 9633-9638.
Bieliauskas, A.V. and Pflum, M.K. Isoform-selective histone deacetylase inhibitors. Chem Soc Rev. (2008), 37(7), pp. 1402-1413.
Belvedere, S. et al. Aminosuberoyl hydroxamic acids (ASHAs): a potent new class of HDAC inhibitors. Bioorg Med Chem Lett. (2007), 17(14), 3969-71.
Bali, P. et al. nhibition of Histone Deacetylase 6 Acetylates and Disrupts the Chaperone Function of Heat Shock Protein 90. Journal of Biological Chemistry. (2005), 280, pp. 26729-26734.
Gao et al. The Microtubule-associated Histone Deacetylase 6 (HDAC6) Regulates Epidermal Growth Factor Receptor (EGFR) Endocytic Trafficking and Degradation. Journal of Biological Chemistry. (2010), 285, pp. 11219-11226.
Kovacs, J.J. et al. HDAC6 Regulates Hsp90 Acetylation Short Article and Chaperone-Dependent Activation of Glucocorticoid Receptor. Molecular Cell. (2005), 18, pp. 601-607.
Haggarty, S.J. et al. Domain-selective small-molecule inhibitor of histone deacetylase 6 (HDAC6)-mediated tubulin deacetvlation. PNAS (2003), 100, pp. 4389-4394.
Butler, K.V. et al. Chemical Origins of Isoform Selectivity in Histone Deacetylase Inhibitors. Current Pharmaceutical Design. (2008) 14, pp 505-528.
Kawaguchi, Y. et al. "The Deacetylase HDAC6 Regulates Aggresome Formation and Cell Viability in Response to Misfolded Protein Stress" (2003) Cell, vol. 115, 727-738.
Supplementary European Search Report issued Aug. 20, 2014 in connection with European Application No. 11784333.4.
Kozikowski, A.P. et al. Use of the nitrile oxide cycloaddition (NOC) reaction for molecular probe generation: a new class of enzyme selective histone deacetylase inhibitors (HDACIs) showing picomolar activity at HDAC6. J. Med. Chem. (2008) 51, 4370-7373.
Hong, J. et al. A New Approach to Tubacin. Letters in Organic Chemistry. (2010) 7, 50-53.
Griffith, D. A novel anti-cancer bifunctional platinum drug candidate with dual DNA binding and histone deacetylase inhibitory activity. Chem Commun (Camb). (2009) 28, 44, 6735-7.
Siliphaivanh, P, et al. Design of novel histone deacetylase inhibitors. Bioorg Med Chem Lett. (2007), 17(16), pp. 4619-4624.
Estiu et al. Structural origin of selectivity in class II-selective histone deacetylase inhibitors. J Med Chem. (2008), 51(10), pp. 2898-2906.
Office Action issued Mar. 18, 2014 in connection with U.S. Appl. No. 13/937,128.
Final Office Action issued Jan. 28, 2015 in connection with U.S. Appl. No. 13/937,128.
International Search Report in connection with PCT International Application No. PCT/US2011/037372 issued Aug. 17, 2011.
Written Opinion of the International Search Authority in connection with PCT International Application No. PCT/US2011/037372 issued Aug. 17, 2011.
CAS Abstract for Canonica & Tedechi, 13 Farmaco, Edizione Scientiifca (1958), 286-93.
CAS Abstract for JP 510014124, published Apr. 18, 1974 (Harita et al.).
Office Action issued Aug. 7, 2014 in connection with U.S. Appl. No. 13/937,128.
Office Action issued Aug. 21, 2015 in connection with U.S. Appl. No. 13/937,128.
Communication Pursuant to 94(3) EPC issued Aug. 5, 2015 in connection with European Application No. 11784333.4.
Invitation Pursuant to Rule 63(1) EPC issued Jun. 26, 2015 in connection with European Application No. 12838935.0.
Written Opinion of the International Search Authority in connection with PCT International Application No. PCT/US2014/072234, issued Mar. 18, 2015.
International Search Report in connection with PCT International Application No. PCT/US2014/072234, issued Mar. 18, 2015.

(56) References Cited

OTHER PUBLICATIONS

Office Action issued Sep. 4, 2015 in connection with Australian Patent Application No. 2011255281.
Office Action issued Nov. 13, 2015 in connection with Australian Patent Application No. 2012319188.
Extended European Search Report issued Oct. 20, 2016 in connection with European Application No. 12838935.0.
Uesato, S. et al. Novel histone deacetylase inhibitors: N-hydroxycarboxamides possessing a terminal bicyclic aryl group. Bioorg. Med. Chem. Lett. (2002) 12, 1347-1349.
Maeda, T. et al. Potent histone deacetylase inhibitors: N-hydroxybenzamides with antitumor activities. Bioorg. Med. Chem. (2004) 12, 4351-4360.
Butler et al. Rational Design and Simple Chemistry Yield a Superior, Neuroprotective HDAC6 Inhibitor, Tubastatin A. J. Am. Chem. Soc. (2010) 132, 10842-10846.
Smil, D.V. et al. Novel HDAC6 isoform selective chiral small molecule histone deacetylase inhibitors. Bioorg. Med. Chem. Lett. (2009) 19, 688-692.
Marastoni, E. et al. Benzofused hydroxamic acids: Useful fragments for the preparation of histone deacetylase inhibitors. Part 1: Hit identification. Bioorg. Med. Chem. Lett. (2013) 23, 4091-4095.
Lee, J. et al. Development of a histone deacetylase 6 inhibitor and its biological effects PNAS (2013) 110, 15704-15709.
Patent Examination Report No. 2 issued Jul. 15, 2016 in connection with Australian Patent Application No. 2012319188.

\* cited by examiner

MOLECULES THAT SELECTIVELY INHIBIT HISTONE DEACETYLASE 6 RELATIVE TO HISTONE DEACETYLASE 1

This application is a §371 national stage of PCT International Application No. PCT/US2012/000459, filed Oct. 3, 2012, claiming the benefit of U.S. Provisional Applications No. 61/620,783, filed Apr. 5, 2012 and 61/542,598, filed Oct. 3, 2011, the contents of each of which are hereby incorporated by reference in their entirety.

Throughout this application, certain publications are referenced in parentheses. Full citations for these publications may be found immediately preceding the claims. The disclosures of these publications in their entireties are hereby incorporated by reference into this application in order to describe more fully the state of the art to which this invention relates.

BACKGROUND OF THE INVENTION

To date, eighteen histone deacetylases (HDACs) have been identified in humans. Eleven HDACs (HDAC1-11) are zinc-dependent and seven HDACs, designated sirtuins 1-7, are NAD+-dependent (1). Aberrant activity of HDACs has been implicated in many disease states, including cancer (2). When zinc-dependent HDACs are inhibited, the levels of acetylation of certain proteins are elevated, with many resulting physiological effects. Many inhibitors of HDACs have been developed for use against cancers and other disease states. One well-known HDAC inhibitor, suberoylanilide hydroxamic acid (SAHA, Vorinostat), was approved in 2006 for human use following the results of more than 100 human trials against various forms of cancer and is currently in use. Phase I, II and III clinical trials with vorinostat as single therapy and in combination therapy with various anti-cancer agents for hematologic and solid neoplasms are ongoing.

While HDACs are associated with deacetylation of histones in the context of gene expression and chromatin remodeling, there is abundant evidence indicating that not all functions of HDACs are dedicated to deacetylation of histones. Rather, some HDACs have been shown to exert deacetylase activity on proteins other than histones. One such HDAC is HDAC6, a cytoplasmic, microtubule-associated deacetylase, which has been found to regulate microtubule acetylation and chemotactic cell motility (3).

HDAC6 is predominantly a cytoplasmic, microtubule-associated member of the class IIB family of histone deacetylases. HDAC6 possesses two catalytic domains, a ubiquitin-binding domain and a C-terminal zinc finger domain (4). HDAC6 catalyzes deacetylation of cytoplasmic protein substrates, such as α-tubulin, Hsp90, peroxiredoxins, and cortactin (4). HDAC6 has also been demonstrated to direct misfolded protein aggregates into aggresomes, which are major repositories formed to manage excessive levels of misfolded and aggregated protein for eventual elimination. Aggresomes are of clinical interest as they are similar to cytoplasmic inclusion bodies commonly observed in neurodegenerative diseases (5).

Haggarty et al. (6) have shown that the C-terminal catalytic domain of HDAC6, the domain responsible for α-tubulin deacetylation, can be inhibited by the small-molecule inhibitor, tubacin. Haggarty et al found that the inhibition of HDAC6 with tubacin did not affect the stability of microtubules, but decreased cell motility. Given the dependence of metastasis and angiogenesis on cell movement, increasing the acetylation level of α-tubulin may be an important component to the antimetastatic and antiangiogenic activities of HDAC inhibitors (6).

Heat shock protein 90 (Hsp90) is an important chaperone protein involved in protein folding and is overexpressed in many cancer cell types (2, 7). The disruption of the folding and chaperoning functions of Hsp90 causes its client proteins to be destabilized and eventually degraded. HDAC6 is an attractive target for cancer treatment because acetylated Hsp90 has a reduced ability to perform its chaperoning function (2, 7), with consequent activation of the intrinsic pathway of apoptosis.

In general, for diseases caused by aberrant gene transcription, the most effective treatment would involve targeting only the genes relevant to the disease (2). In the context of HDAC inhibitor treatment, this would involve inhibiting only those HDAC isoforms relevant to the disease state, thereby minimizing changes not related to the disease, and possibly reducing side effects and toxicity. While SAHA combines efficacy with minimum toxicity, its inhibitory activity is not selective among the known human HDACs.

Marks & Breslow (8, 9) describes the development of HDAC inhibitor voronistat as an anti-cancer drug. HDAC inhibitors have also been identified as a correction for cholesterol and sphingolipid transport defects in human Niemann-Pick type C disease (10).

In view of the importance of inhibiting only those HDAC isoforms relevant to a disease state, minimizing acetylation of proteins not related to the disease, and reducing side effects and toxicity, new HDAC inhibitors that are selective for specific HDACs are needed. Herein, new selective HDAC inhibitors are described.

SUMMARY OF THE INVENTION

This invention provides a compound having the structure:

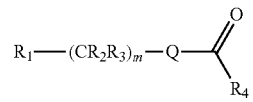

wherein $R_1$ is H, halogen, $-NR_5R_6$, $-NR_5-C(=O)-R_6$, $-NH-C(=O)-OR_7$, $-OR_7$, $-NO_2$, $-CN$, $-SR_7$, $-SO_2R_7$, $-CO_2R_7$, $CF_3$, $-SOR_7$, $-POR_7$, $-C(=S)R_7$, $-C(=O)-NR_5R_6$, $-CH_2-C(=O)-NR_5R_6$, $-C(=NR_5)R_6$, $-P(=O)(OR_5)(OR_6)$, $-P(OR_5)(OR_6)$, $-C(=S)R_7$, $C_{1-5}$ alkyl, $C_{2-5}$ alkenyl, $C_{2-5}$ alkynyl, aryl, heteroaryl, or heterocyclyl, wherein $R_5$, $R_6$, and $R_7$ and are each, independently, H, $C_{1-5}$ alkyl, $C_{2-5}$ alkenyl, $C_{2-5}$ alkynyl, heteroalkyl, cycloalkyl, heterocycloalkyl, aryl, or heteroaryl;

m is an integer from 0 to 2;

$R_2$ and $R_3$ are each, independently, H, halogen, $-NH_2$, $-CX_3$, $-C(=O)OR_8$, $C(=O)R_8$, $-C(=O)NR_9R_{10}$, $C_{1-10}$ alkyl, $C_{2-10}$ alkenyl, $C_{2-10}$ alkynyl, heteroalkyl, aryl, heteroaryl, or heterocyclyl;

wherein

X is Cl, Br, or F;

$R_8$, $R_9$ and $R_{10}$ are each, independently, H, $C_{1-5}$ alkyl, $C_{2-5}$ alkenyl, $C_{2-5}$ alkynyl, heteroalkyl, cycloalkyl, heterocycloalkyl, aryl, or heteroaryl;

Q is —Ar$_1$—Z— or —Z—Ar$_1$—Z—,
  wherein Ar$_1$ is aryl or heteroaryl; and
  each occurrence of Z is independently present or absent, and when present is —O—, —S—, —CH$_2$—, —C(O)—, —NH—, —NH—NH—, —NHC(=O)—, —C(=O)NH—, —NHC(=O)CH$_2$NH—, —NHC(=O)CH$_2$C(=O)—, —N(OH)—, —CH$_2$CH$_2$— or —NHC(=O)CH=CH—; and R$_4$ is alkyl, —OR$_{11}$ or —NH—OR$_{11}$,
  wherein R$_{11}$ is H, C$_{1-10}$ alkyl, C$_{2-10}$ alkenyl, C$_{2-10}$ alkynyl, aryl, heteroaryl, or heterocyclyl, and
  when Q is —Ar$_1$—Z—, Z is absent, Ar$_1$ is phenyl, R$_2$ and R$_3$ are H, n=1, and R$_4$ is —NHOH, then R$_1$ is other than carbazole, tetrahydro-β-carboline, tetrahydro-γ-carboline, —C(=O)—NR$_5$R$_6$ and —NR$_5$—C(=O)—R$_6$, wherein one of R$_5$ or R$_6$ is quinoline and the other of R$_5$ or R$_6$ is H;

or a pharmaceutically acceptable salt thereof.

DETAILED DESCRIPTION OF THE INVENTION

Figure 1:
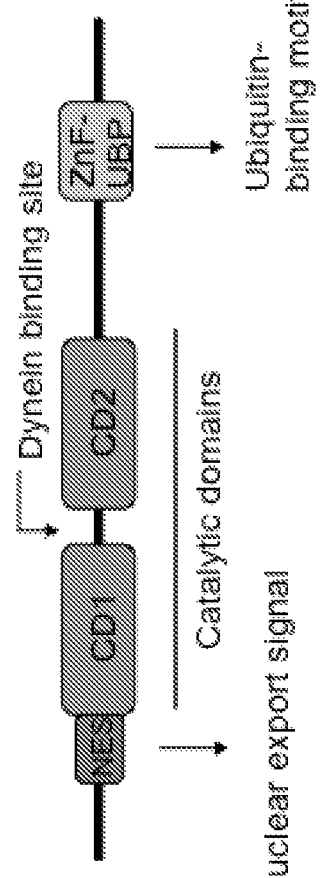
FIG. 1. Schematic representation of HDAC6.

This invention provides a compound having the structure:

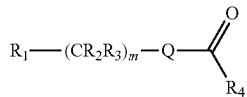

wherein
R$_1$ is H, halogen, —NR$_5$R$_6$, —NR$_5$—C(=O)—R$_6$, —NH—C(=O)—OR$_7$, —OR$_7$, —NO$_2$, —CN, —SR$_7$, —SO$_2$R$_7$, —CO$_2$R$_7$, CF$_3$, —SOR$_7$, —POR$_7$, —C(=S)R$_7$, —C(=O)—NR$_5$R$_6$, —CH$_2$—C(=O)—NR$_5$R$_6$, —C(=NR$_5$)R$_6$, —P(=O)(OR$_5$)(OR$_6$), —P(OR$_5$)(OR$_6$), —C(=S)R$_7$, C$_{1-5}$ alkyl, C$_{2-5}$ alkenyl, C$_{2-5}$ alkynyl, aryl, heteroaryl, or heterocyclyl,
  wherein R$_5$, R$_6$, and R$_7$ and are each, independently, H, C$_{1-5}$ alkyl, C$_{2-5}$ alkenyl, C$_{2-5}$ alkynyl, heteroalkyl, cycloalkyl, heterocycloalkyl, aryl, or heteroaryl;
m is an integer from 0 to 2;
R$_2$ and R$_3$ are each, independently, H, halogen, —NH$_2$, —CX$_3$, —C(=O) OR$_8$, C(=O)R$_8$, —C(=O) NR$_9$R$_{10}$, C$_{1-10}$ alkyl, C$_{2-10}$ alkenyl, C$_{2-10}$ alkynyl, heteroalkyl, aryl, heteroaryl, or heterocyclyl;
  wherein
  X is Cl, Br, or F;
  R$_8$, R$_9$ and R$_{10}$ are each, independently, H, C$_{1-5}$ alkyl, C$_{2-5}$ alkenyl, C$_{2-5}$ alkynyl, heteroalkyl, cycloalkyl, heterocycloalkyl, aryl, or heteroaryl;
Q is —Ar$_1$—Z— or —Z—Ar$_1$—Z—,
  wherein Ar$_1$ is aryl or heteroaryl; and
  each occurrence of Z is independently present or absent, and when present is —O—, —S—, —CH$_2$—, —C(O)— —NH—, —NH—NH—, —NHC(=O)—, —C(=O)NH—, —NHC(=O)CH$_2$NH—, —NHC(=O)CH$_2$C(=O)—, —N(OH)—, —CH$_2$CH$_2$— or —NHC(=O)CH=CH—; and
R$_4$ is alkyl, —OR$_{11}$ or —NH—OR$_{11}$,
  wherein R$_{11}$ is H, C$_{1-10}$ alkyl, C$_{2-10}$ alkenyl, C$_{2-10}$ alkynyl, aryl, heteroaryl, or heterocyclyl, and
  when Q is —Ar$_1$—Z—, Z is absent, Ar$_1$ is phenyl, R$_2$ and R$_3$ are H, n=1, and R$_4$ is —NHOH, then R$_1$ is other than carbazole, tetrahydro-β-carboline, tetrahydro-γ-carboline, —C(=O)—NR$_5$R$_6$ and —NR$_5$—C(=O)—R$_6$, wherein one of R$_5$ or R$_6$ is quinoline and the other of R$_5$ or R$_6$ is H;

or a pharmaceutically acceptable salt thereof.

In some embodiments, the compound wherein
  wherein Q is —Ar$_1$—Z—, —Z—Ar$_1$— or —Z—Ar$_1$—Z— or a pharmaceutically acceptable salt thereof.

This invention provides a compound having the structure:

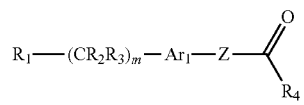

wherein
R$_1$ is H, halogen, —NR$_5$R$_6$, —NR$_5$—C(=O)—R$_6$, —NH—C(=O)—OR$_7$, —OR$_7$, —NO$_2$, —CN, —SR$_7$, —SO$_2$R$_7$, —CO$_2$R$_7$, CF$_3$, —SOR$_7$, —POR$_7$, —C(=S)R$_7$, —C(=O)—NR$_5$R$_6$, —CH$_2$—C(=O)—NR$_5$R$_6$, —C(=NR$_5$)R$_6$, —P(=O)(OR$_5$)(OR$_6$), —P(OR$_5$)(OR$_6$), —C(=S)R$_7$, C$_{1-5}$ alkyl, C$_{2-5}$ alkenyl, C$_{2-5}$ alkynyl, aryl, heteroaryl, or heterocyclyl,
  wherein R$_5$, R$_6$, and R$_7$ and are each, independently, H, C$_{1-5}$ alkyl, C$_{2-5}$ alkenyl, C$_{2-5}$ alkynyl, heteroalkyl, cycloalkyl, heterocycloalkyl, aryl, or heteroaryl;
m is an integer from 0 to 2;
R$_2$ and R$_3$ are each, independently, H, halogen, —NH$_2$, —CX$_3$, —C(=O) OR$_8$, C(=O)R$_8$, —C(=O) NR$_9$R$_{10}$, C$_{1-10}$ alkyl, C$_{2-10}$ alkenyl, C$_{2-10}$ alkynyl, heteroalkyl, aryl, heteroaryl, or heterocyclyl;
  wherein
  X is Cl, Br, or F;
  R$_8$, R$_9$ and R$_{10}$ are each, independently, H, C$_{1-5}$ alkyl, C$_{2-5}$ alkenyl, C$_{2-5}$ alkynyl, heteroalkyl, cycloalkyl, heterocycloalkyl, aryl, or heteroaryl;
Ar$_1$ is aryl or heteroaryl;
Z is present or absent, and when present is —O—, —S—, —CH$_2$—, —C(O)—, —NH—, —NH—NH—, —NHC(=O)—, —C(=O)NH—, —NHC(=O)CH$_2$NH— or —NHC(=O)CH=CH—; and
R$_4$ is —OR$_{11}$ or —NH—OR$_{11}$,
  wherein R$_{11}$ is H, C$_{1-10}$ alkyl, C$_{2-10}$ alkenyl, C$_{2-10}$ alkynyl, aryl, heteroaryl, or heterocyclyl, and
  when Z is absent, Ar$_1$ is phenyl, R$_2$ and R$_3$ are H, n=1, and R$_4$ is —NHOH, then R$_1$ is other than carbazole, tetrahydro-β-carboline, tetrahydro-γ-carboline, —C(=O)—NR$_5$R$_6$ and —NR$_5$—C(=O)—R$_6$, wherein one of R$_5$ or R$_6$ is quinoline and the other of R$_5$ or R$_6$ is H;

or a pharmaceutically acceptable salt thereof.

In some embodiments, the compound wherein Z is present and is —O—, —S—, —CH₂—, —NH—, —C(O)—, —NH—NH—, —NHC(=O)—, —C(=O)NH—, —NHC(=O)CH₂NH— or —NHC(=O)CH=CH—,
or a pharmaceutically acceptable salt thereof.

In some embodiments, the compound wherein Z is present and is —O—, —S—, —NH—, —(CO)—, —NH—NH—, —NHC(=O)—, —C(=O)NH—, —NHC(=O)CH₂NH— or —NHC(=O) CH=CH—,
or a pharmaceutically acceptable salt thereof.

In some embodiments, the compound wherein Z is —NH—, —NHC(=O), —NHC(=O)CH₂NH— or —NHC(=O)CH=CH—,
or a pharmaceutically acceptable salt thereof.

In some embodiments, the compound wherein Ar₁ is

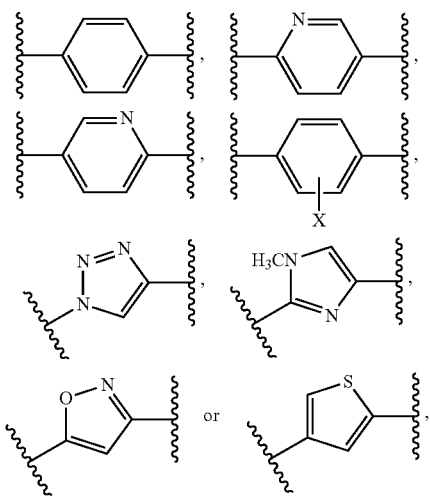

wherein X is a Cl, Br, or F,
or a pharmaceutically acceptable salt thereof.

In some embodiments, the compound wherein Ar₁ is

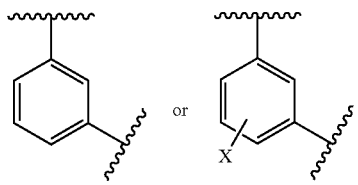

wherein X is Cl, Br, or F,
or a pharmaceutically acceptable salt thereof.

In some embodiments, the compound wherein R₁ is —C(=O)—NR₅R₆ or —NR₅—C(=O)—R₆,
wherein
R₅ is alkyl, heteroalkyl, cycloalkyl, aryl or heteroaryl; and
R₆ is alkyl, heteroalkyl, cycloalkyl, aryl or heteroaryl,
or a pharmaceutically acceptable salt thereof.

In some embodiments, the compound wherein R₅ is

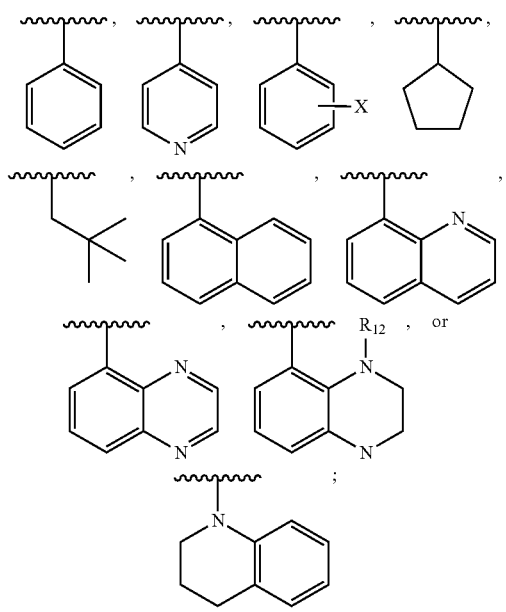

wherein
X is a Cl, Br, or F;
R₁₂ is H, C₁₋₅ alkyl, C₂₋₅ alkenyl, C₂₋₅ alkynyl, heteroalkyl, cycloalkyl, heterocycloalkyl, aryl, or heteroaryl; and
R₆ is H,

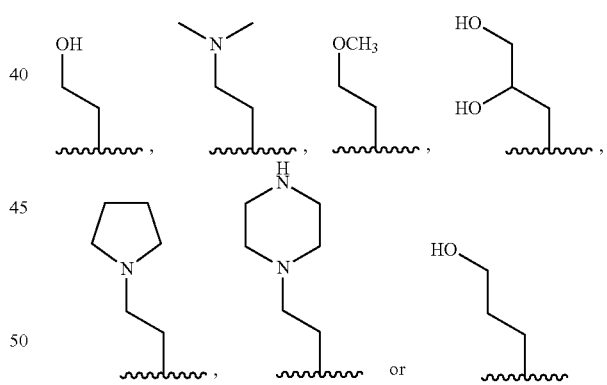

or a pharmaceutically acceptable salt thereof.

In some embodiments, the compound wherein
m=1;
R₂ is H or CH₃; and
R₃ is H, CH₃, Cl, Br, F, or CF₃;
or a pharmaceutically acceptable salt thereof.

In some embodiments, the compound wherein R₆ is —NH—OR₁₁ or —OR₁₁, wherein R₁₁ is H or CH₃,
or a pharmaceutically acceptable salt thereof.

In some embodiments, the compound wherein Z is absent,
or a pharmaceutically acceptable salt thereof.

In some embodiments, the compound wherein Ar₁ is

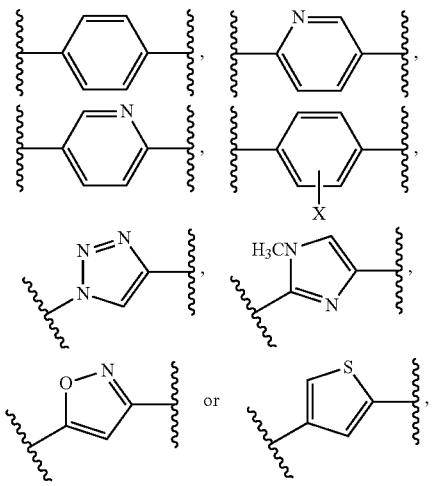

wherein X is a Cl, Br, or F,
or a pharmaceutically acceptable salt thereof.

In some embodiments, the compound wherein Ar₁ is

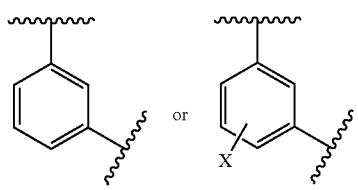

wherein X is Cl, Br, or F,
or a pharmaceutically acceptable salt thereof.

In some embodiments, the compound
wherein R₁ is —C(=O)—NR₅R₆ or —NR₅—C(=O)—R₆,
wherein
R₅ is alkyl, heteroalkyl cycloalkyl, aryl or heteroaryl; and
R₆ is alkyl, heteroalkyl, cycloalkyl, aryl or heteroaryl,
or a pharmaceutically acceptable salt thereof.

In some embodiments, the compound
wherein R₁ is —C(=O)—NR₅R₆,
wherein
R₅ is

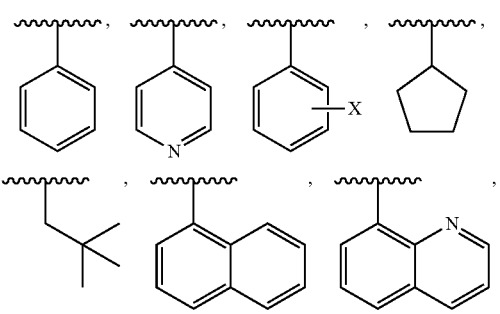

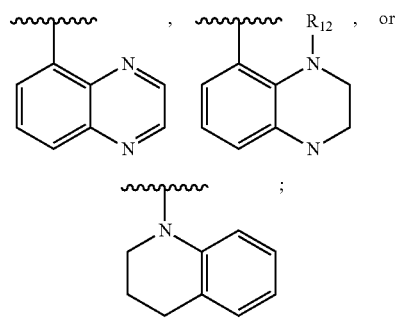

wherein
X is a Cl, Br, or F;
R₁₂ is H, C₁₋₅ alkyl, C₂₋₅ alkenyl, C₂₋₅ alkynyl, heteroalkyl, cycloalkyl, heterocycloalkyl, aryl, or heteroaryl; and
R₆ is H,

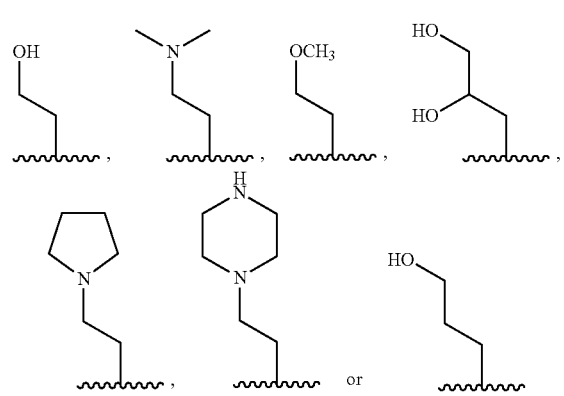

or a pharmaceutically acceptable salt thereof.

In some embodiments, the compound
wherein m=1;
R₂ is H or CH₃; and
R₃ is H, CH₃, Cl, Br, F, or CF₃;
or a pharmaceutically acceptable salt thereof.

In some embodiments, the compound
wherein R₆ is —NH—OR₁₁ or —OR₁₁,
wherein R₁₁ is H or CH₃,
or a pharmaceutically acceptable salt thereof.

In some embodiments, the compound
wherein R₁ is —C(=O)—NR₅R₆,
wherein R₅ and R₆ heteroalkyl, aryl, or heteroaryl;
m is 1;
R₂ and R₃ are H;
Ar₁ is phenyl;
Z is absent;
R₄ is —NH—OR₁₁,
wherein R₁₁ is H,
or a pharmaceutically acceptable salt thereof.

In some embodiments, the compound having the structure:
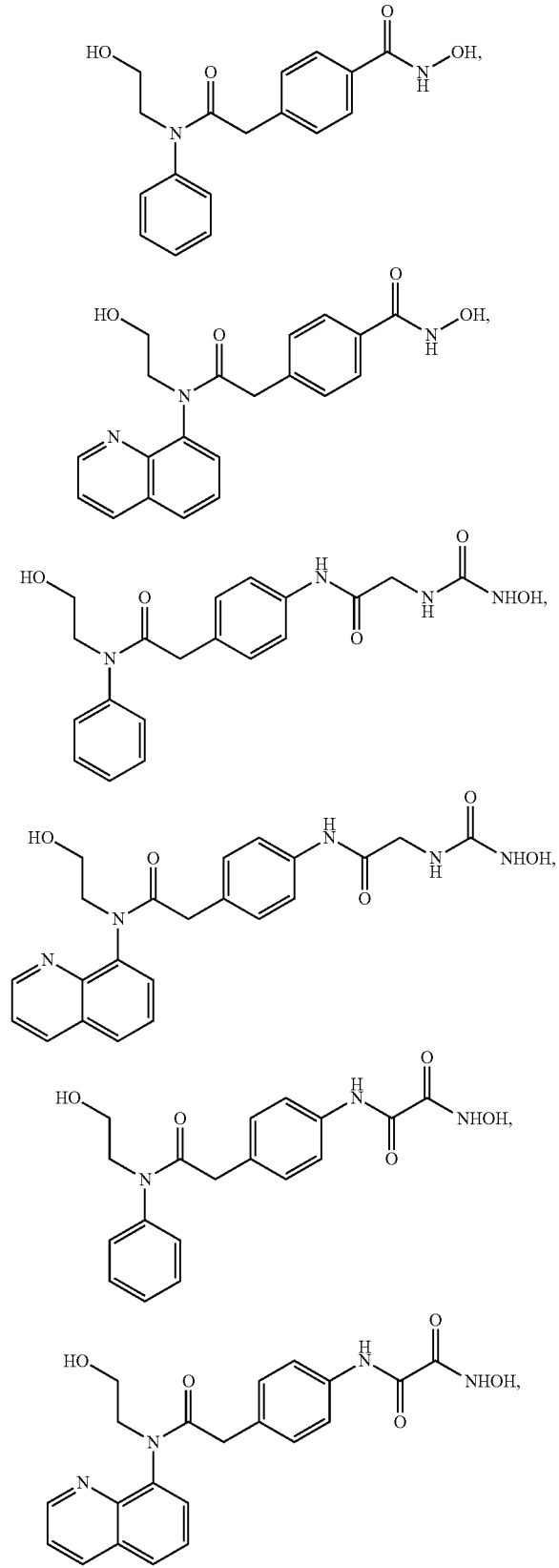
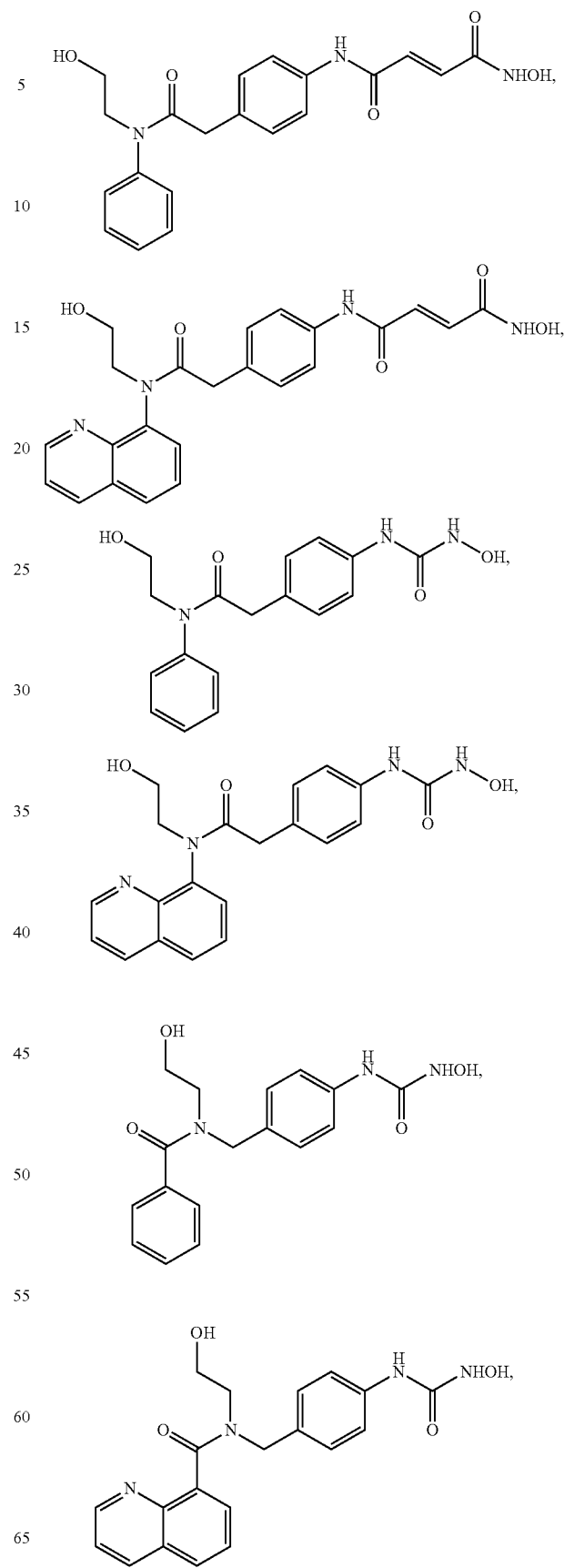

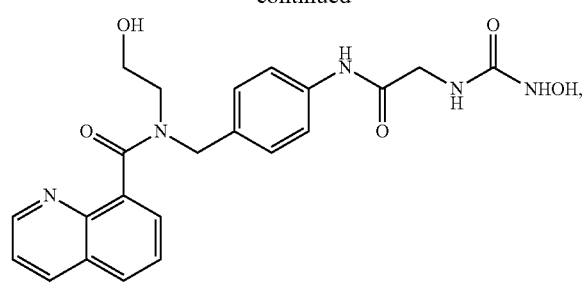
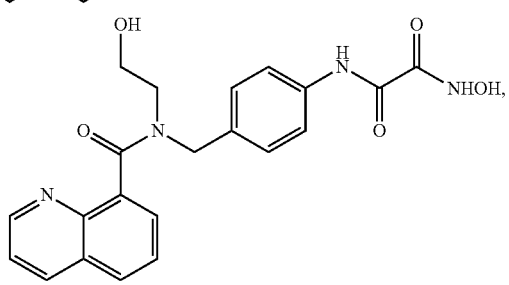
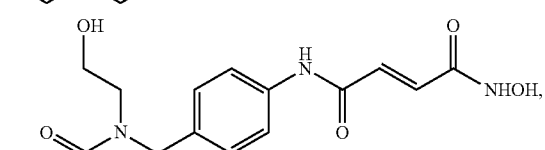
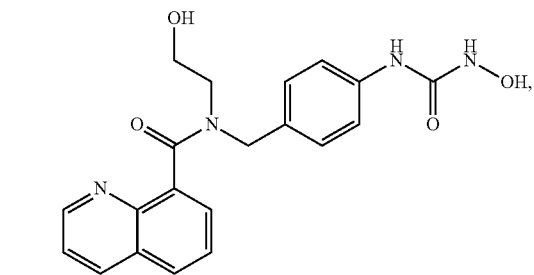
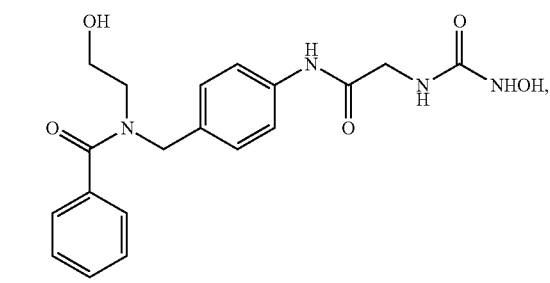
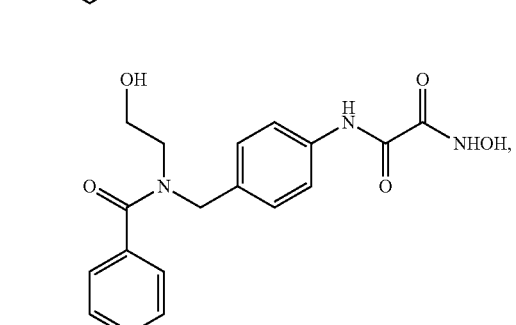
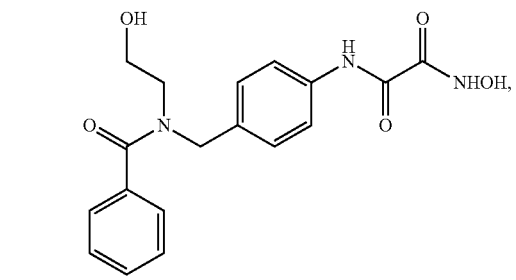
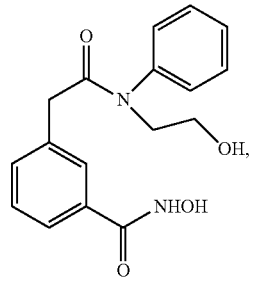
or a pharmaceutically acceptable salt thereof.
In some embodiments, the compound having the structure:
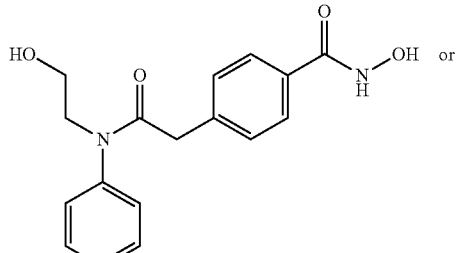
or a pharmaceutically acceptable salt thereof.
In some embodiments, the compound having the structure:
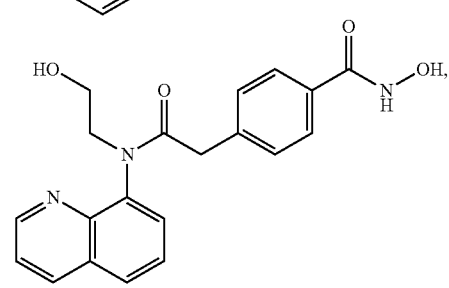
or a pharmaceutically acceptable salt thereof.

In some embodiments of the compound, n=1; $R_1$=H, $CH_3$, OH, $NH_2$ or F; and $R_2$ and
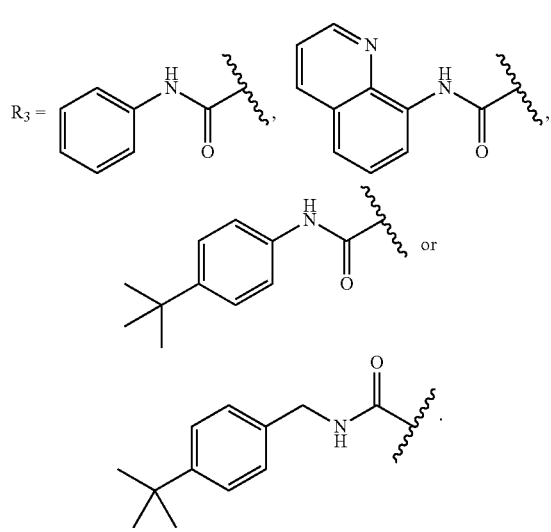
In some embodiments of the compound, n=0; and
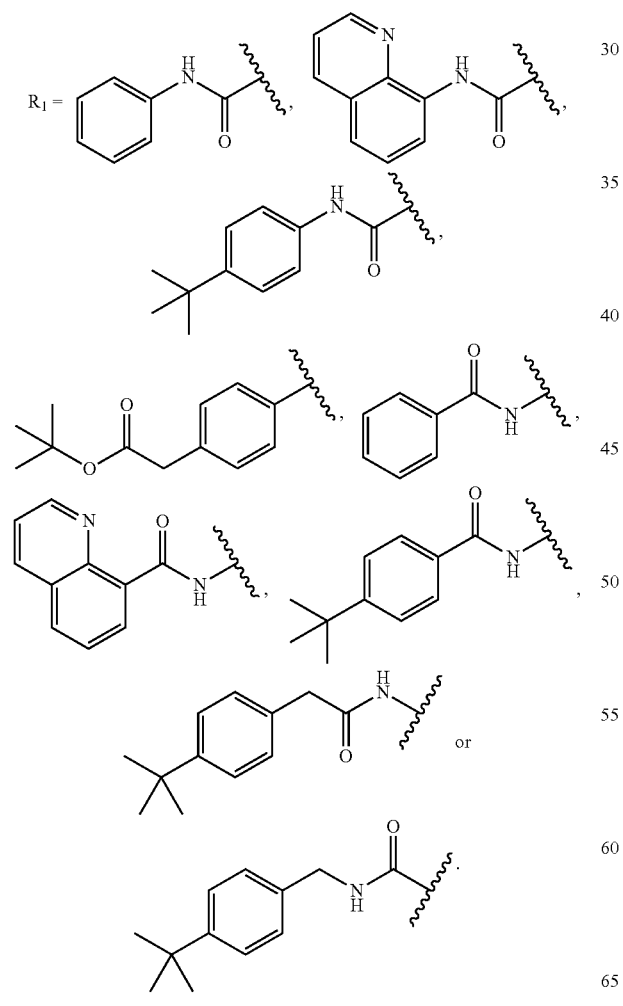
In some embodiments of the compound, n=1; $R_1$=H;
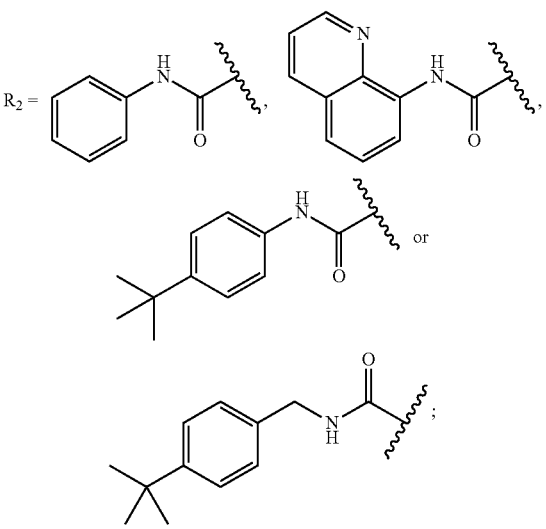
and $R_3$=$CH_3$, OH, $NH_2$ or F.
In some embodiments of the compound, n=1; $R_1$=H, $CH_3$, OH, $NH_2$ or F; and $R_2$ and
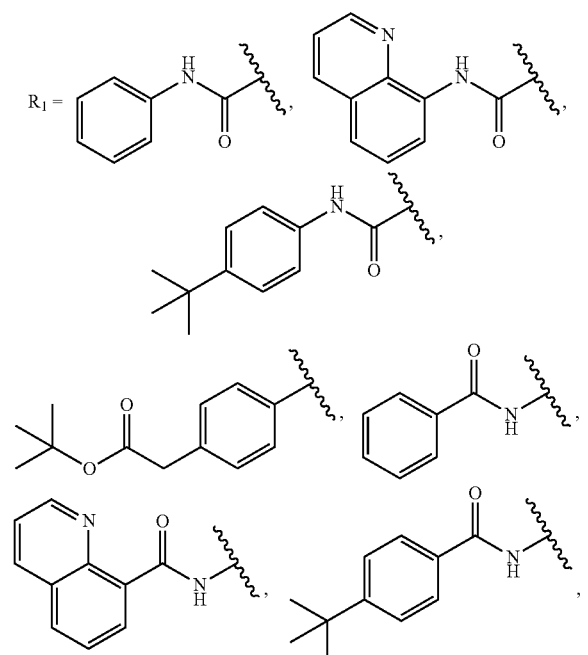
In some embodiments of the compound, n=1; $R_1$=H;
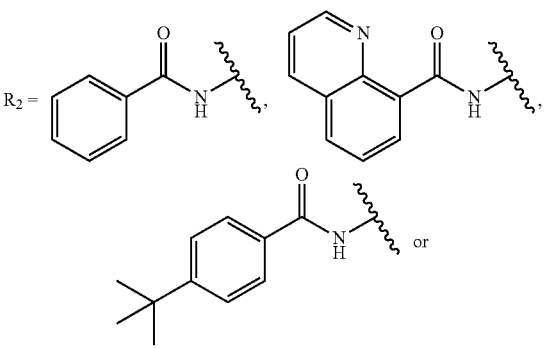

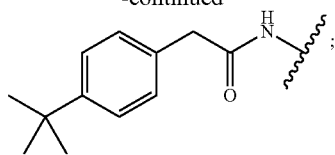
and R$_3$=CH$_3$, OH, NH$_2$ or F.
A pharmaceutical composition comprising any one, or more, of the instant compounds and a pharmaceutically acceptable carrier.
In some embodiments, the compound having the structure:
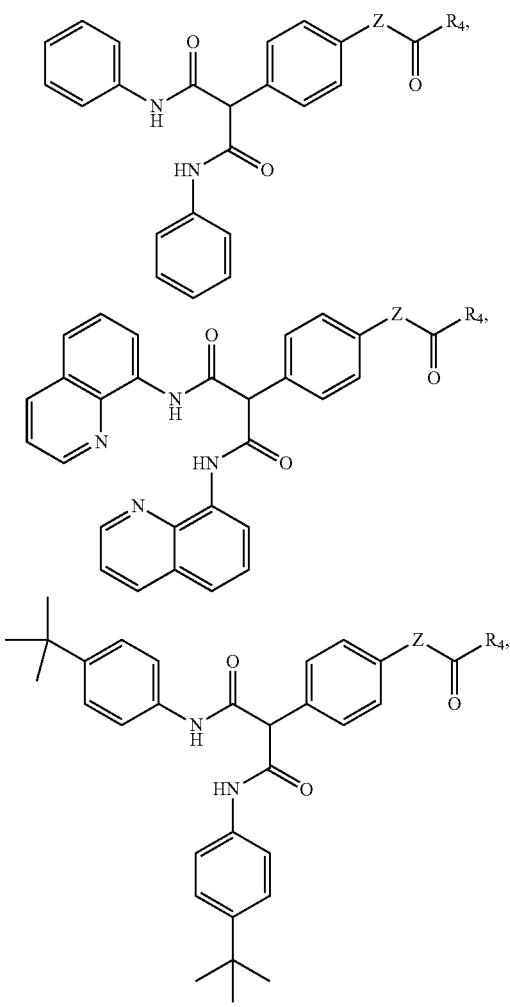
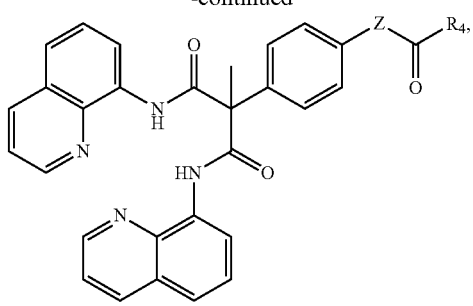
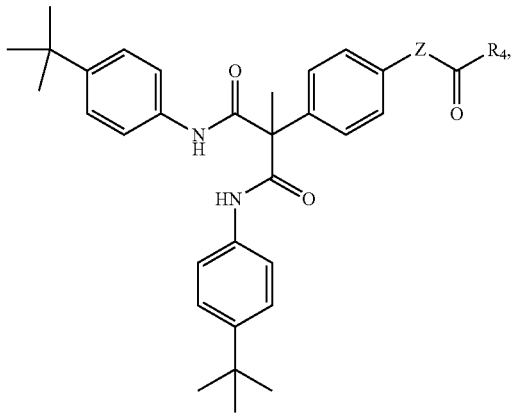
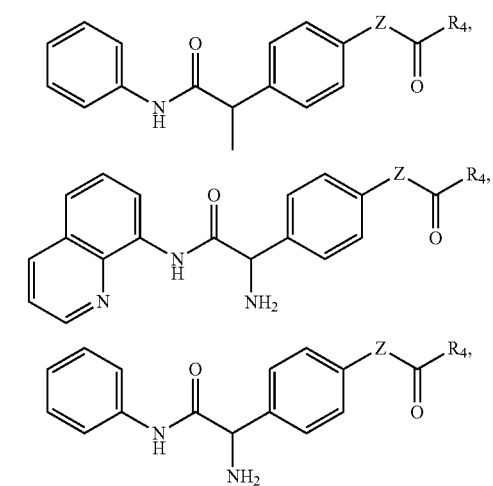
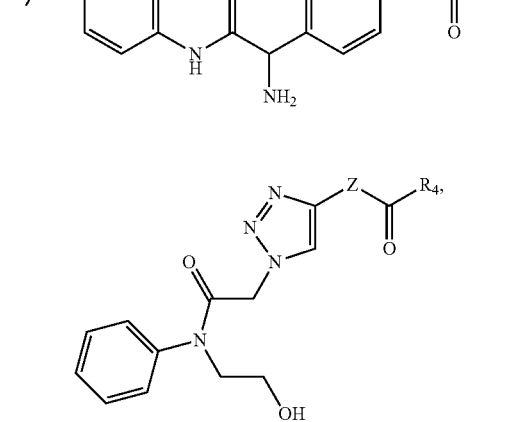

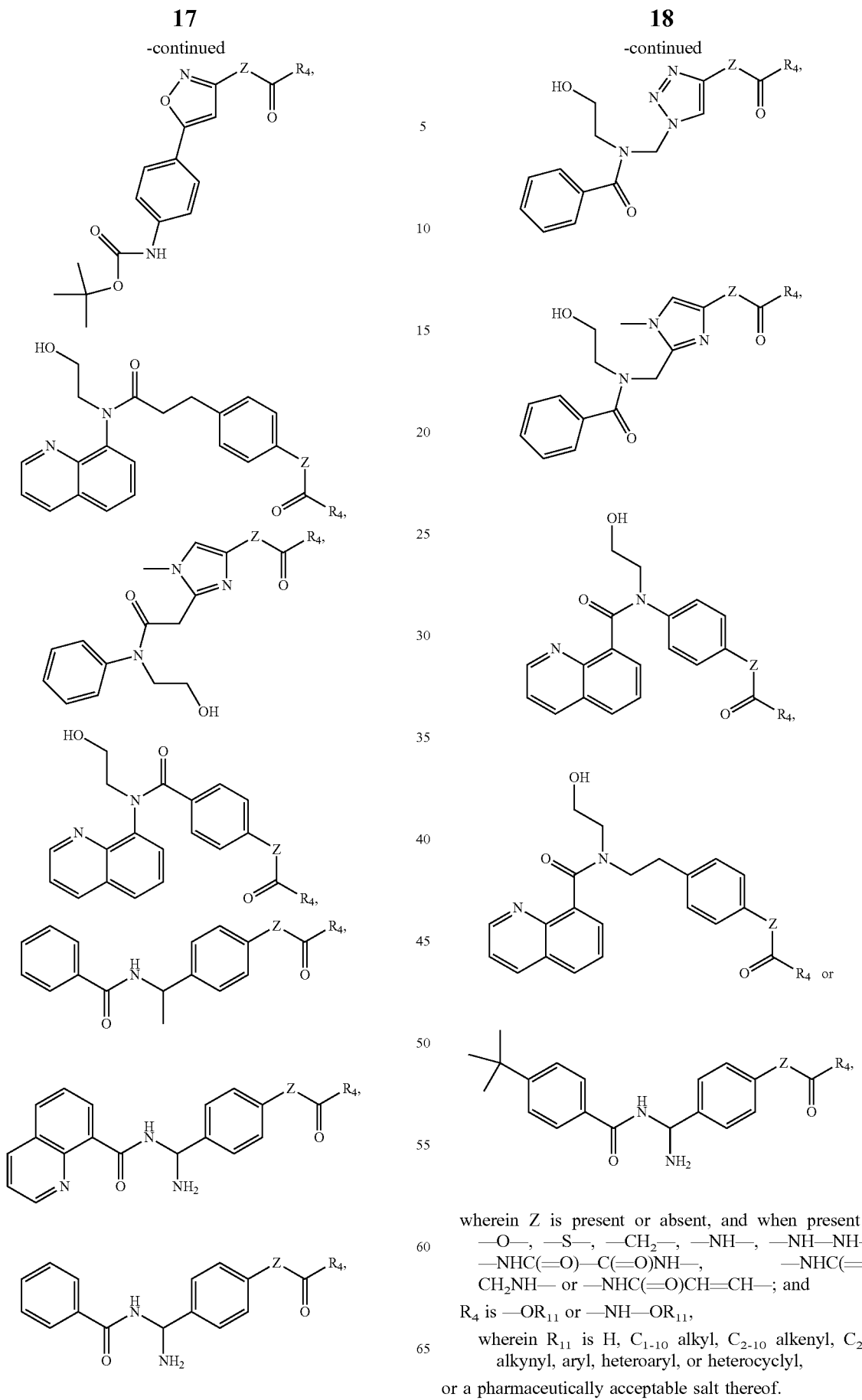
wherein Z is present or absent, and when present is —O—, —S—, —CH$_2$—, —NH—, —NH—NH—, —NHC(=O)—C(=O)NH—, —NHC(=O)CH$_2$NH— or —NHC(=O)CH=CH—; and
R$_4$ is —OR$_{11}$ or —NH—OR$_{11}$,
wherein R$_{11}$ is H, C$_{1-10}$ alkyl, C$_{2-10}$ alkenyl, C$_{2-10}$ alkynyl, aryl, heteroaryl, or heterocyclyl,
or a pharmaceutically acceptable salt thereof.

In some embodiments, the compound having the structure

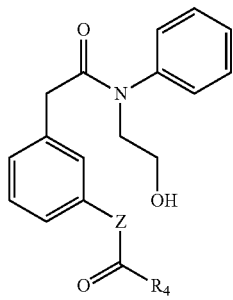

wherein Z is present or absent, and when present is —O—, —S—, —CH$_2$—, —NH—, —NH—NH—, —NHC(=O)—, —C(=O)NH—, —NHC(=O)CH$_2$NH— or —NHC(=O)CH=CH—; and R$_4$ is —OR$_{11}$ or —NH—OR$_{11}$, wherein R$_{11}$ is H, C$_{1-10}$ alkyl, C$_{2-10}$ alkenyl, C$_{2-10}$ alkynyl, aryl, heteroaryl, or heterocyclyl, or a pharmaceutically acceptable salt thereof.

In some embodiments, the compound wherein

Ar$_1$ is indole, benzimidazole, or tetralin, or a pharmaceutically acceptable salt thereof.

In some embodiments, the compound having the structure:

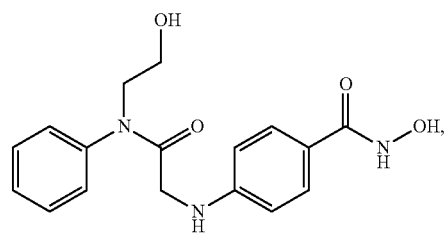

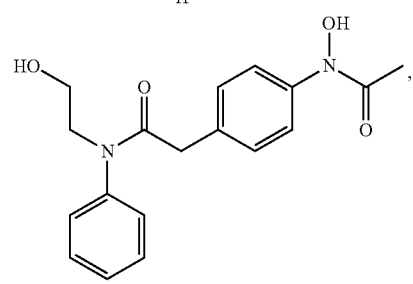

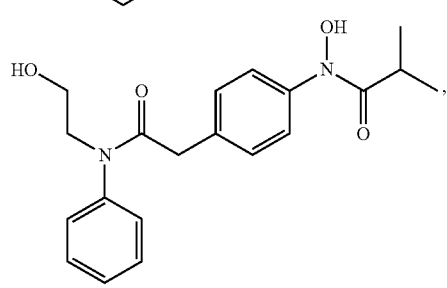

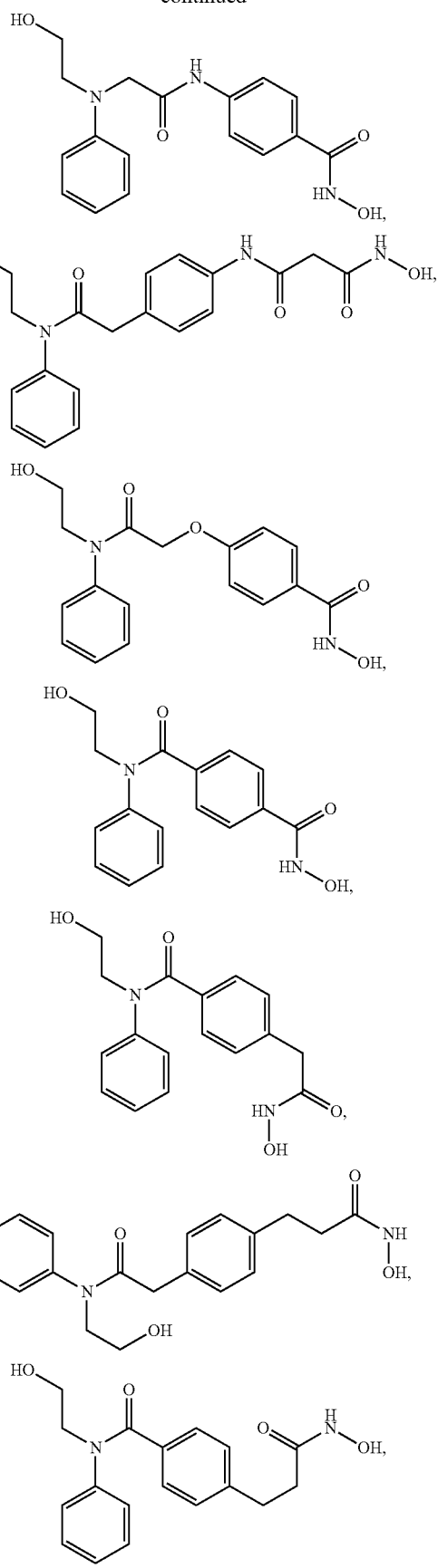

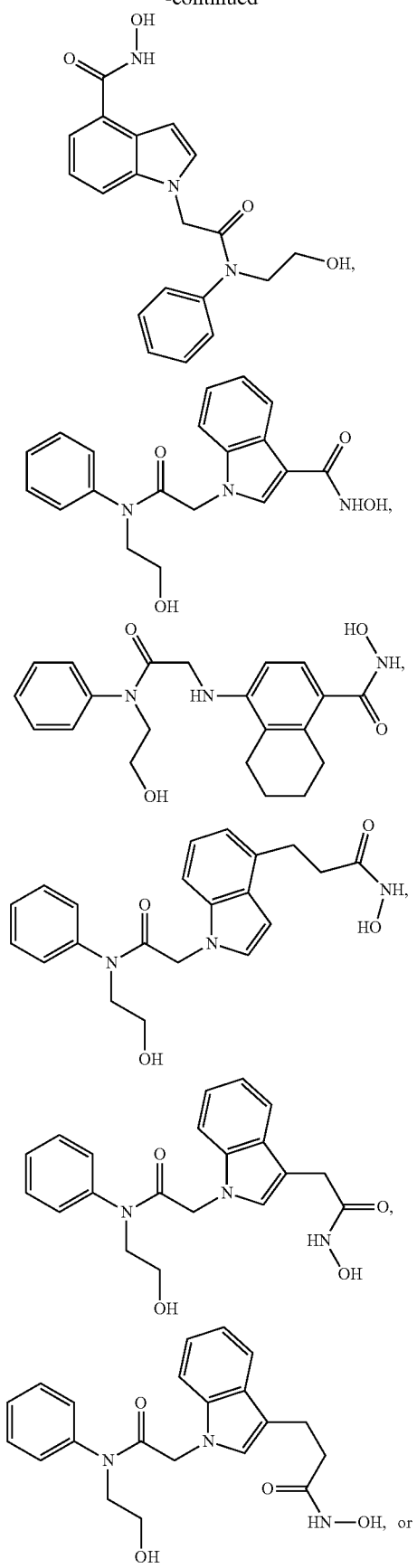

or a pharmaceutically acceptable salt thereof.

In some embodiments, a pharmaceutical composition comprising the compound of the present invention and a pharmaceutically acceptable carrier.

In some embodiments, a method of inhibiting the activity of a histone deactylase in a cell comprising contacting the histone deacetylase with the compound or composition of any one of the compounds of the present invention so as to inhibit the activity of the histone deacetylase.

In some embodiments, a method of inhibiting the activity of a histone deactylase wherein the histone deacetylase is HDAC6.

In some embodiments, a method of inhibiting the activity of a histone deacetylase 6 (HDAC6) in a cell comprising contacting the histone deacetylase 6 with the compound or composition of the present invention so as to inhibit the activity of the histone deacetylase 6 in the cell.

In some embodiments, a method of increasing accumulation of acetylated alpha tubulin in a cell comprising contacting the cell with any one of the compound or composition of the present invention so as to increase the accumulation of acetylated alpha-tubulin in the cell.

In some embodiments, a method of treating a neurodegenerative disease in a subject comprising administering an effective amount of the compound or composition of the present invention to the subject so as to treat the neurodegenerative disease in the subject.

In some embodiments, a method of treating a neurodegenerative disease wherein the neurodegenerative disease is Parkinson's disease, Alzheimer's disease, Huntington's disease or Niemann-Pick type C disease.

In some embodiments, a method of treating a disease associated with defective lipid transport in a subject comprising administering an effective amount of the compound or composition of the present invention to the subject so as to treat the disease in the subject.

In some embodiments, a method of treating a disease associated with defective lipid transport wherein the disease associated with defective lipid transport is Stargardt macular degeneration, Harlequin ichthyosis or Tangier disease.

A method of inhibiting the activity of a histone deactylase in a cell comprising contacting the histone deacetylase with any one, or more, of the instant compounds so as to inhibit the activity of the histone deacetylase.

In an embodiment the histone deacetylase is HDAC6.

A method of inhibiting the activity of a histone deacetylase 6 (HDAC6) in a cell comprising contacting the histone deacetylase 6 with any one, or more, of the instant compounds so as to inhibit the activity of the histone deacetylase 6 in the cell.

A method of increasing accumulation of acetylated alpha tubulin in a cell comprising contacting the cell with any one, or more, of the instant compounds so as to increase the accumulation of acetylated alpha-tubulin in the cell.

This invention also provides isotopic variants of the compounds disclosed herein, including wherein the isotopic atom is $^2$H and/or wherein the isotopic atom $^{13}$C. Accordingly, in the compounds provided herein hydrogen can be enriched in the deuterium isotope. It is to be understood that the invention encompasses all such isotopic forms which inhibit HDAC, including those which inhibit HDAC6 selectively over HDAC1.

A method of treating a neurodegenerative disease in a subject comprising administering an effective amount of any one, or more, of the instant compounds to the subject so as to treat the neurodegenerative disease in the subject.

In an embodiment, the neurodegenerative disease is Parkinson's disease, Alzheimer's disease, and Huntington's disease or Niemann-Pick type C disease.

A method of treating a disease associated with defective lipid transport in a subject comprising administering an effective amount of any one, or more, of the instant compounds to the subject so as to treat the disease in the subject.

In an embodiment, the disease associated with defective lipid transport is Stargardt macular degeneration, Harlequin ichthyosis or Tangier disease.

In some embodiments, the compounds of the instant invention for use in the treatment of cancer.

In some embodiments, the compounds of the instant invention for use in the treatment of a neurodegenerative disease.

In some embodiments, the compounds of the instant invention for use in the treatment of a disease associated with defective lipid transport.

In some embodiments, the compounds of the instant invention for use in inhibiting the activity of a histone deactylase in a cell.

In some embodiments, the compounds of the instant invention for use in inhibiting the activity of histone deactylase 6 in a cell.

In some embodiments, the compounds of the instant invention for use in increasing accumulation of acetylated alpha tubulin in a cell.

It is understood that the structures described in the embodiments of the methods hereinabove can be the same as the structures of the compounds described hereinabove.

It is understood that where a numerical range is recited herein, the present invention contemplates each integer between, and including, the upper and lower limits, unless otherwise stated.

As used herein, the term "activity" refers to the activation, production, expression, synthesis, intercellular effect, and/or pathological or aberrant effect of the referenced molecule, either inside and/or outside of a cell. Such molecules include, but are not limited to, cytokines, enzymes, growth factors, pro-growth factors, active growth factors, and pro-enzymes. Molecules such as cytokines, enzymes, growth factors, pro-growth factors, active growth factors, and pro-enzymes may be produced, expressed, or synthesized within a cell where they may exert an effect. Such molecules may also be transported outside of the cell to the extracellular matrix where they may induce an effect on the extracellular matrix or on a neighboring cell. It is understood that activation of inactive cytokines, enzymes and pro-enzymes may occur inside and/or outside of a cell and that both inactive and active forms may be present at any point inside and/or outside of a cell. It is also understood that cells may possess basal levels of such molecules for normal function and that abnormally high or low levels of such active molecules may lead to pathological or aberrant effects that may be corrected by pharmacological intervention.

As used herein, the term "histone deacetylase" or "HDAC" refers to any member of the classes of enzymes capable of cleaving an acetyl group (—C(=O)CH$_3$) from proteins, which include, but are not limited to, histones and microtubules. A histone deacetylase may be zinc-dependent. Examples of HDACs include, but are not limited to, HDAC1, HDAC2, HDAC3, HDAC4, HDAC5, HDAC6, HDAC7, HDAC8, HDAC9, HDAC10, and HDAC11.

Except where otherwise specified, the structure of a compound of this invention includes an asymmetric carbon atom, it is understood that the compound occurs as a racemate, racemic mixture, and isolated single enantiomer. All such isomeric forms of these compounds are expressly included in this invention. Except where otherwise specified, each stereogenic carbon may be of the R or S configuration. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis, such as those described in "Enantiomers, Racemates and Resolutions" by J. Jacques, A. Collet and S. Wilen, Pub. John Wiley & Sons, NY, 1981. For example, the resolution may be carried out by preparative chromatography on a chiral column.

The subject invention is also intended to include all isotopes of atoms occurring on the compounds disclosed herein. Isotopes include those atoms having the same atomic number but different mass numbers. By way of general example and without limitation, isotopes of hydrogen include tritium and deuterium. Isotopes of carbon include C-13 and C-14.

It will be noted that any notation of a carbon in structures throughout this application, when used without further notation, are intended to represent all isotopes of carbon, such as $^{12}$C, $^{13}$C, or $^{14}$C. Furthermore, any compounds containing $^{13}$C or $^{14}$C may specifically have the structure of any of the compounds disclosed herein.

It will also be noted that any notation of a hydrogen in structures throughout this application, when used without further notation, are intended to represent all isotopes of hydrogen, such as $^1$H, $^2$H, or $^3$H. Furthermore, any compounds containing $^2$H or $^3$H may specifically have the structure of any of the compounds disclosed herein.

Isotopically-labeled compounds can generally be prepared by conventional techniques known to those skilled in the art using appropriate isotopically-labeled reagents in place of the non-labeled reagents employed.

In the compounds used in the method of the present invention, the substituents may be substituted or unsubstituted, unless specifically defined otherwise.

In the compounds used in the method of the present invention, alkyl, heteroalkyl, monocycle, bicycle, aryl, heteroaryl and heterocycle groups can be further substituted by replacing one or more hydrogen atoms with alternative non-hydrogen groups. These include, but are not limited to, halo, hydroxy, mercapto, amino, carboxy, cyano and carbamoyl.

It is understood that substituents and substitution patterns on the compounds used in the method of the present invention can be selected by one of ordinary skill in the art to provide compounds that are chemically stable and that can be readily synthesized by techniques known in the art from readily available starting materials. If a substituent is itself substituted with more than one group, it is understood that these multiple groups may be on the same carbon or on different carbons, so long as a stable structure results.

In choosing the compounds used in the method of the present invention, one of ordinary skill in the art will recognize that the various substituents, i.e. $R_1$, $R_2$, etc. are to be chosen in conformity with well-known principles of chemical structure connectivity.

As used herein, "alkyl" includes both branched and straight-chain saturated aliphatic hydrocarbon groups having the specified number of carbon atoms and may be unsubstituted or substituted. Thus, $C_1$-$C_n$ as in "$C_1$-$C_n$ alkyl" is defined to include groups having 1, 2, . . . , n–1 or n carbons in a linear or branched arrangement. For example, $C_1$-$C_6$, as in "$C_1$-$C_6$ alkyl" is defined to include groups having 1, 2, 3, 4, 5, or 6 carbons in a linear or branched arrangement, and specifically includes methyl, ethyl, n-propyl, isopropyl, n-butyl, t-butyl, pentyl, hexyl, and octyl.

As used herein, "alkenyl" refers to a non-aromatic hydrocarbon radical, straight or branched, containing at least 1 carbon to carbon double bond, and up to the maximum possible number of non-aromatic carbon-carbon double bonds may be present, and may be unsubstituted or substituted. For example, "$C_2$-$C_6$ alkenyl" means an alkenyl radical having 2, 3, 4, 5, or 6 carbon atoms, and up to 1, 2, 3, 4, or 5 carbon-carbon double bonds respectively. Alkenyl groups include ethenyl, propenyl, butenyl and cyclohexenyl.

The term "alkynyl" refers to a hydrocarbon radical straight or branched, containing at least 1 carbon to carbon triple bond, and up to the maximum possible number of non-aromatic carbon-carbon triple bonds may be present, and may be unsubstituted or substituted. Thus, "$C_2$-$C_6$ alkynyl" means an alkynyl radical having 2 or 3 carbon atoms and 1 carbon-carbon triple bond, or having 4 or 5 carbon atoms and up to 2 carbon-carbon triple bonds, or having 6 carbon atoms and up to 3 carbon-carbon triple bonds. Alkynyl groups include ethynyl, propynyl and butynyl.

"Alkylene", "alkenylene" and "alkynylene" shall mean, respectively, a divalent alkane, alkene and alkyne radical, respectively. It is understood that an alkylene, alkenylene, and alkynylene may be straight or branched. An alkylene, alkenylene, and alkynylene may be unsubstituted or substituted.

As used herein, "aryl" is intended to mean any stable monocyclic, bicyclic or polycyclic carbon ring of up to 10 atoms in each ring, wherein at least one ring is aromatic, and may be unsubstituted or substituted. Examples of such aryl elements include phenyl, p-toluenyl (4-methylphenyl), naphthyl, tetrahydro-naphthyl, indanyl, biphenyl, phenanthryl, anthryl or acenaphthyl. In cases where the aryl substituent is bicyclic and one ring is non-aromatic, it is understood that attachment is via the aromatic ring.

As used herein, the term "polycyclic" refers to unsaturated or partially unsaturated multiple fused ring structures, which may be unsubstituted or substituted.

The term "arylalkyl" refers to alkyl groups as described above wherein one or more bonds to hydrogen contained therein are replaced by a bond to an aryl group as described above. It is understood that an "arylalkyl" group is connected to a core molecule through a bond from the alkyl group and that the aryl group acts as a substituent on the alkyl group. Examples of arylalkyl moieties include, but are not limited to, benzyl (phenylmethyl), p-trifluoromethylbenzyl (4-trifluoromethylphenylmethyl), 1-phenylethyl, 2-phenylethyl, 3-phenylpropyl, 2-phenylpropyl and the like.

The term "heteroaryl", as used herein, represents a stable monocyclic, bicyclic or polycyclic ring of up to 10 atoms in each ring, wherein at least one ring is aromatic and contains from 1 to 4 heteroatoms selected from the group consisting of O, N and S. Bicyclic aromatic heteroaryl groups include phenyl, pyridine, pyrimidine or pyridizine rings that are (a) fused to a 6-membered aromatic (unsaturated) heterocyclic ring having one nitrogen atom; (b) fused to a 5- or 6-membered aromatic (unsaturated) heterocyclic ring having two nitrogen atoms; (c) fused to a 5-membered aromatic (unsaturated) heterocyclic ring having one nitrogen atom together with either one oxygen or one sulfur atom; or (d) fused to a 5-membered aromatic (unsaturated) heterocyclic ring having one heteroatom selected from O, N or S. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrazolyl, tetrazolopyridyl, thiadiazolyl, thiazolyl, thienyl, triazolyl, azetidinyl, aziridinyl, 1,4-dioxanyl, hexahydroazepinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, tetrahydrothienyl, acridinyl, carbazolyl, cinnolinyl, quinoxalinyl, pyrrazolyl, indolyl, benzotriazolyl, benzothiazolyl, benzoxazolyl, isoxazolyl, isothiazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetra-hydroquinoline. In cases where the heteroaryl substituent is bicyclic and one ring is non-aromatic or contains no heteroatoms, it is understood that attachment is via the aromatic ring or via the heteroatom containing ring, respectively. If the heteroaryl contains nitrogen atoms, it is understood that the corresponding N-oxides thereof are also encompassed by this definition.

The term "heterocycle", "heterocyclyl" or "heterocyclic" refers to a mono- or poly-cyclic ring system which can be saturated or contains one or more degrees of unsaturation and contains one or more heteroatoms. Preferred heteroatoms include N, O, and/or S, including N-oxides, sulfur oxides, and dioxides. Preferably the ring is three to ten-membered and is either saturated or has one or more degrees of unsaturation. The heterocycle may be unsubstituted or substituted, with multiple degrees of substitution being allowed. Such rings may be optionally fused to one or more of another "heterocyclic" ring(s), heteroaryl ring(s), aryl ring(s), or cycloalkyl ring(s). Examples of heterocycles include, but are not limited to, tetrahydrofuran, pyran, 1,4-dioxane, 1,3-dioxane, piperidine, piperazine, pyrrolidine, morpholine, thiomorpholine, tetrahydrothiopyran, tetrahydrothiophene, 1,3-oxathiolane, and the like.

The alkyl, alkenyl, alkynyl, aryl, heteroaryl and heterocyclyl substituents may be substituted or unsubstituted, unless specifically defined otherwise.

In the compounds of the present invention, alkyl, alkenyl, alkynyl, aryl, heterocyclyl and heteroaryl groups can be further substituted by replacing one or more hydrogen atoms with alternative non-hydrogen groups. These include, but are not limited to, halo, hydroxy, mercapto, amino, carboxy, cyano and carbamoyl.

As used herein, the term "halogen" refers to F, Cl, Br, and I.

As used herein, "heteroalkyl" includes both branched and straight-chain saturated aliphatic hydrocarbon groups having the specified number of carbon atoms and at least 1 heteroatom within the chain or branch.

As used herein, "monocycle" includes any stable polyatomic carbon ring of up to 10 atoms and may be unsubstituted or substituted. Examples of such non-aromatic monocycle elements include but are not limited to: cyclobutyl, cyclopentyl, cyclohexyl, and cycloheptyl. Examples of such aromatic monocycle elements include but are not limited to: phenyl.

As used herein, "bicycle" includes any stable polyatomic carbon ring of up to 10 atoms that is fused to a polyatomic carbon ring of up to 10 atoms with each ring being independently unsubstituted or substituted. Examples of such non-aromatic bicycle elements include but are not limited to: decahydronaphthalene. Examples of such aromatic bicycle elements include but are not limited to: naphthalene.

The term "ester" is intended to a mean an organic compound containing the R—O—CO—R' group.

The term "amide" is intended to a mean an organic compound containing the R—CO—NH—R' or R—CO—N—R'R" group.

The term "phenyl" is intended to mean an aromatic six membered ring containing six carbons.

The term "biphenyl" is intended to mean an aryl comprising two benzene rings linked together, and any substituted derivative thereof.

The term "pyrrole" is intended to mean a heteroaryl having a five-membered ring containing four carbon atoms and one nitrogen atom.

The term "furan" is intended to mean a heteroaryl having a five-membered ring containing four carbon atoms and one oxygen atom.

The term "thiophene" is intended to mean a heteroaryl having a five-membered ring containing four carbon atoms and one sulfur atom.

The term "quinoline" is intended to mean a fully aromatic heteroaryl having a six-membered ring fused to a six-membered ring containing nine carbon atoms and one nitrogen atom.

The term "carbazole" is intended to mean a fully aromatic heteroaryl having two six-membered benzene rings fused both sides of a five-membered nitrogen-containing ring.

The terms "tetrahydrocarboline", "tetrahydro-β-carboline" and "tetrahydro-γ-carboline" are intended to mean an aryl having a six-membered ring fused to a five membered ring which in turn is fused to a piperidine ring with a total of 11 carbon atoms and 2 nitrogen atoms with the five-membered ring containing 1 nitrogen atom and the piperidine ring containing 1 nitrogen atom and any substituted derivative thereof.

The term "benzimidazole" is intended to mean a heteroaryl having a five-membered ring fused to a phenyl ring with the five-membered ring containing 2 nitrogen atoms directly attached to the phenyl ring.

The term "indole" is intended to mean a heteroaryl having a five-membered ring fused to a phenyl ring with the five-membered ring containing 1 nitrogen atom directly attached to the phenyl ring.

The term "tetralin" is intended to mean a bicycle wherein an aromatic phenyl ring is fused to a non-aromatic cyclohexyl ring.

The term "substitution", "substituted" and "substituent" refers to a functional group as described above in which one or more bonds to a hydrogen atom contained therein are replaced by a bond to non-hydrogen or non-carbon atoms, provided that normal valencies are maintained and that the substitution results in a stable compound. Substituted groups also include groups in which one or more bonds to a carbon(s) or hydrogen(s) atom are replaced by one or more bonds, including double or triple bonds, to a heteroatom. Examples of substituent groups include the functional groups described above, and halogens (i.e., F, Cl, Br, and I); alkyl groups, such as methyl, ethyl, n-propyl, isopropyl, n-butyl, tert-butyl, and trifluoromethyl; hydroxyl; alkoxy groups, such as methoxy, ethoxy, n-propoxy, and iso-propoxy; aryloxy groups, such as phenoxy; arylalkyloxy, such as benzyloxy (phenylmethoxy) and p-trifluoromethyl-benzyloxy (4-trifluoromethylphenylmethoxy); heteroaryloxy groups; sulfonyl groups, such as trifluoromethanesulfonyl, methanesulfonyl, and p-toluenesulfonyl; nitro, nitrosyl; mercapto; sulfanyl groups, such as methylsulfanyl, ethylsulfanyl and propylsulfanyl; cyano; amino groups, such as amino, methylamino, dimethylamino, ethylamino, and diethylamino; and carboxyl. Where multiple substituent moieties are disclosed or claimed, the substituted compound can be independently substituted by one or more of the disclosed or claimed substituent moieties, singly or plurally. By independently substituted, it is meant that the (two or more) substituents can be the same or different.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

In choosing the compounds of the present invention, one of ordinary skill in the art will recognize that the various substituents, i.e. $R_1$, $R_2$, etc. are to be chosen in conformity with well-known principles of chemical structure connectivity.

The various R groups attached to the aromatic rings of the compounds disclosed herein may be added to the rings by standard procedures, for example those set forth in Advanced Organic Chemistry: Part B: Reaction and Synthesis, Francis Carey and Richard Sundberg, (Springer) 5th ed. Edition. (2007), the content of which is hereby incorporated by reference.

The compounds used in the method of the present invention may be prepared by techniques well know in organic synthesis and familiar to a practitioner ordinarily skilled in the art. However, these may not be the only means by which to synthesize or obtain the desired compounds.

The compounds used in the method of the present invention may be prepared by techniques described in Vogel's Textbook of Practical Organic Chemistry, A. I. Vogel, A. R. Tatchell, B. S. Furnis, A. J. Hannaford, P. W. G. Smith, (Prentice Hall) $5^{th}$ Edition (1996), March's Advanced Organic Chemistry: Reactions, Mechanisms, and Structure, Michael B. Smith, Jerry March, (Wiley-Interscience) $5^{th}$ Edition (2007), and references therein, which are incorporated by reference herein. However, these may not be the only means by which to synthesize or obtain the desired compounds.

Another aspect of the invention comprises a compound used in the method of the present invention as a pharmaceutical composition.

As used herein, the term "pharmaceutically active agent" means any substance or compound suitable for administration to a subject and furnishes biological activity or other direct effect in the treatment, cure, mitigation, diagnosis, or prevention of disease, or affects the structure or any function of the subject.

Pharmaceutically active agents include, but are not limited to, substances and compounds described in the Physicians' Desk Reference (PDR Network, LLC; 64th edition; Nov. 15, 2009) and "Approved Drug Products with Therapeutic Equivalence Evaluations" (U.S. Department Of Health And Human Services, $30^{th}$ edition, 2010), which are hereby incorporated by reference. Pharmaceutically active agents which have pendant carboxylic acid groups may be modified in accordance with the present invention using standard esterification reactions and methods readily available and known to those having ordinary skill in the art of chemical synthesis. Where a pharmaceutically active agent does not possess a carboxylic acid group, the ordinarily skilled artisan will be able to design and incorporate a carboxylic acid group into the pharmaceutically active agent where esterification may subsequently be carried out so long as the modification does not interfere with the pharmaceutically active agent's biological activity or effect.

The compounds used in the method of the present invention may be in a salt form. As used herein, a "salt" is a salt of the instant compounds which has been modified by making acid or base salts of the compounds. In the case of compounds used to treat an infection or disease caused by a pathogen, the salt is pharmaceutically acceptable. Examples of pharmaceutically acceptable salts include, but are not limited to, mineral or organic acid salts of basic residues such as amines; alkali or organic salts of acidic residues such as phenols. The salts can be made using an organic or inorganic acid. Such acid salts are chlorides, bromides, sulfates, nitrates, phosphates, sulfonates, formates, tartrates, maleates, malates, citrates, benzoates, salicylates, ascorbates, and the like. Phenolate salts are the alkaline earth metal salts, sodium, potassium or lithium. The term "pharmaceutically acceptable salt" in this respect, refers to the relatively non-toxic, inorganic and organic acid or base addition salts of compounds of the present invention. These salts can be prepared in situ during the final isolation and purification of the compounds of the invention, or by separately reacting a purified compound of the invention in its free base or free acid form with a suitable organic or inorganic acid or base, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1-19).

As used herein, "treating" means preventing, slowing, halting, or reversing the progression of a disease or infection. Treating may also mean improving one or more symptoms of a disease or infection.

The compounds used in the method of the present invention may be administered in various forms, including those detailed herein. The treatment with the compound may be a component of a combination therapy or an adjunct therapy, i.e. the subject or patient in need of the drug is treated or given another drug for the disease in conjunction with one or more of the instant compounds. This combination therapy can be sequential therapy where the patient is treated first with one drug and then the other or the two drugs are given simultaneously. These can be administered independently by the same route or by two or more different routes of administration depending on the dosage forms employed.

As used herein, a "pharmaceutically acceptable carrier" is a pharmaceutically acceptable solvent, suspending agent or vehicle, for delivering the instant compounds to the animal or human. The carrier may be liquid or solid and is selected with the planned manner of administration in mind. Liposomes are also a pharmaceutically acceptable carrier.

The dosage of the compounds administered in treatment will vary depending upon factors such as the pharmacodynamic characteristics of a specific chemotherapeutic agent and its mode and route of administration; the age, sex, metabolic rate, absorptive efficiency, health and weight of the recipient; the nature and extent of the symptoms; the kind of concurrent treatment being administered; the frequency of treatment with; and the desired therapeutic effect.

A dosage unit of the compounds used in the method of the present invention may comprise a single compound or mixtures thereof with additional antibacterial agents. The compounds can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by injection, topical application, or other methods, into or onto a site of infection, all using dosage forms well known to those of ordinary skill in the pharmaceutical arts.

The compounds used in the method of the present invention can be administered in admixture with suitable pharmaceutical diluents, extenders, excipients, or carriers (collectively referred to herein as a pharmaceutically acceptable carrier) suitably selected with respect to the intended form of administration and as consistent with conventional pharmaceutical practices. The unit will be in a form suitable for oral, rectal, topical, intravenous or direct injection or parenteral administration. The compounds can be administered alone or mixed with a pharmaceutically acceptable carrier. This carrier can be a solid or liquid, and the type of carrier is generally chosen based on the type of administration being used. The active agent can be co-administered in the form of a tablet or capsule, liposome, as an agglomerated powder or in a liquid form. Examples of suitable solid carriers include lactose, sucrose, gelatin and agar. Capsule or tablets can be easily formulated and can be made easy to swallow or chew; other solid forms include granules, and bulk powders. Tablets may contain suitable binders, lubricants, diluents, disintegrating agents, coloring agents, flavoring agents, flow-inducing agents, and melting agents. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents. Oral dosage forms optionally contain flavorants and coloring agents. Parenteral and intravenous forms may also include minerals and other materials to make them compatible with the type of injection or delivery system chosen.

Techniques and compositions for making dosage forms useful in the present invention are described in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol. 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.). All of the aforementioned publications are incorporated by reference herein.

Tablets may contain suitable binders, lubricants, disintegrating agents, coloring agents, flavoring agents, flow-inducing agents, and melting agents. For instance, for oral administration in the dosage unit form of a tablet or capsule, the active drug component can be combined with an oral, non-toxic, pharmaceutically acceptable, inert carrier such as lactose, gelatin, agar, starch, sucrose, glucose, methyl cellulose, magnesium stearate, dicalcium phosphate, calcium sulfate, mannitol, sorbitol and the like. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds used in the method of the present invention may also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines. The compounds may be administered as components of tissue-targeted emulsions.

The compounds used in the method of the present invention may also be coupled to soluble polymers as targetable drug carriers or as a prodrug. Such polymers include polyvinylpyrrolidone, pyran copolymer, polyhydroxylpropyl-methacrylamide-phenol, polyhydroxyethylasparta-midephenol, or polyethyleneoxide-polylysine substituted with palmitoyl residues. Furthermore, the compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates, and crosslinked or amphipathic block copolymers of hydrogels.

Gelatin capsules may contain the active ingredient compounds and powdered carriers, such as lactose, starch, cellulose derivatives, magnesium stearate, stearic acid, and the like. Similar diluents can be used to make compressed tablets. Both tablets and capsules can be manufactured as immediate release products or as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

For oral administration in liquid dosage form, the oral drug components are combined with any oral, non-toxic, pharmaceutically acceptable inert carrier such as ethanol, glycerol, water, and the like. Examples of suitable liquid dosage forms include solutions or suspensions in water, pharmaceutically acceptable fats and oils, alcohols or other organic solvents, including esters, emulsions, syrups or elixirs, suspensions, solutions and/or suspensions reconstituted from non-effervescent granules and effervescent preparations reconstituted from effervescent granules. Such liquid dosage forms may contain, for example, suitable solvents, preservatives, emulsifying agents, suspending agents, diluents, sweeteners, thickeners, and melting agents.

Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. Suitable pharmaceutical carriers are described in Remington's Pharmaceutical Sciences, Mack Publishing Company, a standard reference text in this field.

The compounds used in the method of the present invention may also be administered in intranasal form via use of suitable intranasal vehicles, or via transdermal routes, using those forms of transdermal skin patches well known to those of ordinary skill in that art. To be administered in the form of a transdermal delivery system, the dosage administration will generally be continuous rather than intermittent throughout the dosage regimen.

Parenteral and intravenous forms may also include minerals and other materials to make them compatible with the type of injection or delivery system chosen.

The compounds and compositions of the present invention can be administered in oral dosage forms as tablets, capsules, pills, powders, granules, elixirs, tinctures, suspensions, syrups, and emulsions. The compounds may also be administered in intravenous (bolus or infusion), intraperitoneal, subcutaneous, or intramuscular form, or introduced directly, e.g. by topical administration, injection or other methods, to the afflicted area, such as a wound, including ulcers of the skin, all using dosage forms well known to those of ordinary skill in the pharmaceutical arts.

Specific examples of pharmaceutical acceptable carriers and excipients that may be used to formulate oral dosage forms of the present invention are described in U.S. Pat. No. 3,903,297 to Robert, issued Sep. 2, 1975. Techniques and compositions for making dosage forms useful in the present invention are described—in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modem Pharmaceutics Drugs and the Pharmaceutical Sciences, Vol 40 (Gilbert S. Banker, Christopher T. Rhodes, Eds.). All of the aforementioned publications are incorporated by reference herein.

The term "prodrug" as used herein refers to any compound that when administered to a biological system generates the compound of the invention, as a result of spontaneous chemical reaction(s), enzyme catalyzed chemical reaction(s), photolysis, and/or metabolic chemical reaction(s). A prodrug is thus a covalently modified analog or latent form of a compound of the invention.

The active ingredient can be administered orally in solid dosage forms, such as capsules, tablets, powders, and chewing gum; or in liquid dosage forms, such as elixirs, syrups, and suspensions, including, but not limited to, mouthwash and toothpaste. It can also be administered parentally, in sterile liquid dosage forms.

Solid dosage forms, such as capsules and tablets, may be enteric coated to prevent release of the active ingredient compounds before they reach the small intestine. Materials that may be used as enteric coatings include, but are not limited to, sugars, fatty acids, waxes, shellac, cellulose acetate phthalate (CAP), methyl acrylate-methacrylic acid copolymers, cellulose acetate succinate, hydroxy propyl methyl cellulose phthalate, hydroxy propyl methyl cellulose acetate succinate (hypromellose acetate succinate), polyvinyl acetate phthalate (PVAP), and methyl methacrylate-methacrylic acid copolymers.

The compounds and compositions of the invention can be coated onto stents for temporary or permanent implantation into the cardiovascular system of a subject.

The compounds of the present invention can be synthesized according to general Schemes. Variations on the following general synthetic methods will be readily apparent to those skilled in the art and are deemed to be within the scope of the present invention.

Each embodiment disclosed herein is contemplated as being applicable to each of the other disclosed embodiments. Thus, all combinations of the various elements described herein are within the scope of the invention.

This invention will be better understood by reference to the Experimental Details which follow, but those skilled in the art will readily appreciate that the specific experiments detailed are only illustrative of the invention as described more fully in the claims which follow thereafter.

EXPERIMENTAL DETAILS

8-Aminoquinoline, aniline, glycolaldehyde dimer, sodium triacetoxyborohydride, tert-butylchlorodimethylsilane (TBDMS-Cl), potassium cyanide, $NH_2OH$, trifluoroacetic acid (TFA), dichloroethane (DCE), dichloromethne (DCM), 1-Ethyl-3-(3-dimethyllaminopropyl)carbodiimide hydrochloride (EDC), sodium sulfate (anhydrous), calcium hypochlorite, molecular sieves (4 Å), $NH_4Cl$, NaCl, MeOH, $NaHCO_3$, THF, hydrochloric acid, acetic acid, $CDCl_3$, $CD_3OD$, and hexanes were used as received without further purification. Purification of product mixtures was carried out by column using silica gel with 40-60 Å particle size or preparative chromatography using silica gel 60F 254 TLC-plates. TLC was carried out using silica gel 60F 254 TLC-plates. Proton NMR data were acquired at 400 MHz and $^{13}C$ NMR data were acquired at 100.6 MHz.

Those having ordinary skill in the art of organic synthesis will appreciate that modifications to general procedures and synthetic routes contained in this application can be used to yield additional derivatives and structurally diverse compounds. Suitable organic transformations are described in March's Advanced Organic Chemistry: Reactions, Mechanisms, and Structure (Wiley-Interscience; $6^{th}$ edition, 2007), the content of which is hereby incorporated by reference.

Example 1

Synthesis of Compound 6

HDAC inhibitor 6 was accessed according to the protocols shown in Scheme 1. Alcohol 2 was prepared by treatment of aniline 1 with glycolaldehyde followed by addition of sodium triacetoxyborohydride. The alcohol 2 was then protected with TBDMSCl followed by EDC coupling with acid 8 (Scheme 2). The methyl ester 4 was converted directly, using a catalytic amount of KCN, to the corresponding hydroxamic acid 5, which was deprotected with TFA to afford compound 6.

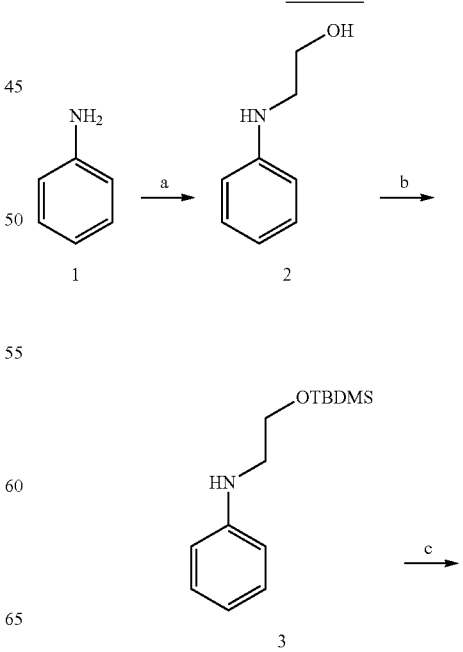

-continued

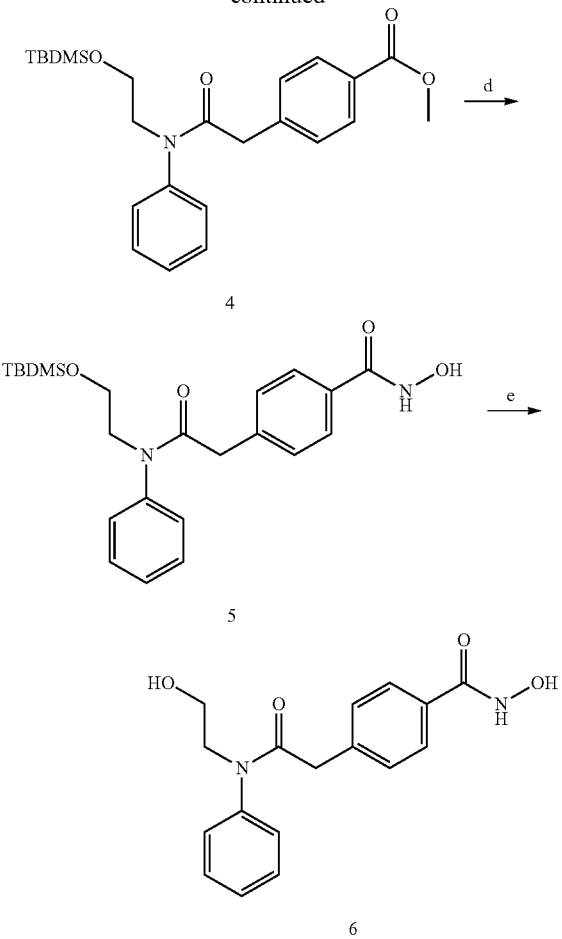

Reagents: (a) 1. HOCH₂CHO, DCE, 30 min. rt. 2. NaBH(OAc)₃, 4 h. rt. (b) TBDMS-Cl, DCM, 3 h. (c) 8, EDC, DCM, rt. 24 h. (d) NH₂OH, THF:MeOH (1:1), KCN (cat.) 16 h, rt. (e) 5% TFA in DCM, 5 min Scheme 2.

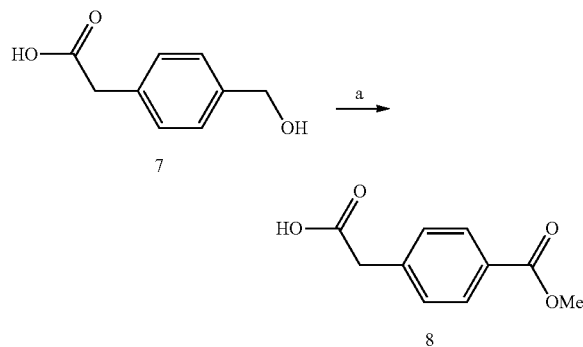

Reagents: (a) Ca(OCl)₂, HOAc, ACN, MeOH, molecular sieves, dark, 48 hr, rt 2-(phenylamino)ethanol (2)

Glycolaldehyde (645 mg, 10.7 mmol) was added to a solution containing aniline (1, 1.00 g, 10.7 mmol) in DCE (30 mL). The solution was stirred at room temperature in argon atmosphere for 30 min. Sodium triacetoxyborohydride (2.61 g, 12.3 mmol) was then added portion-wise. The reaction mixture was further stirred for 4 h before and quenched with NaHCO₃ to pH=9.0. The reaction mixture was extracted with mixed solvent (CH₂Cl₃:i-PrOH=4:1, 30 mL×3). The organic layer was dried (anhydrous sodium sulfate) and concentrated in vacuo. The crude product was chromatographed on silica gel (CH₂Cl₂/MeOH, 20:1) to yield target compound 2. Yield 1.061 g, 72%. $R_f$=0.45, ¹H NMR (CHCl₃, 400 MHz): δ 7.24 (dd, J=8.8, 7.4 Hz, 2H), 6.80 (t, J=7.4 Hz, 1H), 6.69 (d, J=8.8, 2H), 3.81 (t, J=5.2 Hz, 2H), 3.30 (t, J=5.2 Hz, 2H), 2.6 (br s, 1H); ¹³C NMR (CHCl₃, 100 MHz): δ 148.2, 129.4, 118.0, 113.3, 61.2, 46.1; [M+H]⁺=138.08 (APCI+).

N-(2-((tert-butyldimethylsilyl)oxy)ethyl)aniline (3)

TBDMS-Cl (1.28 g, 8.02 mmol) and imidazole (1.45 g, 21.86 mmol) was added to a solution containing 2-(phenylamino)ethanol 2, (1.00 g, 7.29 mmol) in CH₂Cl₂ (10 mL). The reaction mixture was stirred at room temperature in argon atmosphere for 3 h. Then the reaction was quenched with sat. NH₄Cl. and washed with water (10 mL×2) and brine (10 mL×2). The organic layer was dried (anhydrous sodium sulfate) and concentrated in vacuo. The crude product was chromatographed on silica gel (Hexanes/EtOAc, 7:1) to yield target compound 3. Yield 1.689 g, 92%. $R_f$=0.60, ¹H NMR (CHCl₃, 400 MHz): δ 7.22 (dd, J=8.8, 7.4 Hz, 2H), 6.76 (t, J=7.4 Hz, 1H), 6.68 (d, J=8.8, 2H), 4.09 (br s, 1H), 3.86 (t, J=5.2 Hz, 2H), 3.26 (t, J=5.2 Hz, 2H), 0.95 (s, 9H), 0.11 (s, 6H); ¹³C NMR (CHCl₃, 100 MHz): δ 148.4, 129.2, 117.5, 113.2, 61.6, 46.0, 25.9, 18.3, −5.3; [M+H]⁺=252.12 (APCI+).

Methyl 4-(2-((2-((tert-butyldimethylsilyl)oxy)ethyl)(phenyl)amino)-2-oxoethyl)benzoate (4)

EDC (114.5 mg, 0.597 mmol) was added to a solution containing N-(2-((tert-butyldimethylsilyl)oxy)ethyl)aniline 3 (100 mg, 0.398 mmol) and 2-(4-(methoxycarbonyl)phenyl)acetic acid, 8, (116 mg, 0.597 mmol) in CH₂Cl₂ (3 mL). The reaction mixture was stirred overnight at room temperature in argon atmosphere. After completion of reaction the reaction mixture was diluted with mixed solvent (CHCl₃:i-PrOH=4:1, 10 mL) and washed with sat. NH₄Cl. The organic layer was dried (anhydrous sodium sulfate) and concentrated in vacuo. The crude product was chromatographed on silica gel (Hexanes/EtOAc, 7:1) to yield target compound 4. Yield 306 mg, 90%. $R_f$=0.36, ¹H NMR (CHCl₃, 400 MHz): δ 7.91 (d, J=8.2, Hz, 2H), 7.38 (m, 3H), 7.15 (m, 4H), 3.91 (s, 3H), 3.80 (m, 4H), 3.50 (s, 2H), 0.85 (s, 9H), 0.02 (s, 6H); ¹³C NMR (CHCl₃, 100 MHz): δ 170.2, 167.0, 142.9, 140.8, 129.6, 129.5, 129.1, 128.6, 128.5, 128.0, 60.1, 52.1, 52.0, 41.4, 25.8, 18.2, −5.4; [M+H]⁺=427.84 (APCI+).

4-(2-((2-((tert-butyldimethylsilyl)oxy)ethyl)(phenyl)amino)-2-oxoethyl)-N-hydroxybenzamide (5)

Hydroxylamine (0.5 mL, 50% water solution) was added to a solution containing methyl 4-(2-((2-((tert-butyldimethylsilyl)oxy)ethyl)(phenyl)amino)-2-oxoethyl)benzoate 4 (60 mg, 0.140 mmol) in THF/MeOH (1:1, 1 mL). Reaction mixture was treated with cat. amount of KCN (~0.5 mg) and stirred at room temperature in argon atmosphere for 16 h. Then solution was acidified by NH₄Cl/HCl solution to pH 4. The mixture was diluted with mixed solvent (CHCl₃:i-PrOH=4:1, 10 mL) and washed with sat. NH₄Cl. The organic layer was dried (anhydrous sodium sulfate) and concentrated in vacuo. The crude product was purified by preparative chromatography on silica gel (CH$_2$Cl$_2$/MeOH, 10:1) to yield target compound 5. Yield 40 mg, 66%. R$_f$=0.36, $^1$H NMR (CD$_3$OD, 400 MHz): δ 7.64 (d, J=8.4 Hz, 2H), 7.45 (m, 3H), 7.28 (d, J=8.0 Hz, 2H), 7.13 (d, J=8.0 Hz, 2H), 3.80 (m, 4H), 3.54 (s, 2H), 0.88 (s, 9H), 0.05 (s, 6H); $^{13}$C NMR (CD$_3$OD, 100 MHz): δ 172.0, 167.0, 142.6, 139.7, 130.8, 129.7, 128.8, 128.4, 127.6, 126.2, 60.7, 52.0, 41.0, 26.2, 18.0, −5.4; [M+H]$^+$=428.85 (APCI+).

N-hydroxy-4-(2-((2-hydroxyethyl)(phenyl)amino)-2-oxoethyl)benzamide (6)

4-(2-((2-((tert-butyldimethylsilyl)oxy)ethyl) (phenyl)amino)-2-oxoethyl)-N-hydroxybenzamide 5 (16 mg, 0.037 mmol) was dissolved in 5% TFA in CH$_2$Cl$_2$ (3 mL) and stirred for 5 min. Then the organic layer was concentrated in vacuo. The crude product was purified by preparative chromatography on silica gel (CH$_2$Cl$_2$/MeOH, 10:1) to yield target compound 5. Yield 8 mg, 68%. R$_f$=0.23, $^1$H NMR (CD$_3$OD, 400 MHz): δ 7.64 (d, J=8.4 Hz, 2H), 7.45 (m, 3H), 7.29 (d, J=8.0 Hz, 2H), 7.14 (d, J=8.0 Hz, 2H), 3.86 (t, J=6.0 Hz, 2H), 3.68 (t, J=6.0 Hz, 2H), 3.55 (s, 2H); $^{13}$C NMR (CD$_3$OD, 100 MHz): δ 172.0, 166.9, 142.7, 139.7, 130.9, 129.9, 129.4, 128.7, 128.5, 127.1, 58.8, 51.8, 41.0; [M+H]+=315.26 (APCI+).

2-(4-(methoxycarbonyl)phenyl)acetic acid (8)

Methanol (6.38 g, 198.6 mmol), acetic acid (3.61 g, 60.18 mmol), calcium hypochlorite (4.30 g, 30.1 mmol) and molecular sieves (8.6 g) were added sequentially to a solution containing 2-(4-(hydroxymethyl)phenyl)acetic acid (7, 1.00 g, 6.02 mmol) in acetonitrile (50 mL). The reaction mixture was stirred in dark at room temperature in argon atmosphere for 24 h. Another portion of methanol (6.38 g, 198.6 mmol) and calcium hypochloride (1.72 g, 12.0 mmol) were added to the reaction mixture and stirred for 24 h. NMR analysis showed complete consumption of both the starting material and the intermediate aldehyde. Water (20 mL) and sodium thiosulfate (4 g) were added to quench remaining hypochlorite. Added 50 mL sat. NaHCO$_3$ and filtered under suction. The filterate was washed with ethylacetate (30 mL×2). The aqueous layer was acidified with 2 N HCl to pH ~2 and extracted with ethylacetate (50 mL×3). Combined organic layer was dried (anhydrous sodium sulfate) and concentrated in vacuo. The crude product was chromatographed on silica gel (CH$_2$Cl$_2$/MeOH, 10:1) to yield target compound 8. Yield 740 mg, 63%. R$_f$=0.53, $^1$H NMR (CHCl$_3$, 400 MHz): δ 8.03 (d, J=8.3 Hz, 2H), 7.38 (d, J=8.3 Hz, 2H), 3.93 (s, 3H), 3.7 (s, 2H); $^{13}$C NMR (CHCl$_3$, 100 MHz): δ 176.4, 166.8, 138.3, 129.9, 129.5, 129.3, 52.1, 40.8; [M+H]$^+$=195.03 (APCI+).

Example 2

Synthesis of Compound 14

HDAC inhibitor 14 was accessed according to the protocols shown in Scheme 3. Alcohol 10 was prepared by treatment of amine 9 with glycolaldehyde followed by addition of sodium triacetoxyborohydride. The alcohol 10 was then protected with TBDMSCl followed by EDC coupling with acid 8 (Scheme 2). The methyl ester 12 was converted directly, using a catalytic amount of KCN, to the corresponding hydroxamic acid 13, which was deprotected with TFA to afford compound 14.

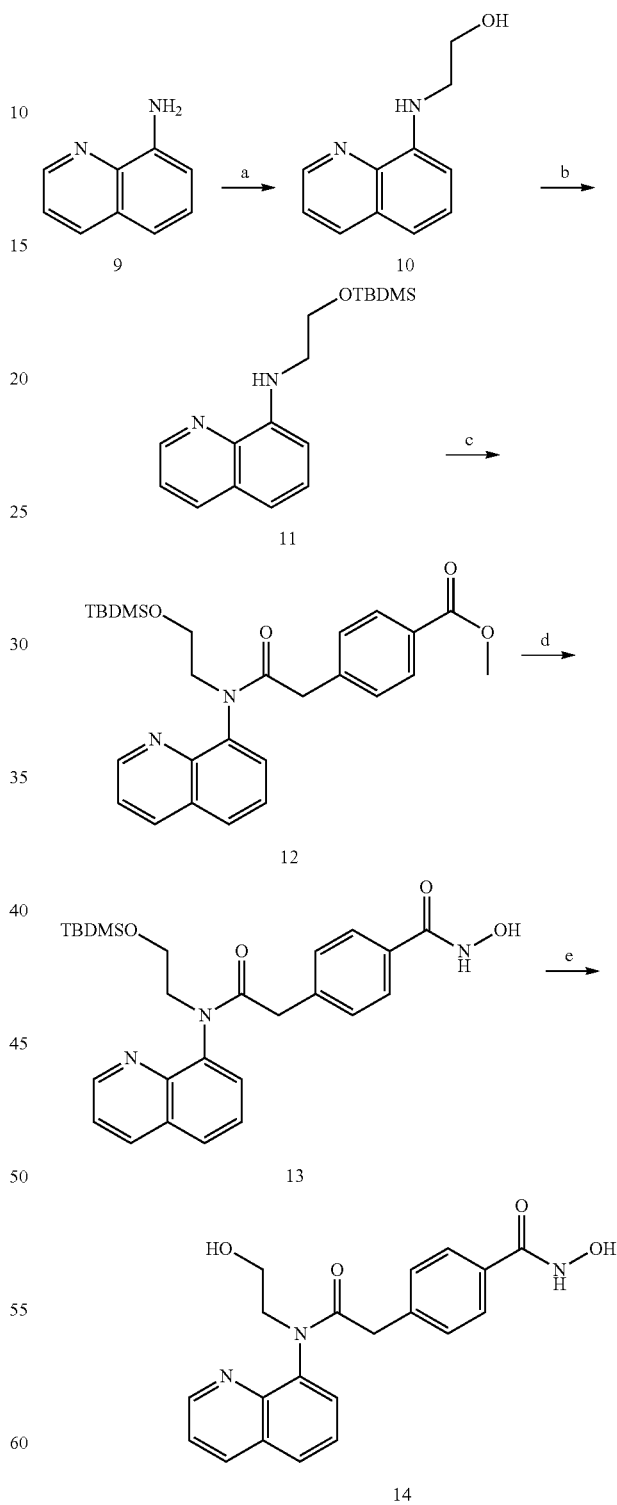

Scheme 3.

Reagents: (a) 1. HOCH$_2$CHO, DCE, 30 min. rt. 2. NaBH(OAc)$_3$, 4 h. rt.
(b) TBDMS-Cl, DCM, 3 h. (c) 8, EDC, DCM, rt. 24 h. (d) NH$_2$OH, THF:MeOH (1:1), KCN (cat.) 16 h, rt. (e) 5% TFA in DCM, 5 min.

2-(quinolin-8-ylamino)ethanol (10)

Glycolaldehyde (437 mg, 7.29 mmol) was added to a solution containing 8-aminoquinoline (9, 1.00 g, 6.94 mmol) in DCE (30 mL). The solution was stirred at room temperature in argon atmosphere for 30 min. Sodium triacetoxyborohydride (1.86 g, 3.84 mmol) was then added portionwise. The reaction mixture was further stirred for 4 h and quenched with NaHCO$_3$ to pH=9.0. The reaction mixture was extracted with mixed solvent (CHCl$_3$:i-PrOH=4:1, 30 mL×3). The organic layer was dried (sodium sulfate) and concentrated in vacuo. The crude product was chromatographed on silica gel (CH$_2$Cl$_2$/MeOH, 20:1) to yield target compound 10. Yield 0.950 g, 73%. R$_f$=0.6, $^1$H NMR (CHCl$_3$, 400 MHz): δ 7.24 (dd, J=8.8, 7.4 Hz, 2H), 6.80 (t, J=7.4 Hz, 1H), 6.69 (d, J=8.8, 2H), 3.81 (t, J=5.2 Hz, 2H), 3.30 (t, J=5.2 Hz, 2H), 2.6 (br s, 1H); [M+H]$^+$=138.08 (APCI+)

N-(2-((tert-butyldimethylsilyl)oxy)ethyl)quinolin-8-amine (11)

TBDMS-Cl (624 mg, 4.13 mmol) and imidazole (648 mg, 9.51 mmol) was added to a solution containing 2-(quinolin-8-ylamino)ethanol 10 (600 mg, 3.19 mmol) in CH$_2$Cl$_2$ (6 mL). The reaction mixture was stirred at room temperature in argon atmosphere for 3 h. Then the reaction was quenched with sat. NH$_4$Cl. and washed with water (10 mL×2) and brine (10 mL×2). The organic layer was dried (sodium sulfate) and concentrated in vacuo. The crude product was chromatographed on silica gel (Hexanes/EtOAc, 7:1) to yield target compound 11. Yield 730 g, 75%. R$_f$=0.65, $^1$H NMR (CHCl$_3$, 400 MHz): δ 8.73 (dd, J=4.2, 1.7 Hz, 1H), 8.07 (dd, J=8.2, 1.2 Hz, 1H), 7.39 (m, 2H), 7.07 (dd, J=8.2, 0.8 Hz, 1H), 6.73 (d, J=7.6 Hz, 1H), 6.50 (br s, 1H), 3.97 (t, J=5.9 Hz, 2H), 3.48 (t, J=5.9 Hz, 2H), 0.94 (s, 9H), 0.10 (s, 6H); $^{13}$C NMR (CHCl$_3$, 100 MHz): δ 146.8, 144.9, 135.9, 128.7, 127.7, 121.3, 113.9, 104.8, 61.7, 45.5, 25.9, 18.3, −5.3; [M+H]+=303.25 (APCI+).

Methyl 4-(2-((2-((tert-butyldimethylsilyl)oxy)ethyl)(quinolin-yl)amino)-2-oxoethyl)benzoate (12)

EDC (147 mg, 0.772 mmol) was added to a solution containing N-(2-((tert-butyldimethylsilyl)oxy)ethyl)quinolin-8-amine 11 (156 mg, 0.545 mmol) and 2-(4-(methoxycarbonyl)phenyl)acetic acid 8, (150 mg, 0.772 mmol) in CH$_2$Cl$_2$ (3 mL). The reaction mixture was stirred overnight at room temperature in argon atmosphere. After completion of reaction the reaction mixture was diluted with mixed solvent (CHCl$_3$:i-PrOH=4:1, 10 mL) and washed with sat. NH$_4$Cl. The organic layer was dried (sodium sulfate) and concentrated in vacuo. The crude product was chromatographed on silica gel (CH$_2$Cl$_2$/MeOH, 15:1) to yield target compound 12. Yield 170 mg, 69%. R$_f$=0.40, $^1$H NMR (CHCl$_3$, 400 MHz): δ 8.93 (dd, J=4.1, 1.5 Hz, 1H), 8.28 (dd, J=8.3, 1.5 Hz, 1H), 7.87 (dd, J=8.2, 1.3 Hz, 1H), 7.82 (d, J=8.2, 2H), 7.64 (dd, J=7.3, 1.2 Hz, 1H), 7.51 (m, 2H), 7.02 (d, J=8.2, 2H), 4.39 (m, 1H), 3.96 (m, 1H), 3.73 (m, 1H), 3.55 (m, 1H), 3.35 (m, 2H), 1.8 (br s, 1H), 0.81 (s, 9H), 0.10 (s, 6H), 0.10 (s, 3H), 0.04 (s, 3H); $^{13}$C NMR (CHCl$_3$, 100 MHz): δ 171.2, 167.0, 151.0, 144.5, 141.1, 140.4, 136.2, 130.2, 129.4, 129.3, 129.1, 128.4, 128.1, 126.2, 121.8, 61.7, 52.3, 51.9, 41.6, 25.8, 18.1, −5.4, −5.5; [M+H]+=479.29 (APCI+).

4-(2-((2-((tert-butyldimethylsilyl)oxy)ethyl)(quinolin-8-yl)amino)-2-oxoethyl)-N-hydroxybenzamide (13)

Hydroxylanmine (0.5 mL, 50% water solution) was added to a solution containing methyl methyl 4-(2-((2-((tert-butyldimethylsilyl)oxy)ethyl) (quinolin-8-yl)amino)-2-oxoethyl)benzoate 12 (70 mg, 0.146 mmol) in THF/MeOH (1:1, 1 mL). Reaction mixture was treated with cat. amount of KCN (~0.5 mg) and stirred at room temperature in argon atmosphere for 16 h. Then solution was acidified by NH$_4$Cl/HCl solution to pH 4. The mixture was diluted with diluted with mixed solvent (CHCl$_3$:i-PrOH=4:1, 10 mL) and washed with sat. NH$_4$Cl. The organic layer was dried (sodium sulfate) and concentrated in vacuo. The crude product was purified by preparative chromatography on silica gel (CH$_2$Cl$_2$/MeOH, 10:1) to yield target compound 13. Yield 45 mg, 64%. R$_f$=0.60, $^1$H NMR (CHCl$_3$, 400 MHz): δ 8.91 (d, J=3.3 Hz, 1H), 8.41 (d, J=8.1 Hz, 1H), 8.04 (d, J=8.1 Hz, 1H), 7.76 (d, J=7.2, 1H), 7.60 (m, 2H), 7.53 (d, J=8.2, 2H), 6.98 (d, J=7.9, 2H), 4.42 (m, 1H), 3.92 (m, 1H), 3.73 (m, 1H), 3.52 (m, 1H), 3.38 (s, 2H), 0.81 (s, 9H), 0.00 (s, 3H), −0.04 (s, 3H); $^{13}$C NMR (CHCl$_3$, 100 MHz): δ 171.2, 167.0, 151.0, 144.5, 141.1, 140.4, 136.2, 130.2, 129.4, 129.3, 129.1, 128.4, 128.1, 126.2, 121.8, 61.7, 52.3, 51.9, 41.6, 18.1, −5.4, −5.5; [M+H]$^+$=480.46 (APCI+).

N-hydroxy-4-(2-((2-hydroxyethyl)(quinolin-S-yl)amino)-2-oxoethyl)benzamide (14)

4-(2-((2-((tert-butyldimethylsilyl)oxy)ethyl)(quinolin-8-yl)amino)-2-oxoethyl)-N-hydroxybenzamide 13 (34 mg, 0.065 mmol) was dissolved in 5% TFA in CH$_2$Cl$_2$ (3 mL) and stirred for 5 min. Then the organic layer was concentrated in vacuo. The crude product was purified by preparative chromatography on silica gel (CH$_2$Cl$_2$/MeOH, 10:1) to yield target compound 14. Yield 18 mg, 69%. R$_f$=0.20, $^1$H NMR (CHCl$_3$, 400 MHz): δ 8.89 (d, J=3.0 Hz, 1H), 8.50 (d, J=8.2 Hz, 1H), 7.81 (d, J=6.7 Hz, 1H), 7.65 (m, 2H), 7.51 (d, J=8.0, 2H), 6.96 (d, J=8.0, 2H), 4.08 (m, 1H), 3.92 (m, 1H), 3.70 (m, 2H), 3.74 (s, 2H); $^{13}$C NMR (CHCl$_3$, 100 MHz): δ 171.2, 167.0, 150.1, 143.5, 139.1, 138.3, 137.7, 130.9, 130.2, 129.8, 129.3, 128.9, 126.8, 126.5, 122.1, 58.6, 51.7, 41.0; [M+H]$^+$=366.33 (APCI+).

Example 3

Synthesis of Compounds with Various Linkers

HDAC inhibitor 19 is accessed according to the protocols shown in Scheme 4. 4-Aminophenylacetic acid 15 is converted to aniline 16 using methods similar to those described in Scheme 1. Aniline 16 is coupled to acid 17 using EDC. The resulting methyl carbamate derivative 18 is converted directly, using a catalytic amount of KCN, to the corresponding hydroxamic acid, which is deprotected with TFA to afford compound 19. Alternative coupling partner, carboxylic acid 20, is also used to synthesize compound 21 (Scheme 5).

Scheme 4.

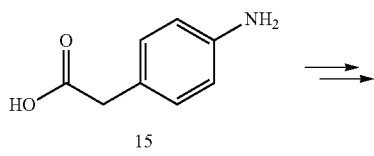

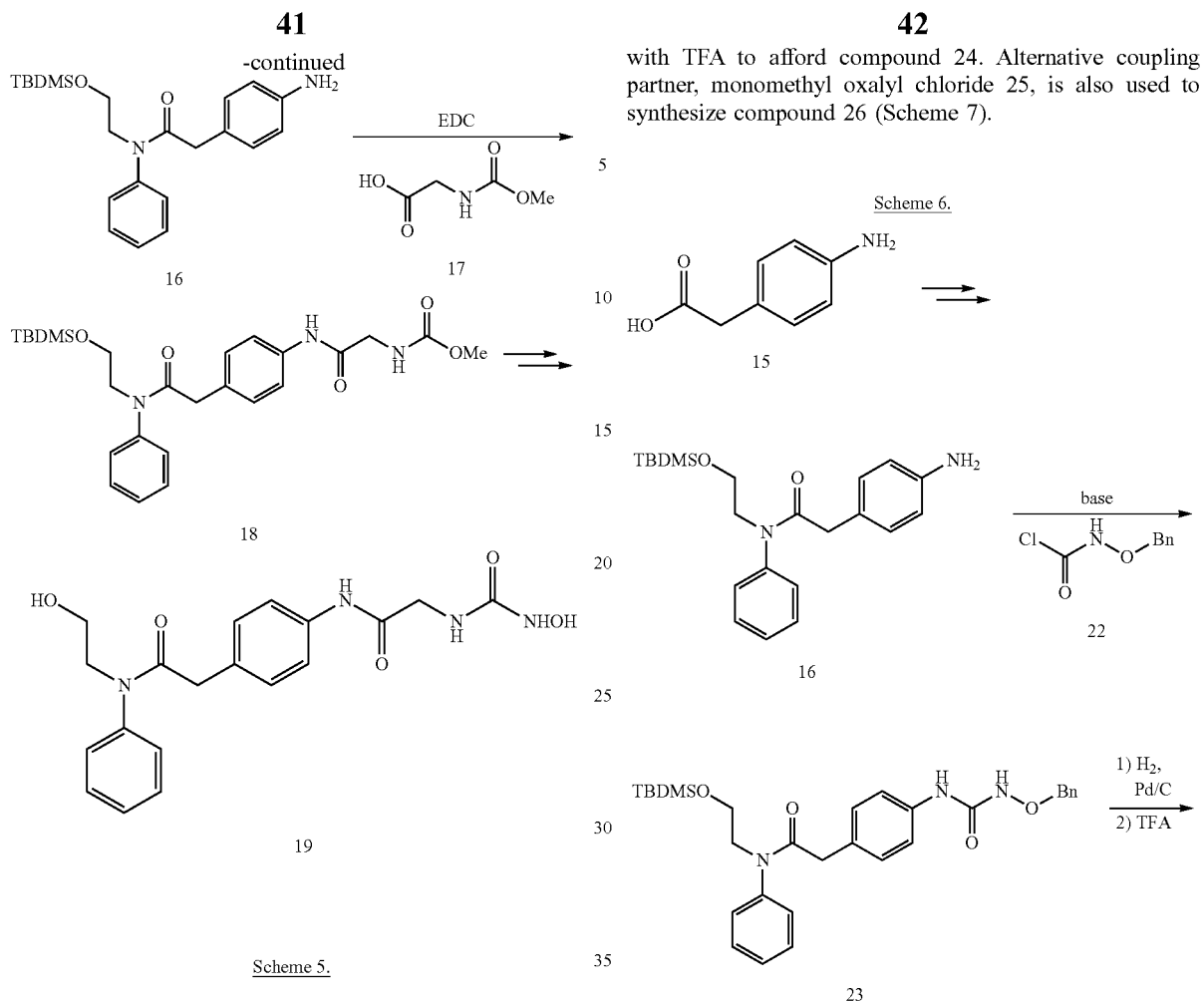

with TFA to afford compound 24. Alternative coupling partner, monomethyl oxalyl chloride 25, is also used to synthesize compound 26 (Scheme 7).

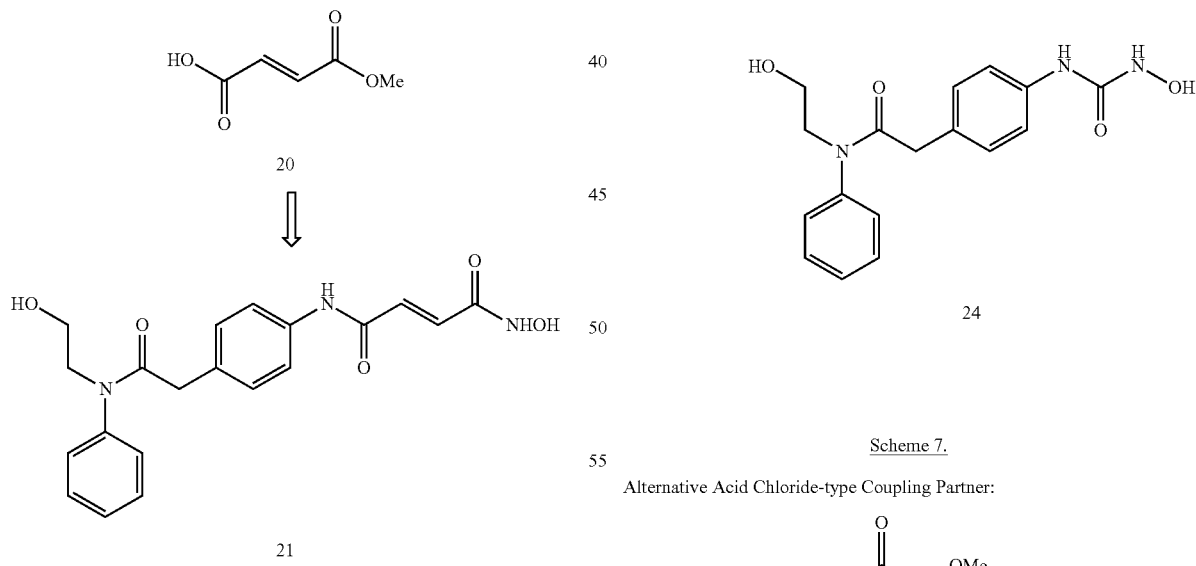

HDAC inhibitor 24 is accessed according to the protocols shown in Scheme 6. 4-Aminophenylacetic acid 15 is converted to aniline 16 using methods similar to those described in Scheme 1. Aniline 16 is coupled to carbamic chloride derivative 22 under basic conditions. The resulting urea-type derivative 23 is converted to the corresponding N-hydroxy urea under hydrogenation conditions, which is deprotected

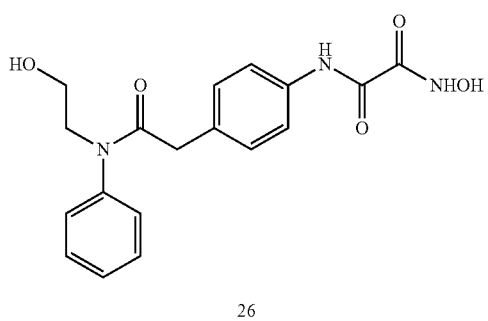

26

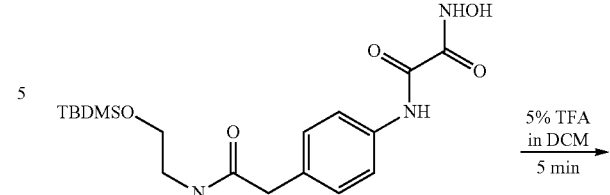

29

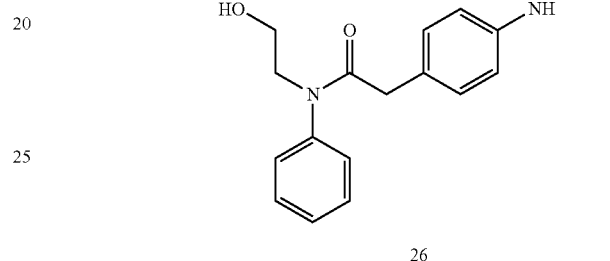

26

Example 4

Synthesis of Compound 26

HDAC inhibitor 26 was accessed according to the protocols shown in Scheme 8. 4-Aminophenylacetic acid 15 was converted to acid 27. Acid was coupled to substituted aniline 3. The resulting amide derivative 28 was converted to HDAC inhibitor 26 using methods previously described in Scheme 1.

Scheme 8.

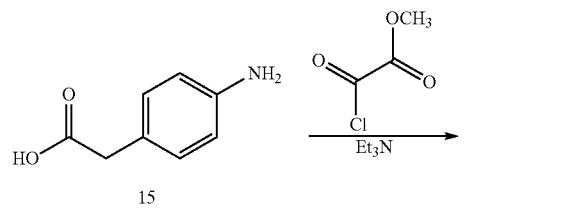

15

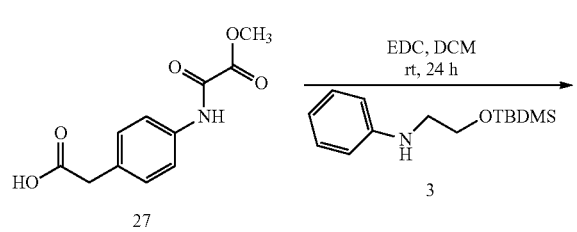

27

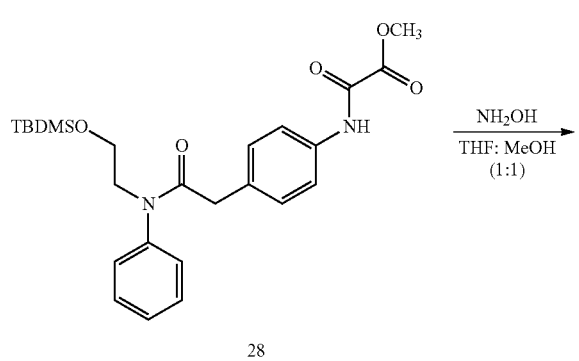

28

Example 5

Synthesis of Compound 24

HDAC inhibitor 24 was accessed according to the protocols shown in Scheme 9. 4-Aminophenylacetic acid 15 was converted to acid 30 using CDI in the presence of O-benzylhydroxylamine. Acid 30 was coupled to substituted aniline 3. The resulting amide derivative 31 was converted to the N-hydroxy urea under hydrogenation conditions, which was deprotected with TFA to afford HDAC inhibitor 24.

Scheme 9.

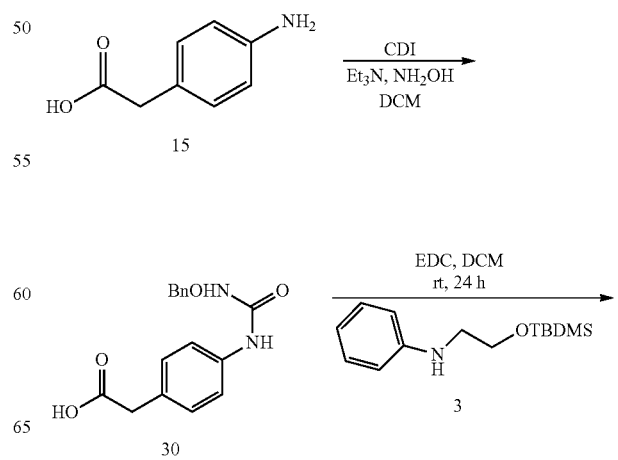

15

30

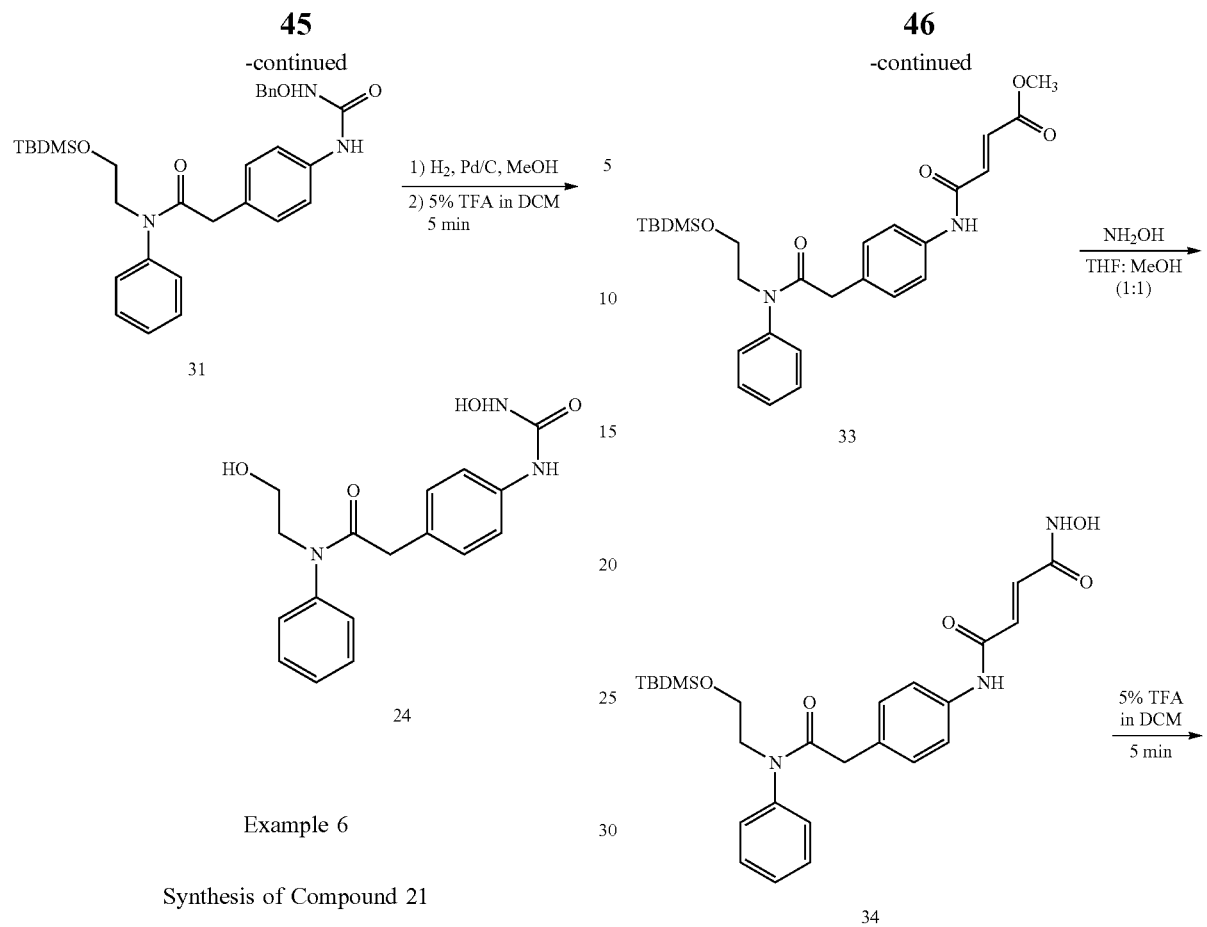

Example 6

Synthesis of Compound 21

HDAC inhibitor 21 was accessed according to the protocols shown in Scheme 10. 4-Aminophenylacetic acid 15 was acylated with the acid chloride of methylfumurate to form acid 32. Acid 32 was coupled to substituted aniline 3. The resulting amide derivative 33 was converted to HDAC inhibitor 21 using methods previously described in Scheme 1.

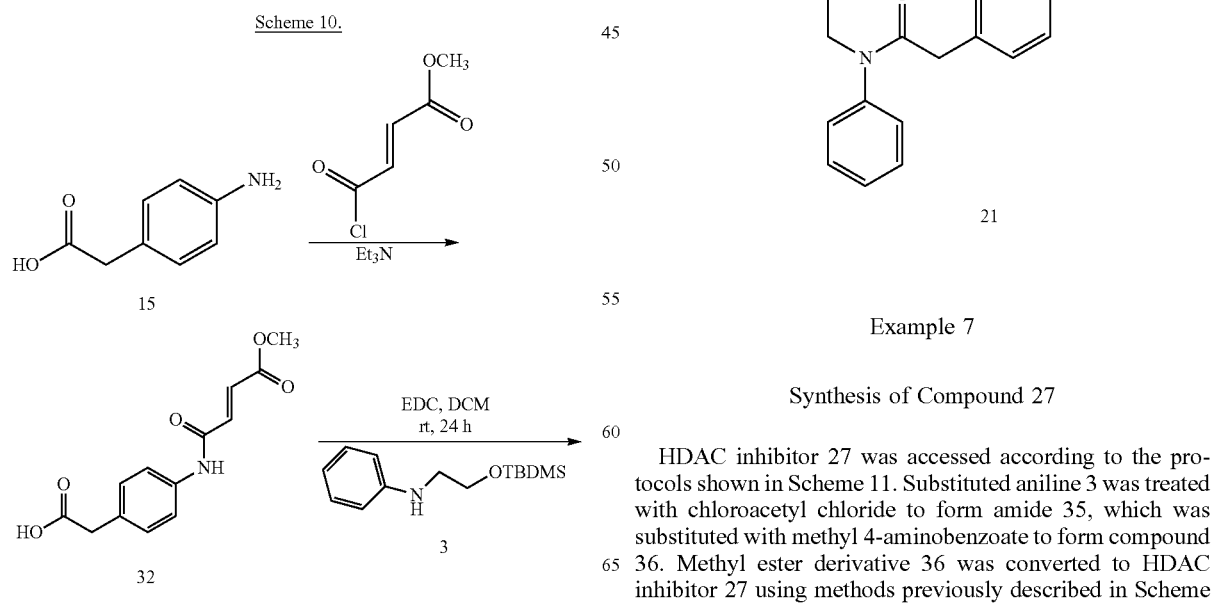

Example 7

Synthesis of Compound 27

HDAC inhibitor 27 was accessed according to the protocols shown in Scheme 11. Substituted aniline 3 was treated with chloroacetyl chloride to form amide 35, which was substituted with methyl 4-aminobenzoate to form compound 36. Methyl ester derivative 36 was converted to HDAC inhibitor 27 using methods previously described in Scheme 1.

Scheme 11.

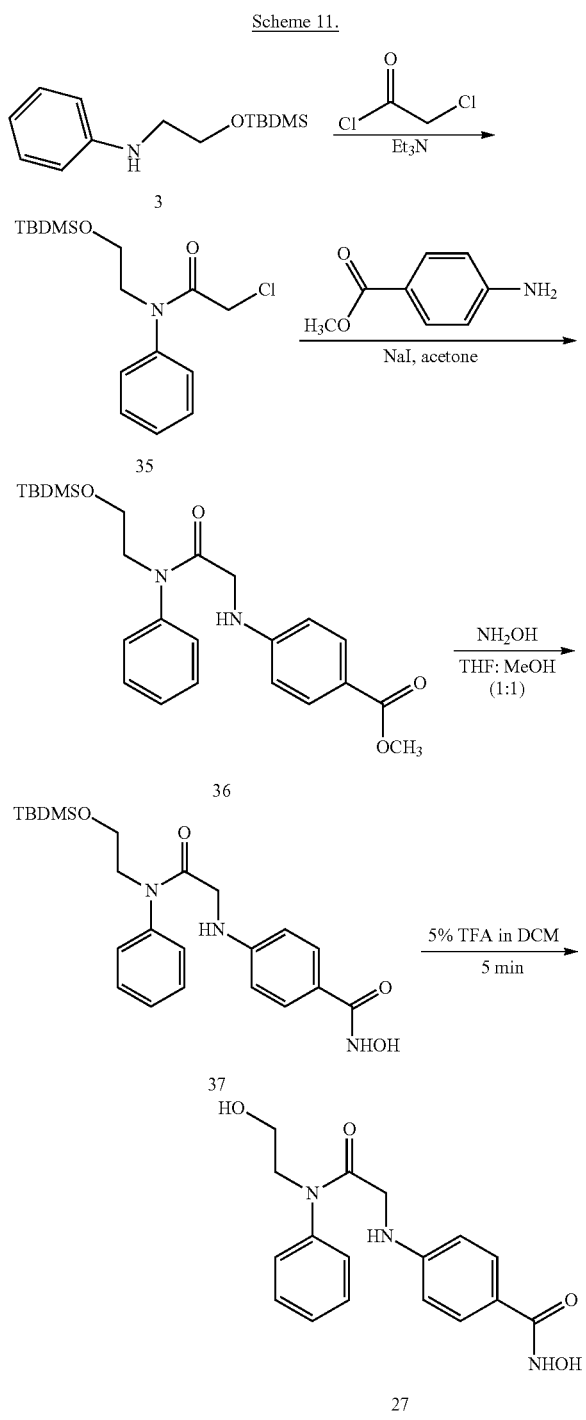

Example 8

Synthesis of Compounds 28 and 29

HDAC inhibitors 28 and 29 were accessed according to the protocols shown in Scheme 12. Hydroxylamine 38 was N-acylated with the corresponding acid chloride to form N-hydroxyamide 39, which was coupled to aniline 3 followed by deprotection to form HDAC inhibitors 28 and 29.

Scheme 12.

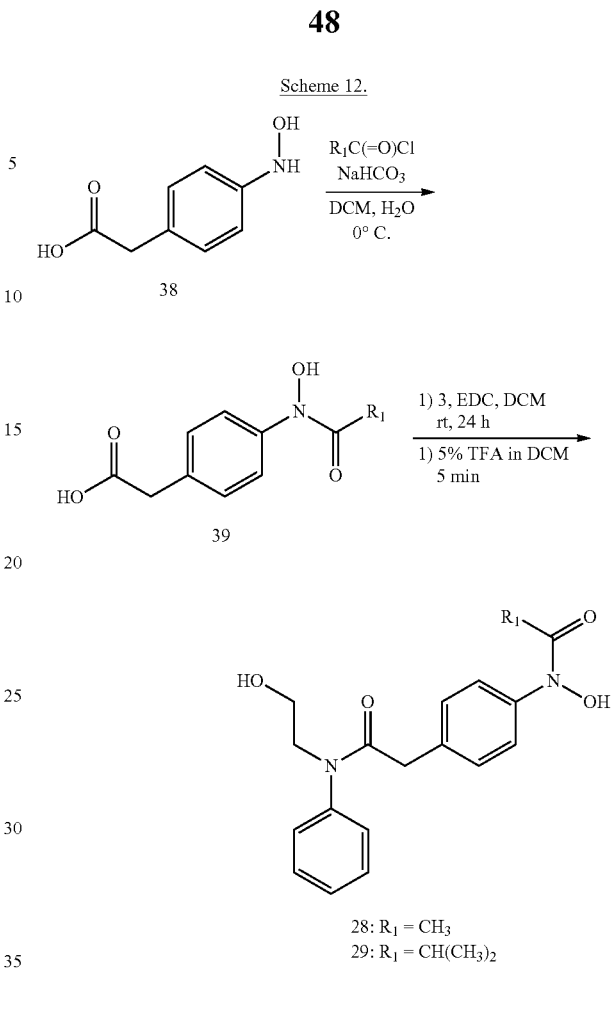

Example 9

Synthesis of Compounds 30 and 32

HDAC inhibitor 30 was accessed according to the protocols shown in Scheme 13. Methyl 4-aminobenzoate was acylated with chloroacetyl chloride to form amide 40, which was coupled with aniline 3. The methyl ester derivative 41 was converted to HDAC inhibitor 30 using methods previously described in Scheme 1. Methyl 4-hydroxybenzoate was converted to HDAC inhibitor 32 using a similar sequence (Scheme 14).

Scheme 13.

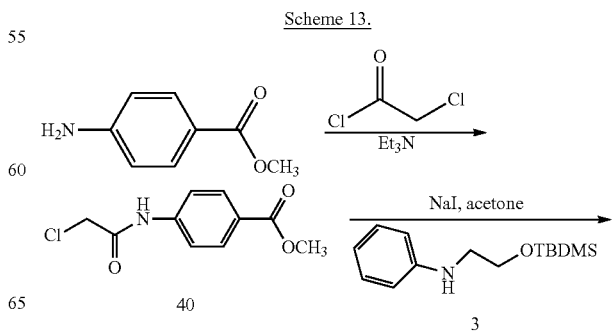

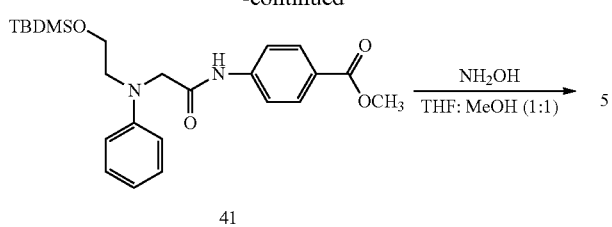
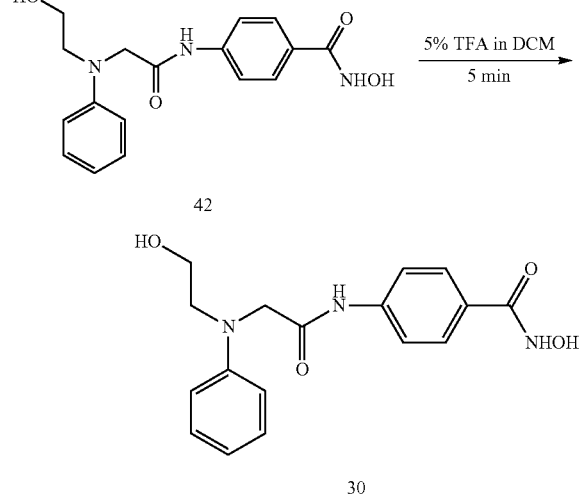
Scheme 14.
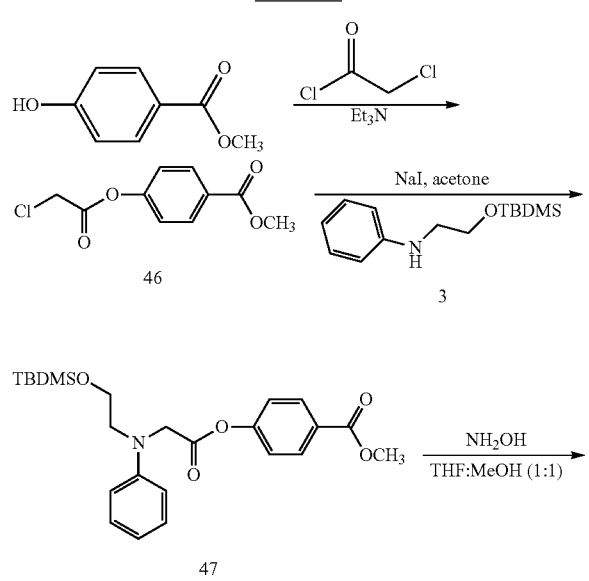
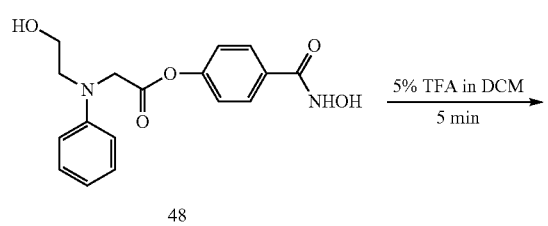
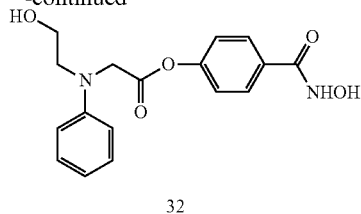
Example 10
Synthesis of Compound 31
HDAC inhibitor 31 was accessed according to the protocols shown in Scheme 15. 4-Aminophenylacetic acid 15 was acylated with methyl malonyl chloride to form acid 43. Acid 43 was coupled to substituted aniline 3. The resulting amide derivative 44 was converted to HDAC inhibitor 31 using methods previously described in Scheme 1.
Scheme 15.
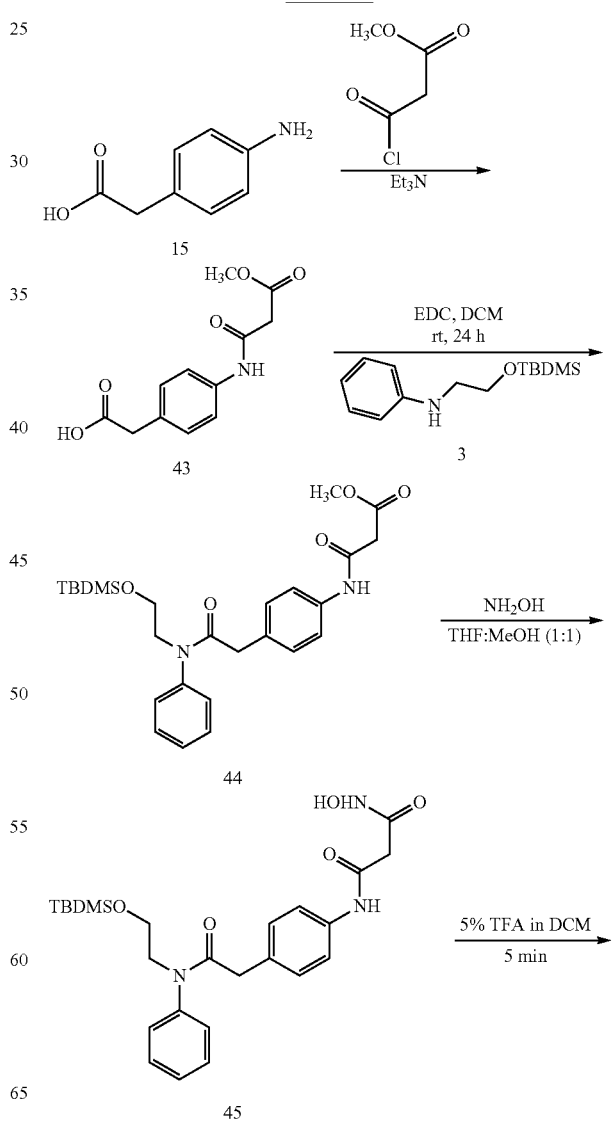

51

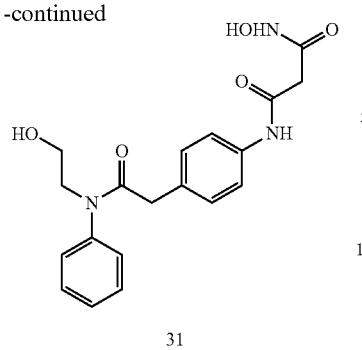

31

Example 11

Synthesis of Compound 33

HDAC inhibitor 33 was accessed according to the protocols shown in Scheme 16. 4-(Methoxycarbonyl)benzoic acid was coupled to substituted aniline 3. The resulting amide derivative 49 was converted to HDAC inhibitor 33 using methods previously described in Scheme 1.

Example 12

Synthesis of Compounds 34, 35 and 36

HDAC inhibitor 34 was accessed according to the protocols shown in Scheme 17. 4-(2-Methoxy-2-oxoethyl)benzoic acid was coupled to substituted aniline 3. The resulting amide derivative 51 was converted to HDAC inhibitor 34 using methods previously described in Scheme 1. 4-(3-Methoxy-3-oxopropyl)benzoic acid and 2-(4-(3-methoxy-3-oxopropyl)phenyl) acetic acid were converted to HDAC inhibitors 35 and 36, respectively, using a similar sequence (Schemes 18 and 19).

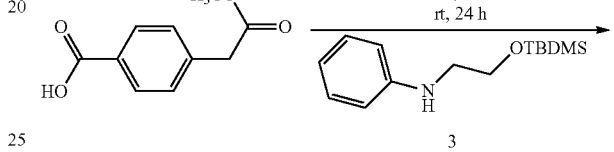

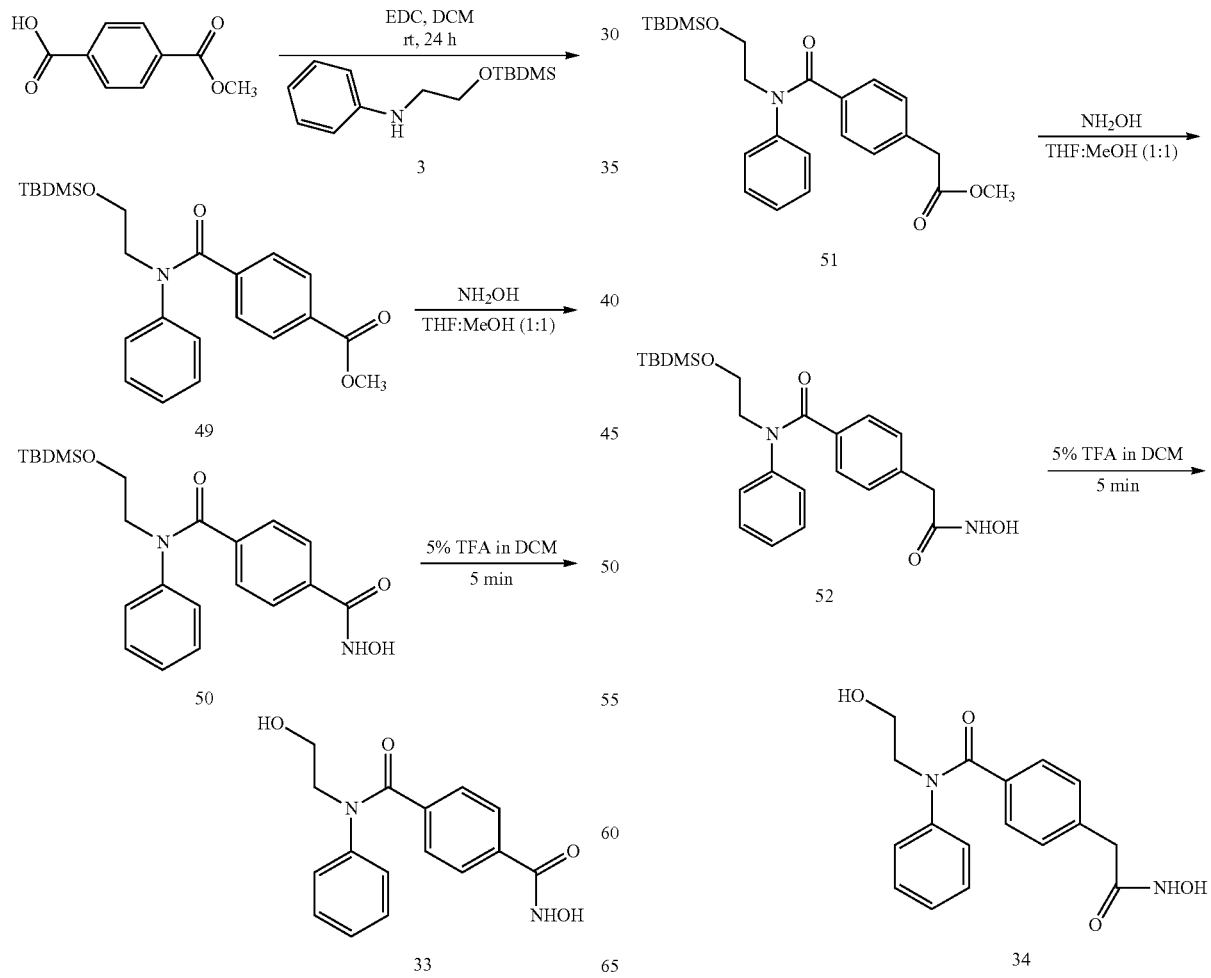

Scheme 18.
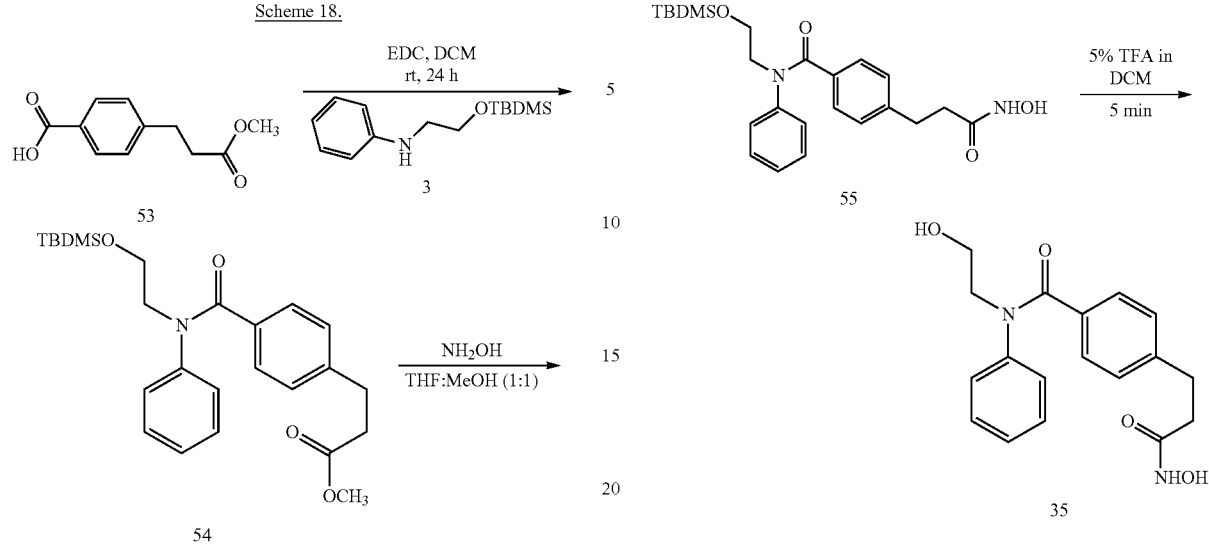
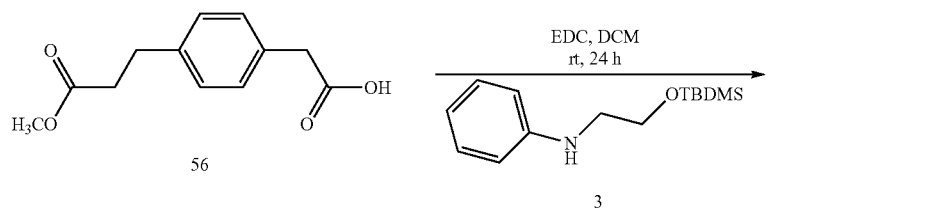
Scheme 19.
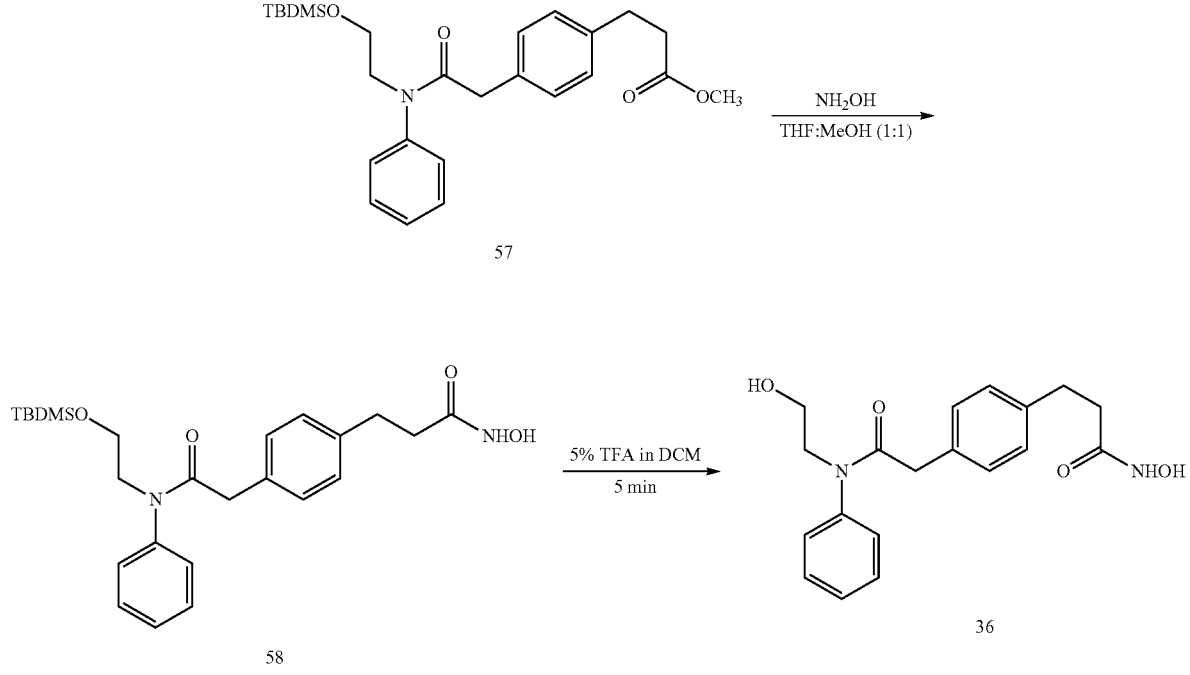

Example 13

Ar₁ Derivatives

HDAC inhibitors with various Ar₁ groups were synthesized according to the protocols shown in Schemes 20-25. Aniline 3 was acylated with chloroacetyl chloride to form alkyl chloride 35. Chloride 35 was substituted with the corresponding aniline-type derivative to form methyl esters 59, 62, 64, 66, 68 and 70, which were then converted to the HDAC inhibitors 37, 38, 39, 40, 41, 42 and 43 using methods previously described in Scheme 1

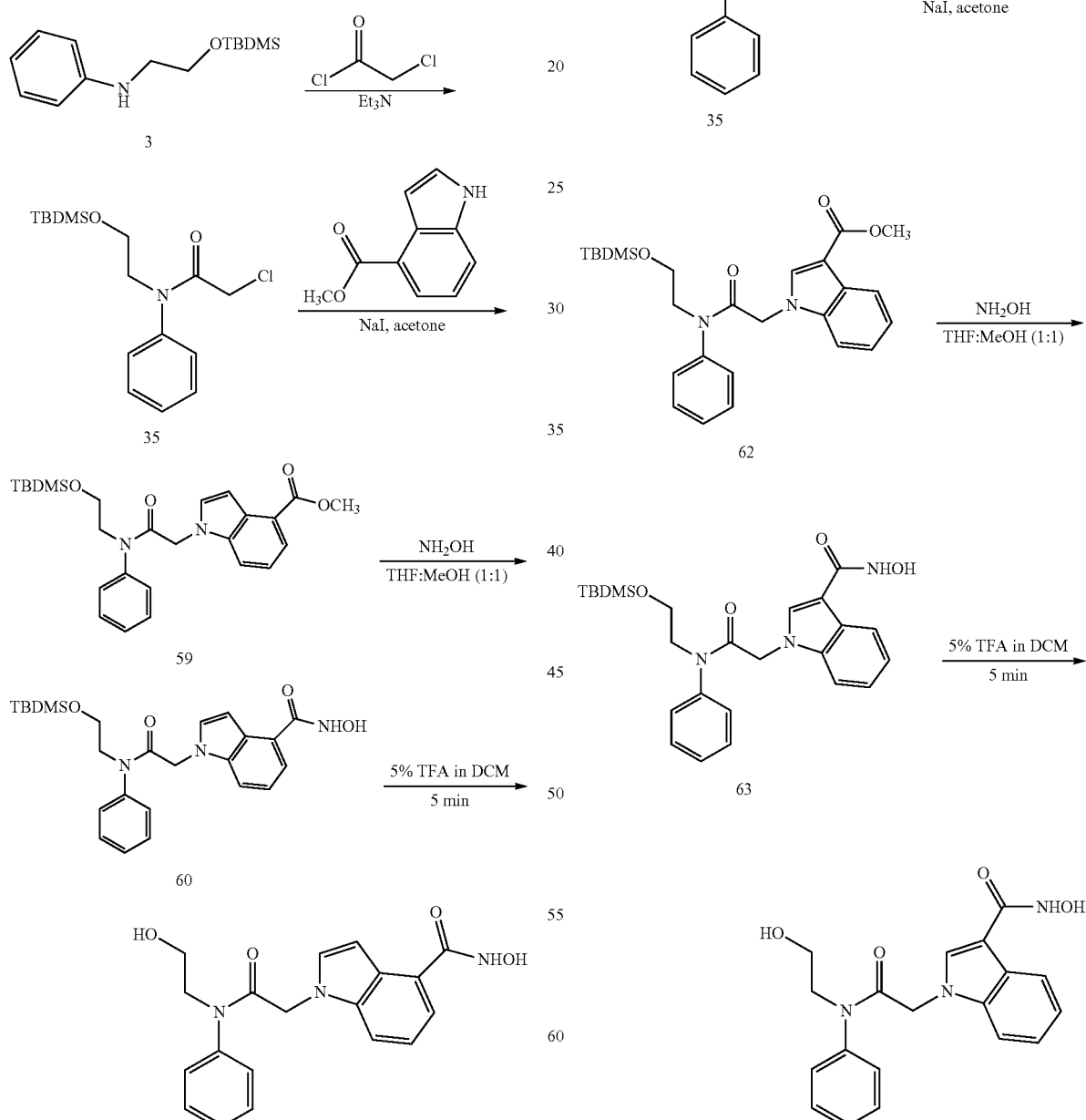

Scheme 20.

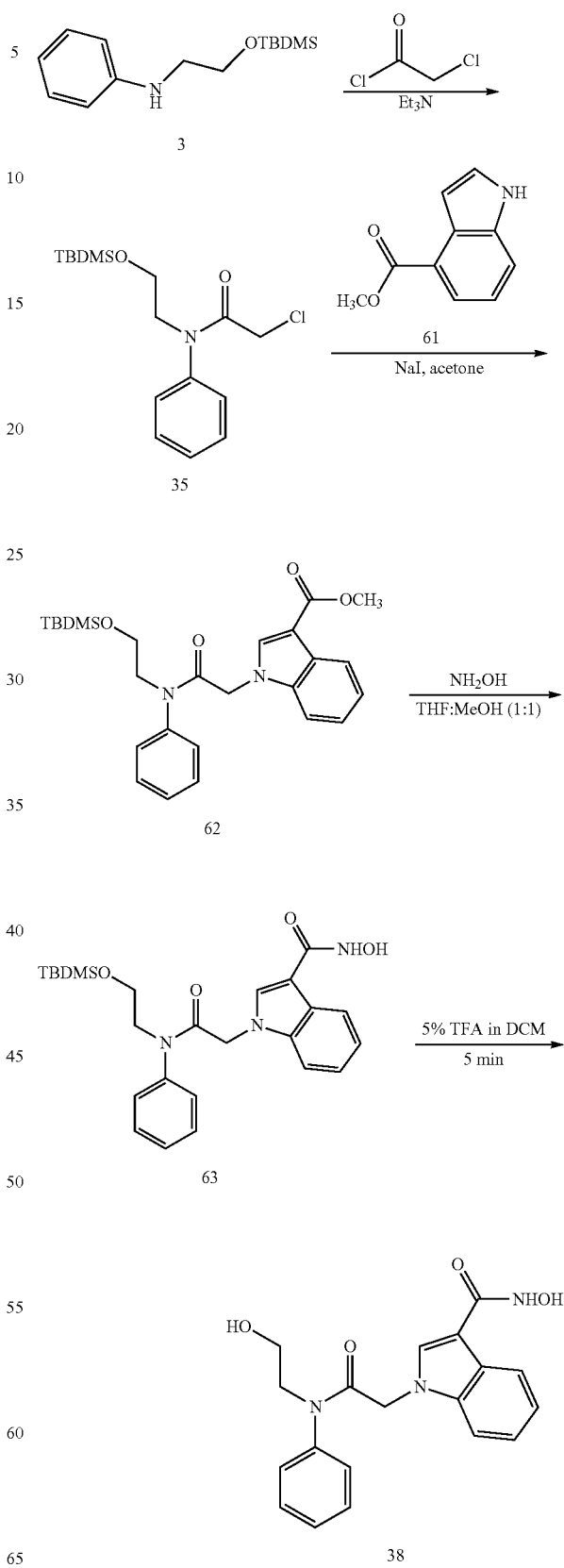

Scheme 21.

Scheme 22.
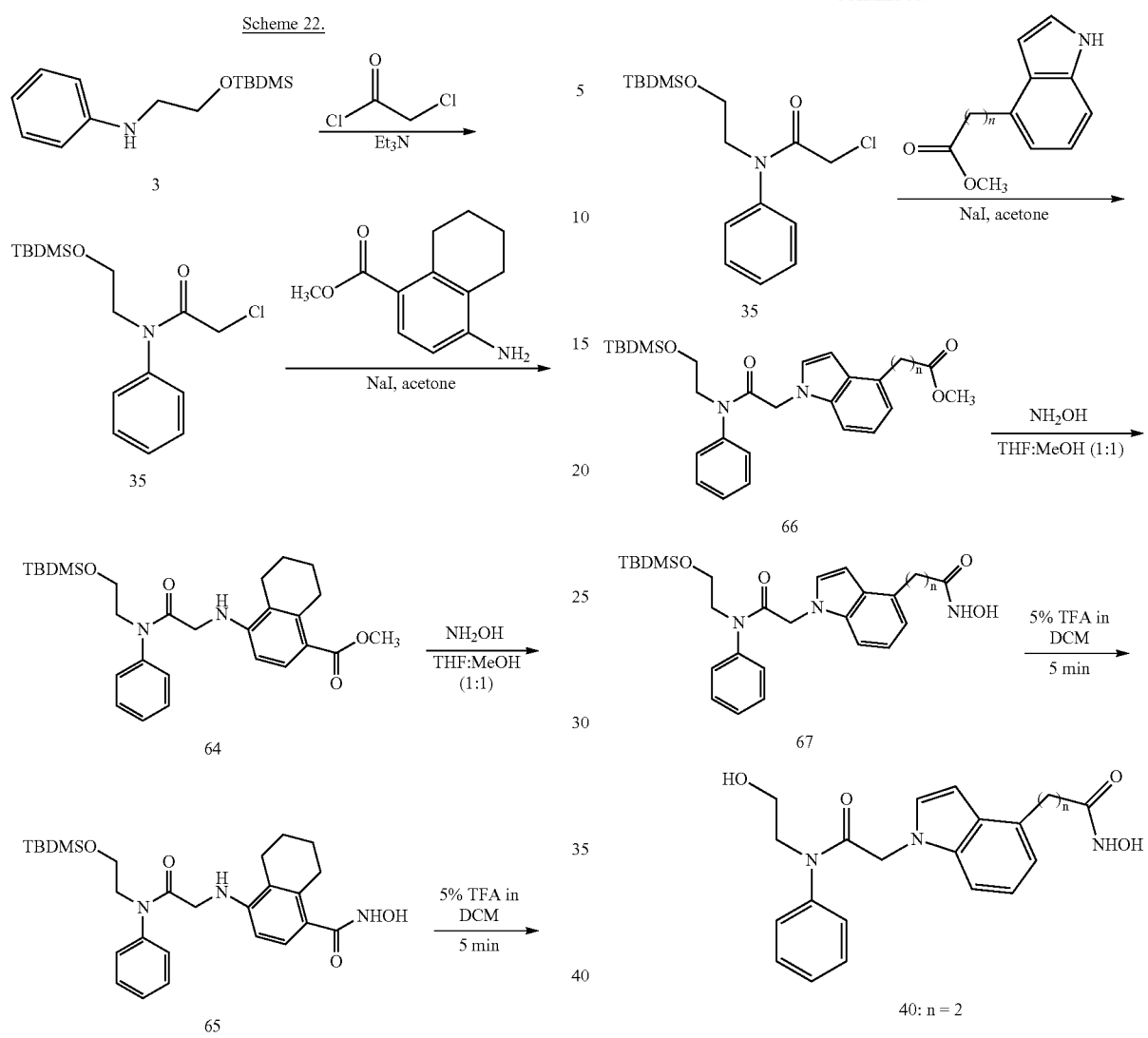
Scheme 23.
Scheme 24.
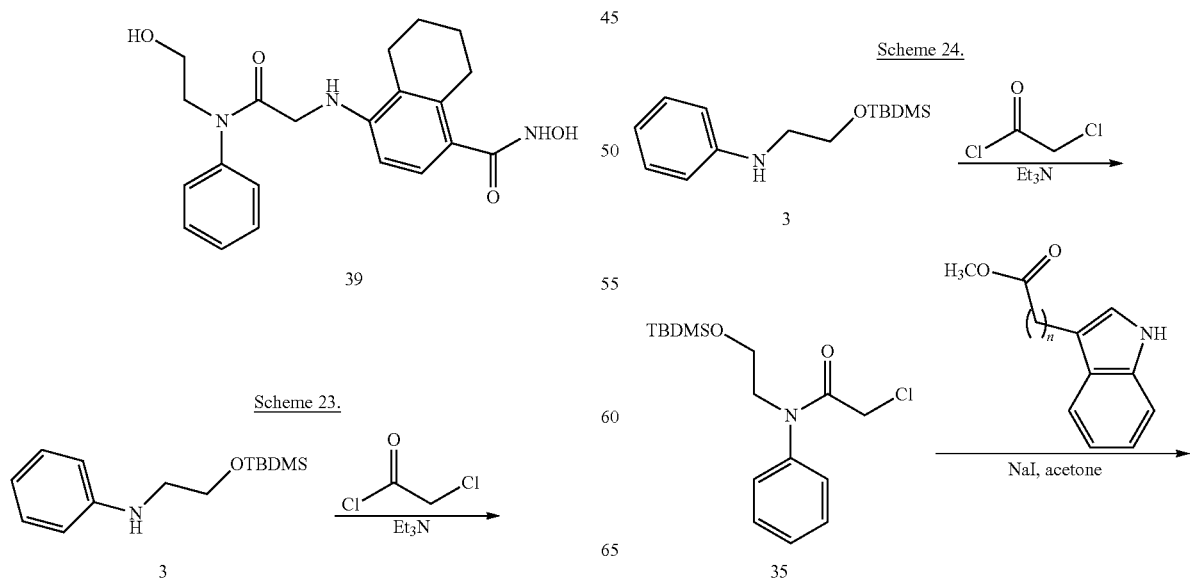

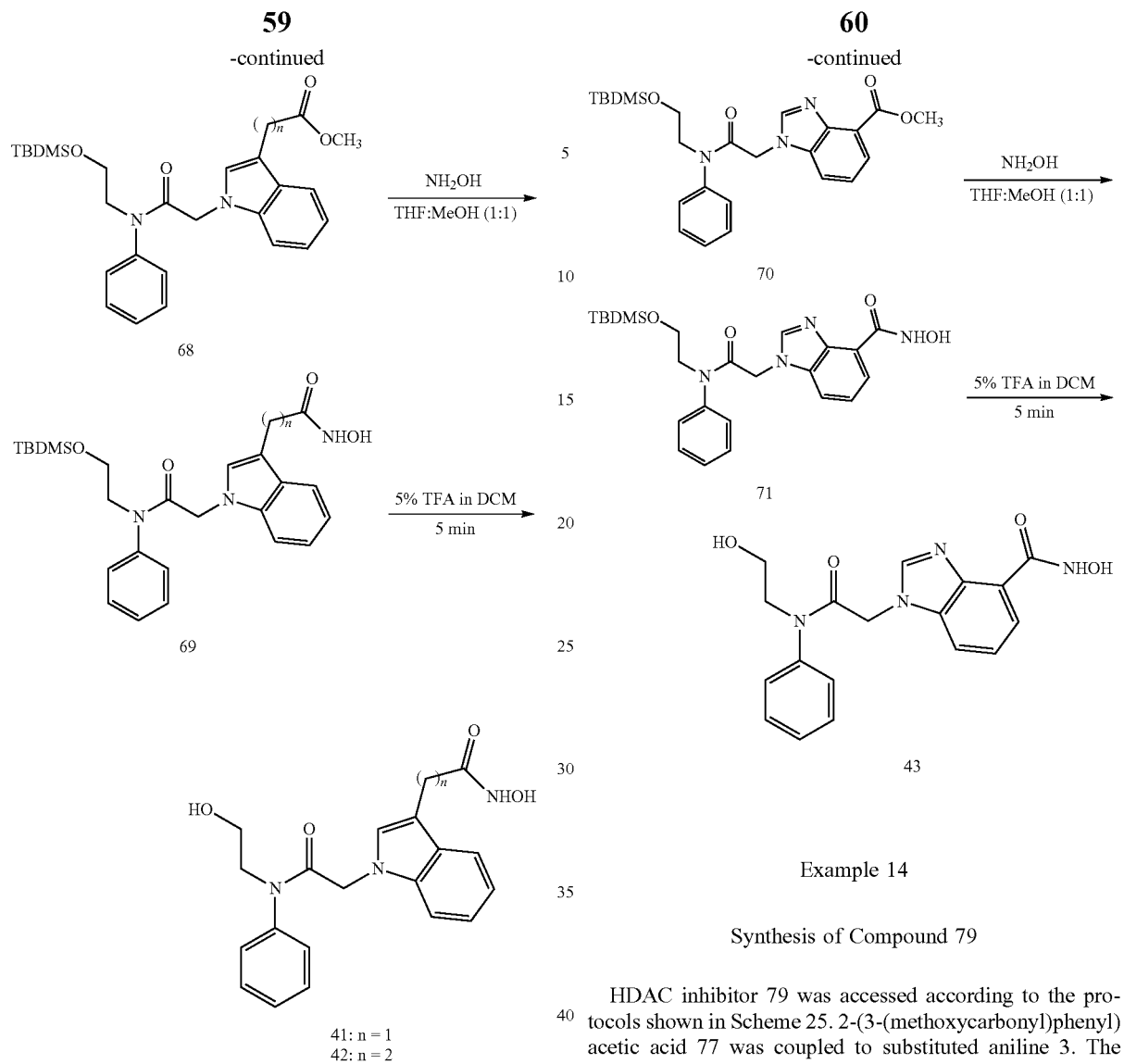
Example 14
Synthesis of Compound 79
HDAC inhibitor 79 was accessed according to the protocols shown in Scheme 25. 2-(3-(methoxycarbonyl)phenyl)acetic acid 77 was coupled to substituted aniline 3. The resulting amide derivative 78 was converted to HDAC inhibitor 79 using methods previously described in Scheme 1 (Scheme 25).
Scheme 25.
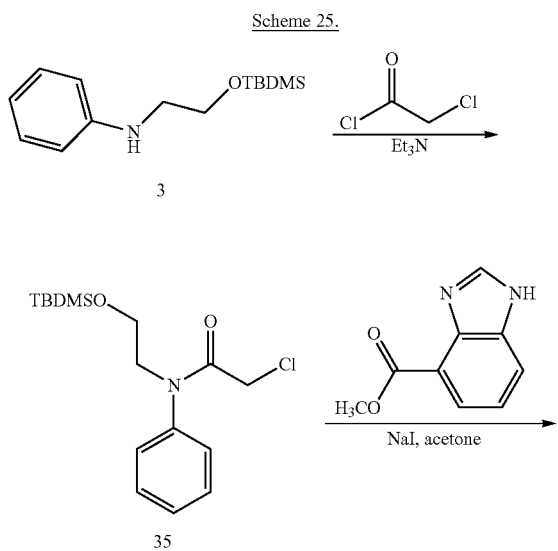
Scheme 25.
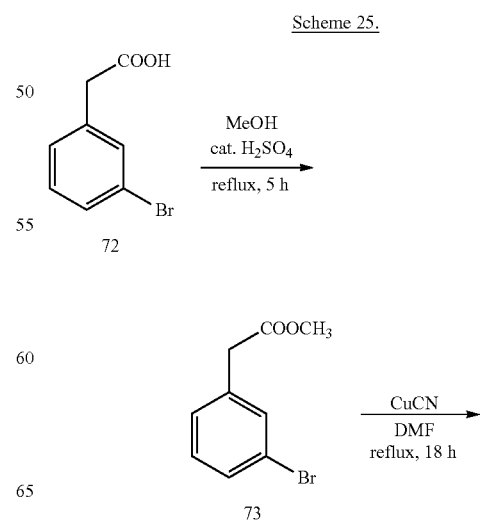

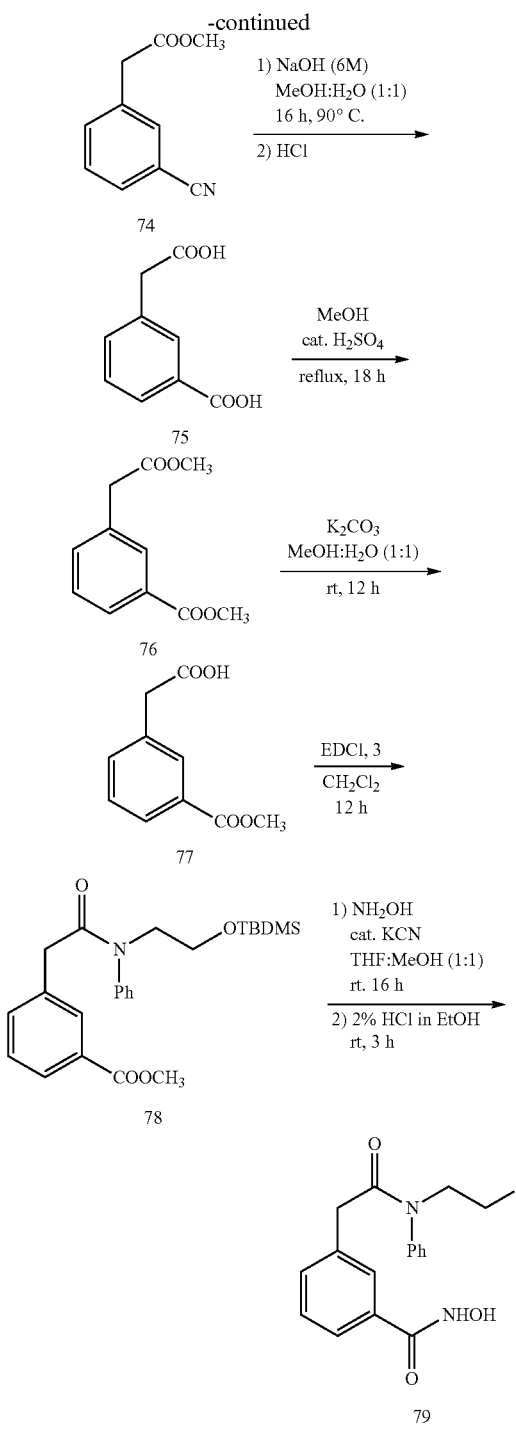

EtOAc, 5:1) to yield target compound 73. Yield 1.011 g, 95%. $R_f$=0.60, $^1$H NMR (400 MHz, Chloroform-d) δ 7.47-7.43 (m, 1H), 7.41 (dt, J=6.5, 2.2 Hz, 1H), 7.24-7.16 (m, 2H), 3.70 (s, 3H), 3.60 (s, 2H); [M+H]+=230.12 (APCI+).

Methyl 2-(3-cyanophenyl)acetate (74)

A mixture of 2-(3-bromophenyl)acetic acid 73, (1.0 g, 4.36 mmol) and CuCN (0.43 g, 4.80 mmol) in anhydrous DMF (10 mL) was refluxed overnight. The mixture was cooled to room temperature and poured into ice-water (100 mL), and the resulting precipitate was filtered. The solid was transferred to a beaker containing ethylenediamine (25 mL) and H$_2$O (10 mL), and the precipitate formed was extracted with CH$_2$Cl$_2$ (30 mL). The organic layer was washed with sat. NaCl (30 mL×2), dried (anhydrous sodium sulfate) and concentrated in vacuo. The crude product was chromatographed on silica gel (Hexanes/EtOAc, 5:1) to yield target compound 74. Yield 580 mg, 75%. $R_f$=0.38, $^1$H NMR (400 MHz, Methanol-d4) δ 7.69 (d, J=1.7 Hz, 1H), 7.64 (ddt, J=8.5, 7.0, 1.4 Hz, 2H), 7.52 (t, J=7.7 Hz, 1H), 3.78 (s, 3H), 3.73 (s, 2H); [M+H]+=176.13 (APCI+).

3-(carboxymethyl)benzoic acid (75)

6M Sodium hydroxide (10 mL) was added to methyl 2-(3-cyanophenyl)acetate 74, (550 mg, 3.14 mmol) in methanol (10 mL) and then heated at 90° C. overnight. After concentrating the reaction mixture, the aqueous layer was washed with CH$_2$Cl$_2$ (20 mL×2), then acidified to pH~3 with 12M HCl. The precipitate was extracted with ethyl acetate and washed with sat. NaCl (30 mL×2), dried (anhydrous sodium sulfate) and concentrated in vacuo. The crude product was chromatographed on silica gel (CH$_2$Cl$_2$/MeOH, 20:1) to yield target compound 75. Yield 508 mg, 90%. $R_f$=0.30, $^1$H NMR (400 MHz, Methanol-d$_4$) δ 8.06-7.87 (m, 2H), 7.54 (tt, J=5.7, 1.4 Hz, 1H), 7.45 (t, J=7.6 Hz, 1H), 3.71 (s, 2H); [M+H]+=181.15 (APCI+).

Methyl 3-(2-methoxy-2-oxoethyl)benzoate (76)

3-(carboxymethyl)benzoicacid (0.500 g, 2.77 mmol) was dissolved in freshly distilled methanol (25 mL). Added conc. H$_2$SO$_4$ (8 drops) and refluxed in a Dean-Stark apparatus for 16 hrs. Reaction mixture was cooled to room temperature and concentrated in vacuo. The crude product was dissolved in CH$_2$Cl$_2$ (40 mL) and washed with sat. NaHCO$_3$ (30 mL×2) and sat. NaCl (30 mL). The organic layer was dried (anhydrous sodium sulfate) and concentrated in vacuo. The crude product was chromatographed on silica gel (Hexanes/EtOAc, 5:1) to yield target compound 76. Yield 547 mg, 95%. $R_f$=0.60, $^1$H NMR (400 MHz, Chloroform-d) δ 7.98 (dd, J=6.2, 1.6 Hz, 2H), 7.51 (dt, J=7.6, 1.6 Hz, 1H), 7.47-7.40 (m, 1H), 3.94 (s, 3H), 3.73 (s, 3H), 3.71 (s, 2H); [M+H]+=209.25 (APCI+).

2-(3-(methoxycarbonyl)phenyl)acetic acid (77)

A solution of K$_2$CO$_3$ (700 mg, 5.07 mmol) in H$_2$O (10 mL) was added to a solution of methyl 3-(2-methoxy-2-oxoethyl)benzoate 76, (500 mg, 2.40 mmol) in methanol (10 mL) and stirred overnight at room temperature. Reaction mixture was concentrated and dissolved in water (20 mL). Aqueous later was extracted with EtOAc to the unreacted diester 76, acidified with 1N HCl, and extracted with EtOAc (30 mL×2). Organic layer was dried (anhydrous sodium sulfate) and concentrated in vacuo. The crude product was Methyl 2-(3-bromophenyl)acetate (73)

2-(3-bromophenyl)acetic acid (1.00 g, 4.65 mmol) was dissolved in freshly distilled methanol (50 mL). Added conc. H$_2$SO$_4$ (8 drops) and refluxed in a Dean-Stark apparatus for 3 hrs. Reaction mixture was cooled to room temperature and concentrated in vacuo. The crude product was dissolved in CH$_2$Cl$_2$ (40 mL) and washed with sat. NaHCO$_3$ (30 mL×2) and sat. NaCl (30 mL). The organic layer was dried (anhydrous sodium sulfate) and concentrated in vacuo. The crude product was chromatographed on silica gel (Hexanes/ chromatographed on silica gel (Hexanes/EtOAc, 5:1) to yield target compound 77. Yield 508 mg, 90%. $R_f$=0.36, $^1$H 1H NMR (400 MHz, Methanol-$d_4$) δ 7.97 (d, J=1.7 Hz, 1H), 7.91 (dt, J=7.8, 1.4 Hz, 1H), 7.57-7.49 (m, 1H), 7.43 (t, J=7.6 Hz, 1H), 3.91 (s, 3H), 3.67 (s, 2H); [M+H]+=195.14 (APCI+).

Methyl 3-(2-((2-((tert-butyldimethylsilyl)oxy)ethyl)(phenyl)amino)-2-oxoethyl)benzoate (78)

EDC (511 mg, 2.67 mmol) was added to a solution containing N-(2-((tertbutyldimethylsilyl)oxy)ethyl)aniline 3, (535 mg, 2.13 mmol) and 2-(3-(methoxycarbonyl)phenyl) acetic acid 77, (345 mg, 1.78 mmol) in $CH_2Cl_2$ (10 mL). The reaction mixture was stirred overnight at room temperature in argon atmosphere. After completion of reaction the reaction mixture was diluted with mixed solvent ($CHCl_3$:i-PrOH=4:1, 10 mL) and washed with sat. $NH_4Cl$. The organic layer was dried (anhydrous sodium sulfate) and concentrated in vacuo. The crude product was chromatographed on silica gel (Hexanes/EtOAc, 7:1) to yield target compound 78. Yield 732 mg, 70%. $R_f$=0.35, $^1$H NMR (400 MHz, Chloroform-d) δ 7.90 (ddd, J=5.6, 3.4, 1.7 Hz, 1H), 7.71 (s, 1H), 7.48-7.31 (m, 6H), 7.23-7.19 (m, 2H), 3.92 (s, 3H), 3.87-3.76 (m, 4H), 0.86 (s, 9H), 0.03 (s, 6H); [M+H]+=427.61 (APCI+).

3-(2-((2-((tert-butyldimethylsilyl)oxy)ethyl)(phenyl)amino)-2-oxoethyl)-N-hydroxybenzamide Hydroxylamine (1 mL, 50% water solution) was added to a solution containing methyl 3-(2-((2-((tert-butyldimethylsilyl)oxy)ethyl) (phenyl)amino)-2-oxoethyl)benzoate (200 mg, 0.468 mmol) in THF/MeOH (1:1, 2 mL). Reaction mixture was treated with cat. amount of KCN (~0.5 mg) and stirred at room temperature in argon atmosphere for 16 h. Then solution was acidified by $NH_4Cl$/HCl solution to pH 4. The mixture was diluted with mixed solvent ($CHCl_3$:i-PrOH=4:1, 10 mL) and washed with sat. $NH_4Cl$. The organic layer was dried (anhydrous sodium sulfate) and concentrated in vacuo. The crude product was purified by preparative chromatography on silica gel ($CH_2Cl_2$/MeOH, 10:1) to yield 3-(2-((2-((tert-butyldimethylsilyl)oxy)ethyl)(phenyl)amino)-2-oxoethyl)-N hydroxylbenzamide. Yield 40 mg, 66%. $R_f$=0.36, $^1$H NMR (400 MHz, Methanol-$d_4$) δ 7.60 (dt, J=7.7, 1.5 Hz, 1H), 7.53-7.38 (m, 4H), 7.39-7.26 (m, 3H), 7.25-7.18 (m, 1H), 3.85 (dd, J=6.8, 5.3 Hz, 2H), 3.77 (dd, J=6.1, 4.7 Hz, 2H), 3.53 (s, 2H), 0.87 (s, 8H), 0.04 (s, 6H); [M+H]+=429.28 (APCI+).

N-hydroxy-3-(2-((2-hydroxyethyl)(phenyl)amino)-2-oxoethyl)benzamide (79)

3-(2-((2-((tert-butyldimethylsilyl)oxy)ethyl)(phenyl)amino)-2-oxoethyl)-N-hydroxybenzamide, 3-(2-((2-((tert-butyldimethylsilyl)oxy)ethyl) (phenyl)amino)-2-oxoethyl)-N-hydroxybenzamide (60 mg, 0.14 mmol) was dissolved in 2% HCl in EtOH (5 mL) and stirred for 3 h. Then the reaction mixture was concentrated in vacuo. The crude product was purified by preparative chromatography on silica gel ($CH_2Cl_2$/MeOH, 10:1) to yield target compound 79. Yield 24 mg, 54%. $R_f$=0.28, $^1$H NMR (400 MHz, Methanol-$d_4$) δ 7.59 (d, J=7.7 Hz, 1H), 7.53-7.39 (m, 4H), 7.39-7.26 (m, 3H), 7.21 (d, J=7.7 Hz, 1H), 3.86 (t, J=6.0 Hz, 2H), 3.68 (t, J=6.0 Hz, 2H), 3.53 (s, 2H); $^{13}$C NMR (101 MHz, Methanol-$d_4$) δ 171.80, 166.64, 142.24, 135.94, 132.21, 129.52, 128.33, 128.24, 128.18, 127.57, 125.03, 58.38, 51.46, 40.52; [M+H]+ Calc.=315.1345. Found=315.1336 (FAB+).

Example 15

Biological Data

Recombinant HDAC1 and HDAC6 are used to evaluate the selective inhibitory potency of each compound. Cell based assays: Normal cells (Human Foreskin Fibroblast cells), LNCaP (human prostate cancer cells), MCF-7 (human breast cancer cells, A549 (human adenocarcinoma of lung cells) and ARP-1 (human multiple myeloma cells) are used in these assays. Cells were cultured for up to 72 hr without and with the potential HDAC6-selective inhibitor. SAHA was used as a control. Cell number and cell viability were determined by enumeration. Proteins were extracted from cells and assayed for accumulation of acetylated tubulin and acetylated histones. All methods are described in Namdar et al., PNAS, 2010, 107:20003-8. In vivo animal studies: Potential HDAC6 inhibitor compounds are further assayed by administration to mice for up to 5 days with daily injections. Animals are sacrificed and tissues are analyzed for accumulation of acetylated tubulin and acetylated histones.

DISCUSSION

Figure 2:
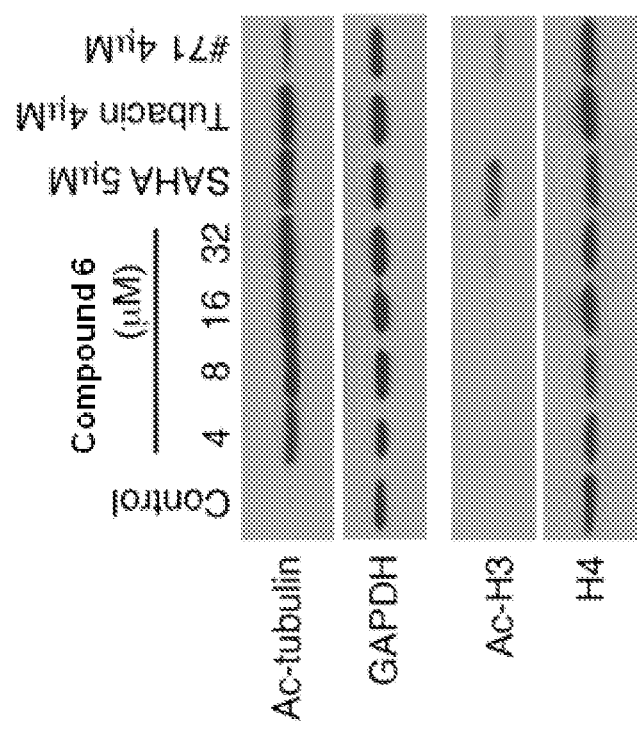
FIG. 2. Blot showing accumulation of acetylated alpha-tubulin and acetylated histone H3 in LNCaP cells cultured with compound 6. GADPH used as loading control.

HDAC6-selective inhibitors were identified on the basis of accumulation of acetylated tubulin without accumulation of acetylated histones. Compound 6 and 14 were identified as HDAC6-selective inhibitors. As show in FIG. 2, significant levels of tubulin acylation were present without induction of H3 acetylation. The levels of tubulin acetylation that can be reached with compound 6 in the absence of histone acetylation were greater than selective levels with tubacin.

Figure 3:
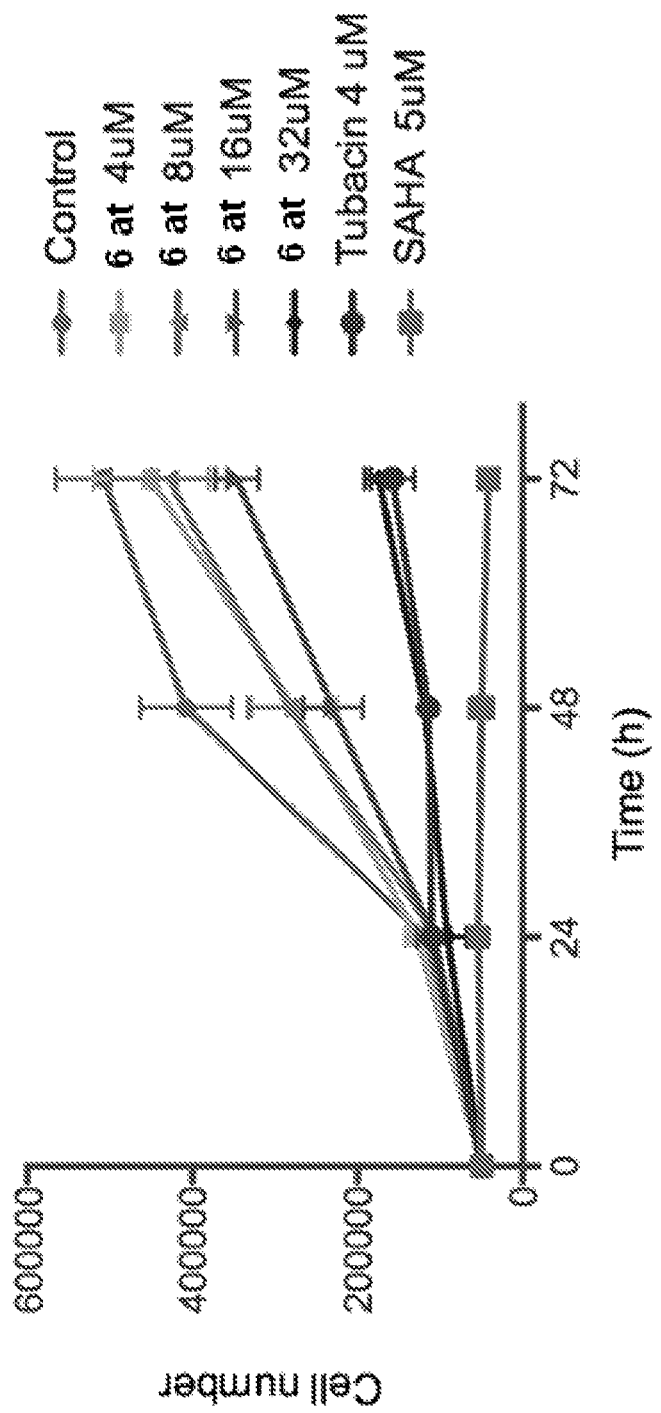
FIG. 3. Cell growth assay data in LNCaP cells with compound 6.
Figure 4:
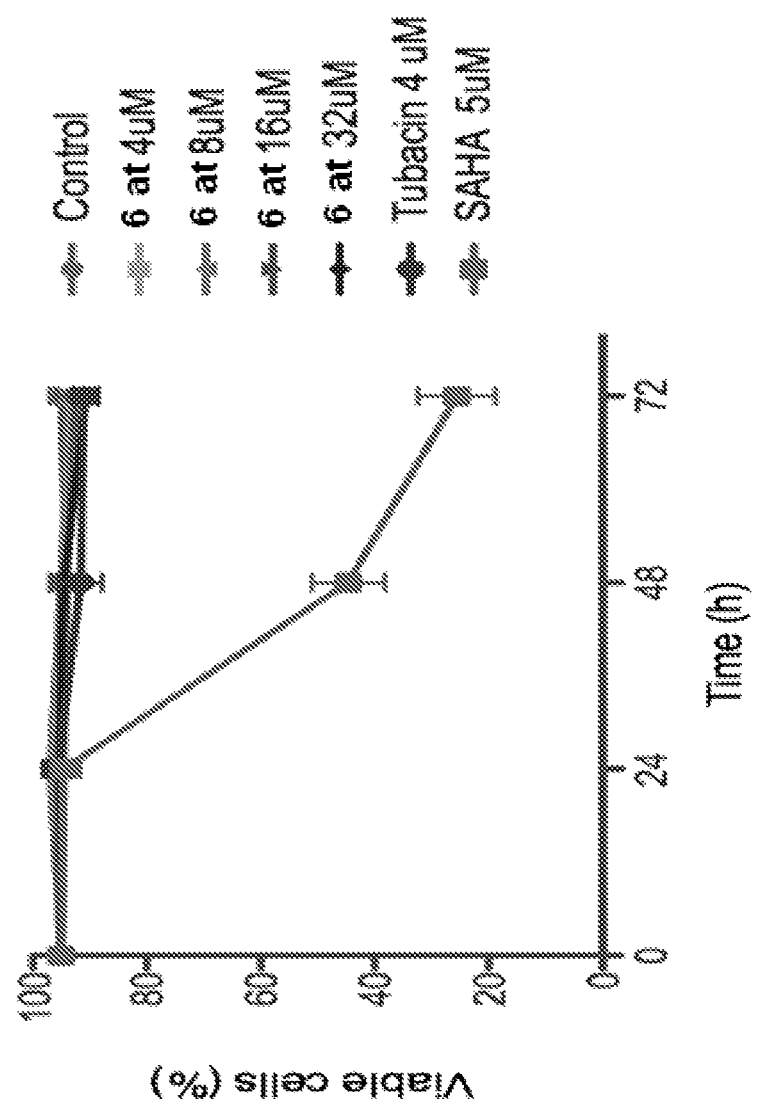
FIG. 4. Cell viability assay data in LNCaP cells with compound 6.

As indicated by the cell based (LNCaP-human prostate) assays, compounds 6 inhibits cell number (FIG. 3) but does not decrease cell viability (FIG. 4). Unlike SAHA, which kills LNCaP cells, there is no detectable death of LNCaP cells with compound 6 even at concentrations as high as 32 μM.

An additional aspect of the invention provides synthetic methods and chemical intermediates that may be used to synthesize additional HDAC inhibitors. Additional compounds, which are synthesized according to Schemes 4-7 or according to methods known in the art, are expected to function analogously to compound 6. Compounds with a variety of "Z" linkers are expected to function analogously to compound 6. The left hand portion of the compound ($R_1$, $R_2$ and $R_3$) is also varied in order to improve solubility and drug-like properties and is expected to function analogously to compound 6.

The compounds of the present invention are HDAC6 selective inhibitors. Compounds 6, 14 and 79 were HDAC inhibitors selective for HDAC6 relative to HDAC1. Compounds 21, 24, 26, 27, 28, 29, 30, 31, 32, 33, 34, 35, 36, 37, 38, 39, 40, 41, 42, and 43 are HDAC inhibitors selective for HDAC6 relative to HDAC1.

REFERENCES

1. R. B. Parmigiani, W. S. Xu, G. Yenta-Perez, H. Erdjument-Bromage, M. Yaneva, P. Tempst, and P. A. Marks.

"HDAC6 is a specific deacetylase of peroxiredoxins and is involved in redox regulation" *Proc. Nat. Acad. Sci. USA* (2008), 105, 9633-9638.
2. K. V. Butler and A. P. Kozikowski "Chemical Origins of Isoform Selectivity in Histone Deacetylase Inhibitors" *Curr. Pharma. Design* (2008), 14, 505-528.
3. Y. Kawaguchi; J. J. Kovacs; A. McLaurin; J. M. Vance; A. Ito; T.-P. Yao "The Deacetylase HDAC6 Regulates Aggresome Formation and Cell Viability in Response to Misfolded Protein Stress" *Cell* (2003), 115, 727-738.
4. P. Bali; M. Pranpat; J. Bradner; M. Balasis; W. Fiskus; F. Guo; K. Rocha; S. Kumaraswamy; S. Boyapalle; P. Atadja; E. Seto; K. Bhalla. "Inhibition of Histone Deacetylase 6 Acetylates and Disrupts the Chaperone Function of Heat Shock Protein 90" *J. Biol. Chem.* (2005), 280, 26729-26734.
5. Y.-S. Gao; C. C. Hubbert; T.-P. Yao. "The Microtubule-associated Histone Deacetylase 6 (HDAC6) Regulates Epidermal Growth Factor Receptor (EGFR) Endocytic Trafficking and Degradation" *J. Biol. Chem.* (2010), 285, 11219-11226.
6. S. J. Haggarty; K. M. Koeller; J. C. Wong; C. M. Grozinger; S. L. Schreiber. "Domain-selective small-molecule inhibitor of histone deacetylase 6 (HDAC6)-mediated tubulin deacetylation" *Proc. Nat. Sci. Acad. USA* (2003), 100, 4389-4394.
7. J. J. Kovacs; P. J. M. Murphy; S. Gaillard; X. Zhao; T. Wu; C. V. Nicchitta; M. Yoshida; D. O. Toft; W. B. Pratt; T.-P. Yao. "HDAC6 Regulates Hsp90 Acetylation and Chaperone-Dependent Activation of Glucocorticoid Receptor" *Molecular Cell* (2005) 18, 601-607.
8. Marks, P. S., Breslow, R. Dimethyl sulfoxide to vorinostat: development of this histone deacetylase inhibitor as an anti-cancer drug. *Nat. Biotech.* (2007) 25, 84-90.
9. Marks, P. A. Histone Deacetylase Inhibitors: A chemical genetics approach to understanding cellular functions, *Biochimica et. Biophysicia Acta* (2010) 1799 (10-12), 717-725.
10. Munkacsi, Andrew B. et al., "An "exacerbate-reverse" strategy in yeast identifies histone deacetylase inhibition as a correction for cholesterol and sphingolipid transport defects in human niemann-pick type C disease", *J. Biol. Chem.* (2011) 286, 23842-23851.

What is claimed is:
1. A compound having the structure:

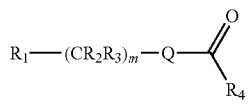

wherein
$R_1$ is —$NR_5$—C(=O)—$R_6$ or —C(=O)—$NR_5R_6$,
wherein
$R_5$ is

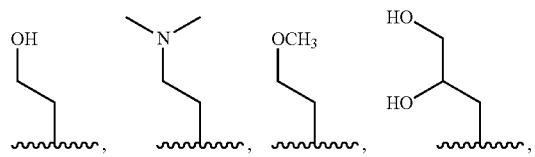

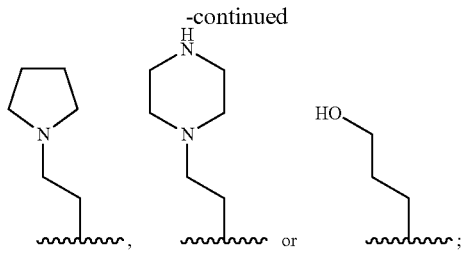

$R_6$ is

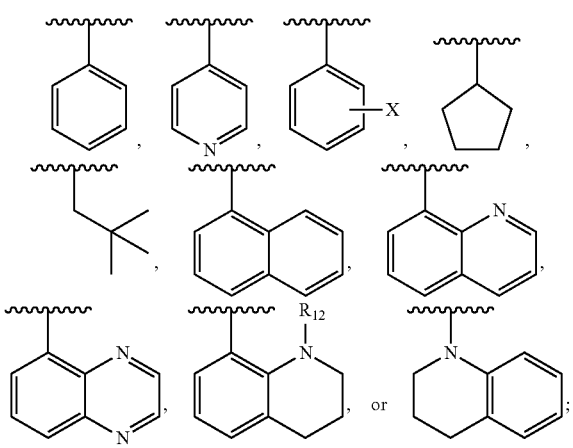

wherein
X is a Cl, Br, or F; and
$R_{12}$ is H, $C_{1-6}$ alkyl, $C_{2-6}$ alkenyl, $C_{2-6}$ alkynyl, heteroalkyl, cycloalkyl, heterocycloalkyl, aryl, or heteroaryl;
m is an integer from 0 to 2;
$R_2$ and $R_3$ are each, independently, H, halogen, —$NH_2$, —$CX_3$, —C(=O)$OR_8$, C(=O)$R_8$, —C(=O)$NR_9R_{10}$, $C_{1-10}$ alkyl, $C_{2-10}$ alkenyl, $C_{2-10}$ alkynyl, heteroalkyl, aryl, heteroaryl, or heterocyclyl;
wherein
X is Cl, Br, or F;
$R_8$, $R_9$ and $R_{10}$ are each, independently, H, $C_{1-6}$ alkyl, $C_{2-6}$ alkenyl, $C_{2-6}$ alkynyl, heteroalkyl, cycloalkyl, heterocycloalkyl, aryl, or heteroaryl;
Q is —$Ar_1$—Z— or —Z—$Ar_1$—Z—,
wherein $Ar_1$ is

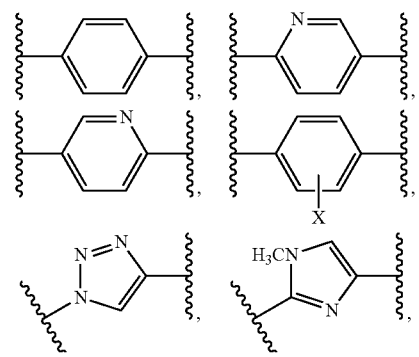

-continued wherein X is a Cl, Br, or F; and
each Z is absent; and
$R_4$ is alkyl, $-OR_{11}$ or $-NH-OR_{11}$,
  wherein $R_{11}$ is H, $C_{1-10}$ alkyl, $C_{2-10}$ alkenyl, $C_{2-10}$ alkynyl, aryl, heteroaryl, or heterocyclyl,
or a pharmaceutically acceptable salt thereof.

2. The compound of claim 1 having the structure:

$$R_1-(CR_2R_3)_m-Ar_1-Z-C(=O)-R_4$$

wherein
$R_1$ is $-NR_5-C(=O)-R_6$ or $-C(=O)-NR_5R_6$,
  wherein
  $R_5$ is

[structures shown]

$R_6$ is

[structures shown]

wherein
X is a Cl, Br, or F; and
$R_{12}$ is H, $C_{1-5}$ alkyl, $C_{2-5}$ alkenyl, $C_{2-5}$ alkynyl, heteroalkyl, cycloalkyl, heterocycloalkyl, aryl, or heteroaryl;
m is an integer from 0 to 2;
$R_2$ and $R_3$ are each, independently, H, halogen, $-NH_2$, $-CX_3$, $-C(=O)OR_8$, $C(=O)R_8$, $-C(=O)NR_9R_{10}$, $C_{1-10}$ alkyl, $C_{2-10}$ alkenyl, $C_{2-10}$ alkynyl, heteroalkyl, aryl, heteroaryl, or heterocyclyl;
wherein
X is Cl, Br, or F;
$R_8$, $R_9$ and $R_{10}$ are each, independently, H, $C_{1-5}$ alkyl, $C_{2-5}$ alkenyl, $C_{2-5}$ alkynyl, heteroalkyl, cycloalkyl, heterocycloalkyl, aryl, or heteroaryl;
$Ar_1$ is

[structures shown]

wherein X is a Cl, Br, or F;
Z is absent; and
$R_4$ is $-OR_{11}$ or $-NH-OR_{11}$,
  wherein $R_{11}$ is H, $C_{1-10}$ alkyl, $C_{2-10}$ alkenyl, $C_{2-10}$ alkynyl, aryl, heteroaryl, or heterocyclyl,
or a pharmaceutically acceptable salt thereof.

3. The compound of claim 1,
wherein $R_4$ is $-OR_{11}$ or $-NH-OR_{11}$,
  wherein $R_{11}$ is H or $CH_3$,
or a pharmaceutically acceptable salt thereof.

4. The compound of claim 2,
wherein $R_4$ is $-OR_{11}$ or $-NH-OR_{11}$,
  wherein $R_{11}$ is H or $CH_3$,
or a pharmaceutically acceptable salt thereof.

5. The compound of claim 1,
wherein m=1;
$R_2$ is H or $CH_3$; and
$R_3$ is H, $CH_3$, Cl, Br, F, or $CF_3$,
or a pharmaceutically acceptable salt thereof.

6. The compound of claim 2,
wherein m=1;
$R_2$ is H or $CH_3$; and
$R_3$ is H, $CH_3$, Cl, Br, F, or $CF_3$,
or a pharmaceutically acceptable salt thereof.

7. The compound of claim 1, wherein
R$_5$ is

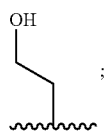

and
R$_6$ is

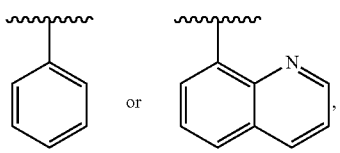 [SMILES: *c1ccccc1 ; *c1cccc2cccnc12]

or a pharmaceutically acceptable salt thereof.

8. The compound of claim 2, wherein
R$_5$ is

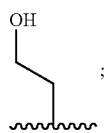

and
R$_6$ is

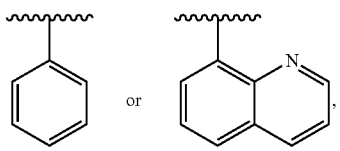 [SMILES: *c1ccccc1 ; *c1cccc2cccnc12]

or a pharmaceutically acceptable salt thereof.

9. The compound of claim 1 having the structure:

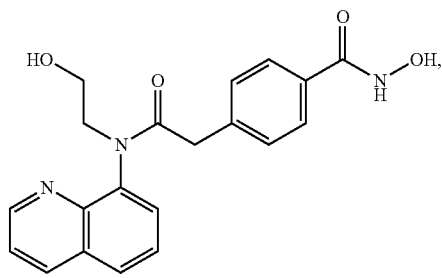 [SMILES: O=C(NO)c1ccc(CC(=O)N(CCO)c2cccc3cccnc23)cc1]

or a pharmaceutically acceptable salt thereof.

10. The compound of claim 1 having the structure:

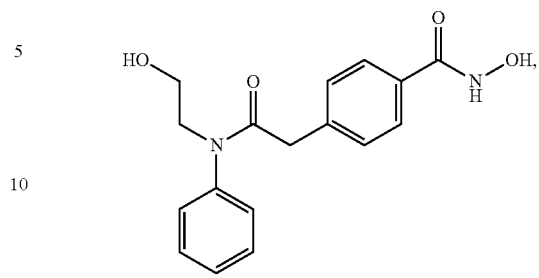

or a pharmaceutically acceptable salt thereof.

11. The compound of claim 1 having the structure:

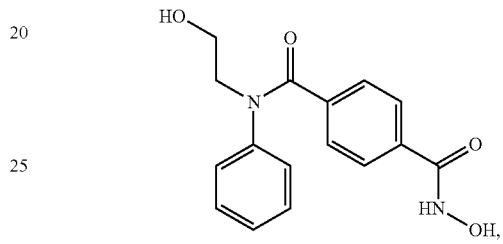

or a pharmaceutically acceptable salt thereof.

12. A pharmaceutical composition comprising the compound of claim 1 and a pharmaceutically acceptable carrier.

13. A method of inhibiting the activity of a histone deactylase in a cell comprising contacting the histone deacetylase with the compound of claim 1 so as to inhibit the activity of the histone deacetylase.

14. A method of inhibiting the activity of a histone deacetylase 6 (HDAC6) in a cell comprising contacting the histone deacetylase 6 with the compound of claim 1 so as to inhibit the activity of the histone deacetylase 6 in the cell.

15. A method of increasing accumulation of acetylated alpha tubulin in a cell comprising contacting the cell with the compound of claim 1 so as to increase the accumulation of acetylated alpha-tubulin in the cell.

16. A pharmaceutical composition comprising the compound of claim 2 and a pharmaceutically acceptable carrier.

17. A method of inhibiting the activity of a histone deactylase in a cell comprising contacting the histone deacetylase with the compound of claim 2 so as to inhibit the activity of the histone deacetylase.

18. A method of inhibiting the activity of a histone deacetylase 6 (HDAC6) in a cell comprising contacting the histone deacetylase 6 with the compound of claim 2 so as to inhibit the activity of the histone deacetylase 6 in the cell.

19. A method of increasing accumulation of acetylated alpha tubulin in a cell comprising contacting the cell with the compound of claim 2 so as to increase the accumulation of acetylated alpha-tubulin in the cell.

* * * * *